US010335504B2

(12) United States Patent
Sundaram et al.

(10) Patent No.: US 10,335,504 B2
(45) Date of Patent: Jul. 2, 2019

(54) HETEROCYCLIC MOLECULES FOR BIOMEDICAL IMAGING AND THERAPEUTIC APPLICATIONS

(71) Applicant: Washington University, Saint Louis, MO (US)

(72) Inventors: G. S. M. Sundaram, Saint Louis, MO (US); Jothilingam Sivapackiam, Saint Louis, MO (US); Vijay Sharma, Wildwood, MO (US)

(73) Assignee: Washington University, St. Louis, MO (US)

( * ) Notice: Subject to any disclaimer, the term of this patent is extended or adjusted under 35 U.S.C. 154(b) by 132 days.

(21) Appl. No.: 15/089,516

(22) Filed: Apr. 2, 2016

(65) Prior Publication Data

US 2016/0213792 A1      Jul. 28, 2016

Related U.S. Application Data

(63) Continuation of application No. PCT/US2014/058919, filed on Oct. 2, 2014.

(60) Provisional application No. 61/885,571, filed on Oct. 2, 2013.

(51) Int. Cl.
| | | |
|---|---|---|
| *A61K 51/00* | (2006.01) | |
| *A61M 36/14* | (2006.01) | |
| *A61K 51/04* | (2006.01) | |
| *C07F 7/18* | (2006.01) | |
| *C07D 417/06* | (2006.01) | |
| *C07D 421/06* | (2006.01) | |
| *C07D 277/64* | (2006.01) | |
| *C07D 277/66* | (2006.01) | |
| *C07D 293/12* | (2006.01) | |
| *C07B 59/00* | (2006.01) | |
| *G01N 33/60* | (2006.01) | |
| *G01N 33/68* | (2006.01) | |

(52) U.S. Cl.
CPC ...... *A61K 51/0459* (2013.01); *A61K 51/0453* (2013.01); *A61K 51/0455* (2013.01); *A61K 51/0465* (2013.01); *C07B 59/002* (2013.01); *C07D 277/64* (2013.01); *C07D 277/66* (2013.01); *C07D 293/12* (2013.01); *C07D 417/06* (2013.01); *C07D 421/06* (2013.01); *C07F 7/1804* (2013.01); *G01N 33/60* (2013.01); *G01N 33/6893* (2013.01); *G01N 33/6896* (2013.01); *G01N 2333/4709* (2013.01); *G01N 2800/2821* (2013.01); *G01N 2800/32* (2013.01)

(58) Field of Classification Search
CPC ... C07F 7/1804; A61K 51/0459; G01N 33/60; G01N 33/6896; G01N 2333/4709; G01N 2800/2821; C07B 59/002

USPC ............................................ 424/1.89
See application file for complete search history.

(56) References Cited

U.S. PATENT DOCUMENTS

| | | | |
|---|---|---|---|
| 8,163,928 B2 | 4/2012 | Gravenfors et al. | |
| 2007/0031328 A1* | 2/2007 | Kung | A61K 47/48215 424/1.11 |
| 2012/0035187 A1* | 2/2012 | Ohta | C07D 209/14 514/254.08 |

FOREIGN PATENT DOCUMENTS

| | | |
|---|---|---|
| WO | 2002/016333 A2 | 2/2002 |
| WO | 2004/083195 A1 | 9/2004 |
| WO | 2007/047204 A1 | 4/2007 |
| WO | 2007/086800 A1 | 4/2007 |
| WO | 2009/062138 A1 | 5/2009 |

OTHER PUBLICATIONS

Okamura et al. J. Neurosci. 2004, 24, 2535-2541.*
Zhang et al. Curr. Top. Med. Chem. 2007, 7, 1817-1828.*
Henriksen et al. J. Med. Chem. 2007, 50, 1087-1089.*
Koffie et al. PNAS 2011, 108, 18837-18842.*
Song et al. Angew. Chem. Int. Ed. 2009, 48, 9143-9147.*
Abbas, A., et al., Molecular linker-mediated self-assembly of gold nanoparticles: understanding and controlling the dynamics., Langmuir, 2013, 29, 56-64.
Agdeppa, E., et al., Binding characteristics of radiofluorinated 6-dialkylamino-2-naphthylethylidene derivatives as positron emission tomography imaging probes for beta-amyloid plaques in Alzheimer's disease, J. Neurosci., 21, RC189, 2001.
Agdeppa, E., et al., In vitro detection of (S)-naproxen and ibuprofen binding to plaques in the Alzheimer's brain using the positron emission tomography molecular imaging probe 2-(1-[6-[(2-[(18)F]fluoroethyl)(methyl)amino]-2-naphthyl] ethylidene)malononitrile., Neuroscience, 117, 723-730, 2003.
Choi, S.R., et al., Preclinical properties of 18F-AV-45: a PET agent for Aβ plaques in the brain., J Nucl Med 50, 1887-1894, 2009.

(Continued)

*Primary Examiner* — Michael G. Hartley
*Assistant Examiner* — Sean R Donohue
(74) *Attorney, Agent, or Firm* — Zackson Law LLC; Saul L. Zackson

(57) ABSTRACT

Probes which target diffuse and fibrillar forms of amyloid beta (Aβ) are described. These probes demonstrate high initial brain penetration and facile clearance from non-targeted regions. The agents can be used to image amyloid quantitatively for monitoring efficacy of Aβ-modifying therapeutics and assist in premortem diagnosis of Alzheimer's disease (AD). Disclosed probes can bind Aβ aggregates of preformed $A\beta_{1-42}$ fibrils in vitro and can be used to image fibrillar and diffuse plaques ex vivo in brain sections. Disclosed probes can be used to determine Aβ burden in early stages of AD. These probes can be used for multimodality imaging of Aβ. F-AI-187 (1 µM) can detect Aβ plaques in brain sections of APP/PS1 mice. F-AI-187 (10 µM) can detect Aβ plaques in the frontal lobe in a brain section of a patient with confirmed AD. Some probes can be used for fluorescence imaging of plaque.

8 Claims, 10 Drawing Sheets

(56) References Cited

OTHER PUBLICATIONS

Cui, M., et al., Synthesis and evaluation of novel $^{18}$F labeled 2-pyridinylbenzoxazole and 2-pyridinylbenzothiazole derivatives as ligands for positron emission tomography (PET) imaging of β-amyloid plaques., J. Med. Chem., 55, 9283-9296, 2012.

Hsiao, I.T., et al., Correlation of early-phase 18F-florbetapir (AV-45/Amyvid) PET images to FDG images: preliminary studies., Eur. J. Nucl. Med. Mol. Imaging, 39, 613-620, 2012.

Kung, M.P., et al., IMPY: an improved thioflavin-T derivative for in vivo labeling of beta-amyloid plaques., Brain Res., 956, 202-210, 2002.

Lockhart, A., et al., Evidence for the presence of three distinct binding sites for the thioflavin T class of Alzheimer's disease PET imaging agents on beta-amyloid peptide fibrils., J. Biol. Chem., 280, 7677-7684, 2005.

Lugovkin, B.P., Condensation of 2-pyridinecarboxaldehyde with heterocyclic bases. Synthesis of 1-pyridyl-2-quinolyl-, 1-benzothiazolyl-2-pyridyl-, and 1-benzoselenazolyl-2-pyridylethylenes and their methiodides., Khimia Geterotsiklicheskikh Soedineniy, 1966, 4, pp. 571-574 (cited in International Search Report).

Mathis, C., et al., Synthesis and evaluation of 11C-labeled 6-substituted 2-arylbenzothiazoles as amyloid imaging agents., J. Med. Chem., 46, 2740-2754, 2003.

Narra, R., et al., A Neutral Tc-99m Complex for Myocardial Imaging. J. Nucl. Med. 30, 1830-1837, 1989.

Nordberg, A., PET imaging of amyloid in Alzheimer's disease., Lancet Neurol. 3, 519-527, 2004.

Rabinovici, G.D., et al., 11C-PIB PET imaging in Alzheimer disease and frontotemporal lobar degeneration, Neurology 68, 1205-1212, 2007.

Registry via STN, Dec. 3, 2009, RN 1195521-46-0 (cited in International Search Report).

Registry via STN, Mar. 21, 2005, RN 846055-73-0 (cited in International Search Report).

Shoghi-Jadid, K., et al., Localization of neurofibrillary tangles and beta-amyloid plaques in the brains of living patients with Alzheimer disease., Am. J. Geriatr. Psychiatry 10, 24-35, 2002.

Sundaram, G.S.M, et al., A New Nucleoside Analogue with Potent Activity against Mutant sr39 Herpes Simplex Virus-1 (HSV-1) Thymidine Kinase (TK). Organic letters, 14(14), 3568-3571, 2012.

Sundaram, G.S.M., et al., Characterization of a Brain Permeant Fluorescent Molecule and Visualization of Aβ Parenchymal Plaques, Using Real-Time Multiphoton Imaging in Transgenic Mice. Organic Letters, 16(14) pp. 3640-3643, 2014 (cited in International Search Report).

Verhoeff, N.P., et al., In-vivo imaging of Alzheimer disease beta-amyloid with [11C]SB-13 PET., Am. J. Geriatr. Psychiatry 12:584-595, 2004.

Ye, L., et al., Delineation of positron emission tomography imaging agent binding sites on beta-amyloid peptide fibrils., J. Biol. Chem. 280, 23599-23604 2005.

Zhang, W., 18F-labeled styrylpyridines as PET agents for amyloid plaque imaging., Nucl. Med. Biol. 34, 89-97, 2007.

Zhuang, Z.P., et al., Radioiodinated styrylbenzenes and thioflavins as probes for amyloid aggregates., J. Med. Chem. 44:1905-1914, 2001.

\* cited by examiner

HETEROCYCLIC MOLECULES FOR BIOMEDICAL IMAGING AND THERAPEUTIC APPLICATIONS

CROSS REFERENCE TO RELATED APPLICATION

This application claims priority benefit of International Application PCT/US14/58919 filed on Oct. 2, 2014, which claims priority to U.S. Provisional Application Ser. No. 61/885,571 filed Oct. 2, 2013. Each of these applications is incorporated herein by reference, each in its entirety.

STATEMENT REGARDING FEDERALLY SPONSORED RESEARCH

This invention was made with government support under (identify the contract) awarded by (identify the Federal agency). The government has certain rights in the invention.

INTRODUCTION

Approximately 4 million Americans suffer from Alzheimer's disease (AD), a progressive neurodegenerative disorder with an estimated annual healthcare cost of $100 billion. AD can involve the appearance of distinct abnormal proteinaceous deposits: extracellular amyloid plaques that are characteristic of AD, and intracellular neurofibrillary tangles, which can also be found in other neurodegenerative disorders. Accumulation of amyloid beta (Aβ) can be an initiating event in the pathogenic cascade of AD. An overexpression of amyloid precursor protein (APP) is characteristic of Down Syndrome (DS), and early onset AD has been shown to be present in these patients (Teller, J., Nature Med. 2, 93-95 (1996); Lemere, C., et al. Neurobiol. Disease 3, 16-32, 1996).

Neuropathological criteria for AD currently rely on densities of senile plaques (SPs) and neurofibrillary tangles (NFTs) to differentiate AD and aging. The presence of SPs and NFTs in non-demented older adults can represent AD at a stage prior to clinical expression (Price, J. L., et al. Neurobiology of Aging 30, 1026-1036, 2009). Amyloid formation can commence prior to the start of a neurodegeneration phase.

Radiopharmaceuticals such as $^{11}$C-PIB (2-[p-(Methylamino)phenyl]-3-thia-1-aza-5-indanol,

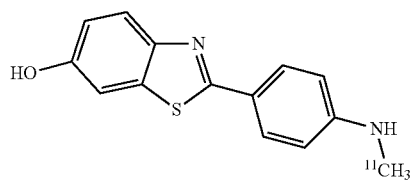 [SMILES: [11CH3]Nc1ccc(-c2nc3ccc(O)cc3s2)cc1]

(Rabinovici, G. D., et al., Neurology 68: 1205-1212, 2007); $^{18}$F-FDDNP (2-(1-(6-[(2-[18F]fluoroethyl)(methyl)amino]-2-naphthyl)ethylidene)malononitrile,

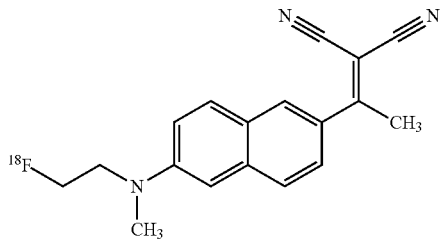 [SMILES: CC(=C(C#N)C#N)c1ccc2cc(N(C)CC[18F])ccc2c1]

(Shoghi-Jadid, K., et al., Am. J. Geriatr. Psychiatry 10: 24-35, 2002); [$^{11}$C]-SB-13 ([$^{11}$C]4-N-methylamino-4'-hydroxystilbene,

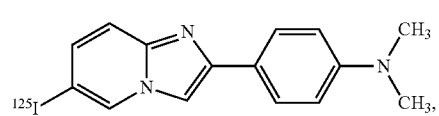 [SMILES: CN(C)c1ccc(-c2cn3cc([125I])ccc3n2)cc1]

(Verhoeff, N. P., et al., Am. J. Geriatr. Psychiatry 12:584-595, 2004) and $^{18}$F-AV-45

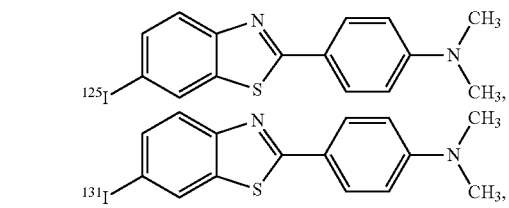

(Hsiao, I. T., et al., Eur. J. Nucl. Med. Mol. Imaging 39, 613-620, 2012) have been investigated in humans as probes for PET imaging of Aβ. In addition, [$^{125}$I/$^{131}$I]-TZDM ([$^{125}$I/$^{131}$I]2-(4'-dimethylaminophenyl)-6-iodobenzothiazole, (Zhuang, Z. P., et al, J. Med. Chem. 44:1905-1914, 2001) and $^{125}$I-IMPY ([$^{125}$I] 6-iodo-2-(4'-dimethylamino-)phenyl-imidazo[1,2-a]pyridine, Kung, M. P., et al., Brain Res. 956:202-210, 2002) have also been investigated for SPECT applications. While $^{11}$C-PIB has been most intensely studied, $^{18}$F-AV-45 ((E)-4-(2-(6-(2-(2-(2-([$^{18}$F]-fluoroethoxy)ethoxy)ethoxy)pyridin-3-yl)vinyl)-N-methyl benzenamine,
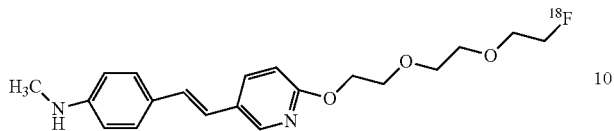
has also been approved by FDA for Aβ imaging. Other examples of ligands for Aβ aggregates include
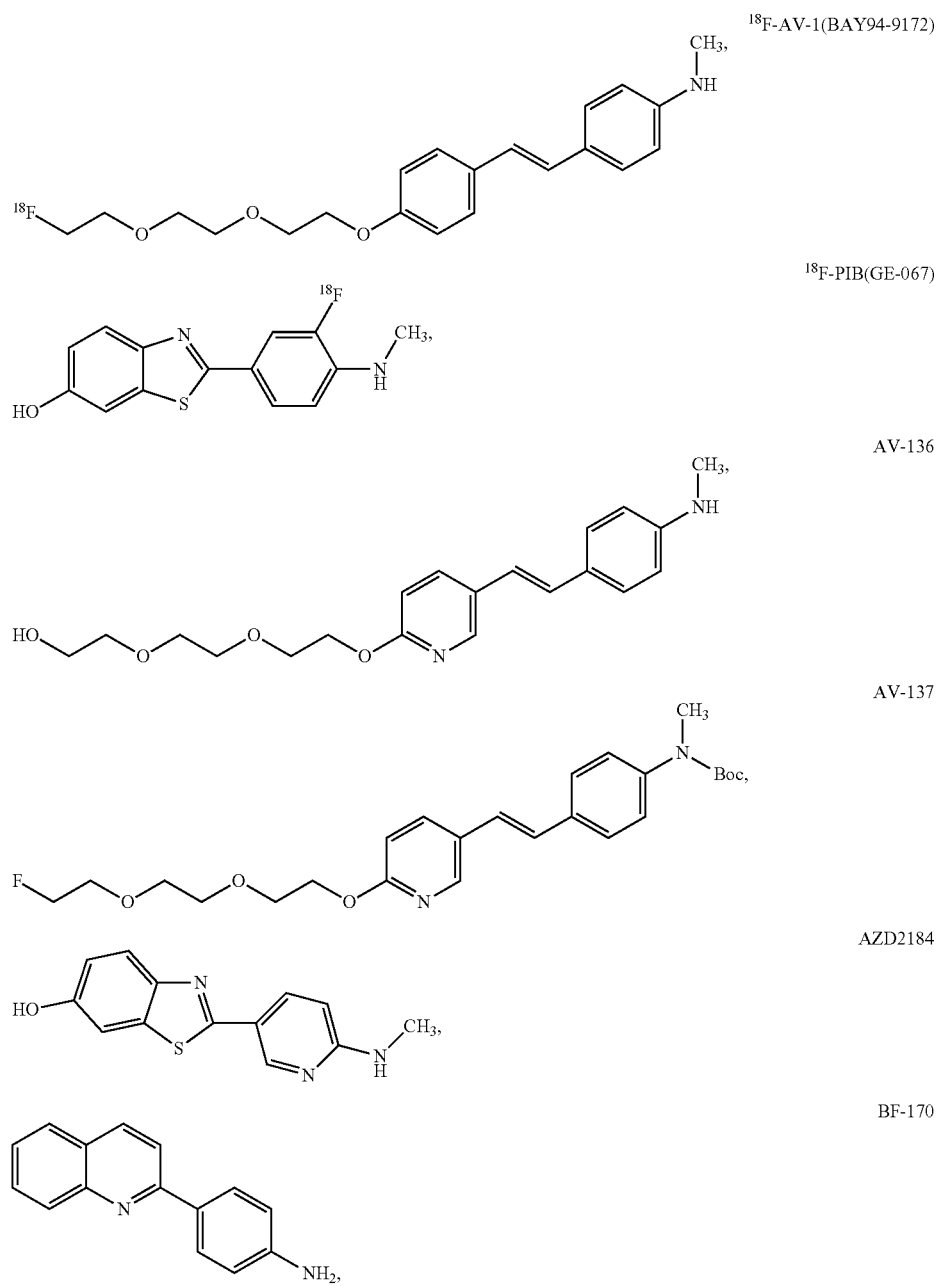

-continued

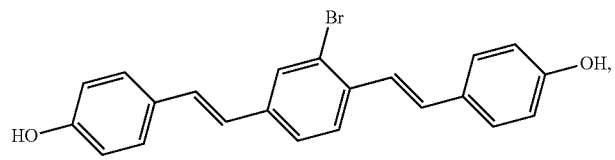
K114

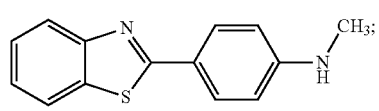
BTA-1

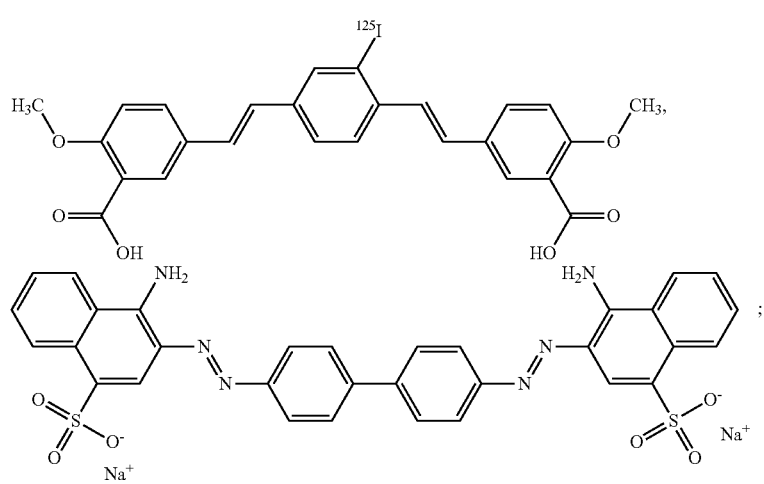
IMSB

Congo Red

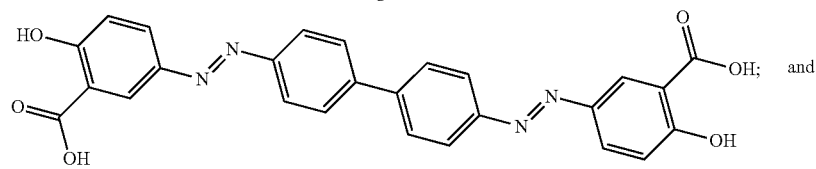

Chrysamine G(CG)

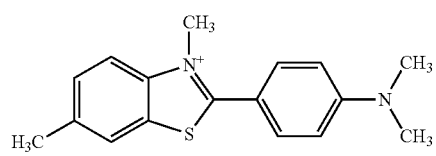

Thioflavin T (Choi, S. R., et al., J. Nucl. Med. 50: 1887-1894, 2009; Cui, M., et al., J. Med. Chem. 55, 9283-9296, 2012).

However, each of the established ligands for Aβ aggregates has its drawbacks. For example, $^{11}$C-PIB, SB-13, and $^{18}$F-AV-45 each exhibit low biological half-life in serum. While metabolites of PIB have been postulated not to penetrate the brain (Nordberg, A. Lancet Neurol. 3, 519-527, 2004; Mathis, C., et al. J. Med. Chem. 46, 2740-2754 2003), two metabolites of $^{18}$F-AV-45, i.e.,

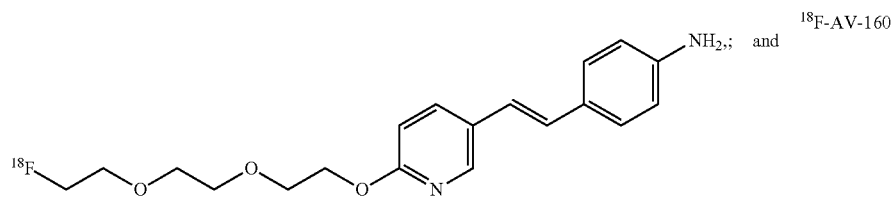
$^{18}$F-AV-160

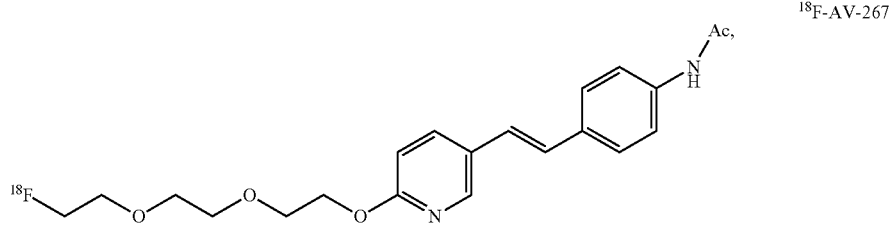

$^{18}$F-AV-267 have been shown to permeate the brain (4.5% injected dose/gram (ID/g) and 3.3% ID/g respectively, at 2 min in normal mice) thus complicating analysis (Choi, S. R., et al. J. Nucl. Med. 50, 1887-1894, 2009). Systematic investigations of PIB binding (at the tracer concentrations achieved during in vivo imaging scans) to human neuropathological brain specimens indicated PIB binding to classical plaques, neurofibrillary tangles, and cerebrovascular amyloid angiopathy (CAA) that was not displaceable, indicating limited utility of PIB to diagnose and monitor progression of the disease. (Lockhart, A., et al., Brain 130, 2607-2615, 2007). FDDNP has been shown to bind to neurofibrillary tangles and prion plaques in addition to fibrillar Aβ, demonstrating a lack of specificity towards probing AD (Nordberg, A., Lancet Neurol. 3, 519-527, 2004; Agdeppa, E., et al. J. Neurosci. 21, RC189, 2001; Agdeppa, E., et al., Neuroscience 117, 723-730, 2003). FDDNP has been shown to bind both BS1 and BS3 sites with low affinity (Ye, L., et al. J. Biol. Chem. 280, 23599-23604 2005).

U.S. Pat. No. 8,163,928 to Gravenfors, assigned to AstraZeneca, discloses structure

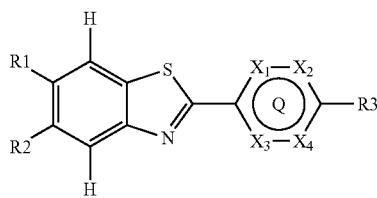

wherein R1 can be, inter alia, $C_1$-$C_6$ fluoroalkoxy; R2 can be H; Q is an aromatic ring; $X_1$ can be C; $X_2$ can be N, $X_3$ can be C and $X_4$ can be C; and R3 can be $N(C_{1-3}$ alkyl$)_2$. This patent includes structure

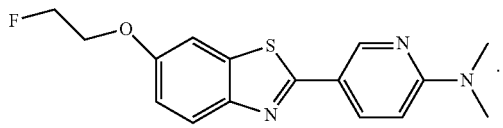 [SMILES: CN(C)c1ccc(-c2nc3ccc(OCCF)cc3s2)cn1]

However, the structure disclosed in U.S. Pat. No. 8,163,928 has only a bond linking the benzothiazole moiety and the pyridine moiety.

$^{18}$F-agents such as flutemetamol ($^{18}$F-PIB), florbetaben (BAYER 94-9172) and florbetapir (AV-45) (Choi, S. R., et al., J. Nucl. Med. 50, 1887-1894, 2009; Zhang, W., Nucl. Med. Biol. 34, 89-97, 2007) show high levels of nonspecific white matter retention that can be attributed to high lipophilicity. This high level of nonspecific retention can limit the sensitivity of PET imaging in a prodromal phase of disease when plaque levels are low. Combined with the possibility that these agents could be targeting the same binding site on Aβ, the diagnostic potential of existing imaging agents to segregate patients at earlier stages of the disease to benefit from available therapeutics is debatable. PIB, AV-45, and other agents have been known to bind weakly to amorphous cortical plaques (Ikonomovic, M. D., et al., Brain 131, 1630-1645, 2008; Bacskai, B. J., et al., Arch. Neurol. 64, 431-434, 2007). These agents target fibrillar plaques and interact weakly with diffuse plaques that occur in early stages of the disease prior to clinical manifestation of symptoms.

Previous agents have shown white matter binding, which provides a challenge for analysis in early stages of AD. For example, $^{11}$C-PIB binding of cerebral Aβ was reported below the level required for detection in a patient (Cairns, N. J., et al., Arch. Neurol. 66, 1557-1562, 2009) thus raising concerns for PIB and other agents in their sensitivity to detect AD variants characterized predominantly by diffuse Aβ plaques. Agents such as PIB and AV-45 have been postulated to bind a high affinity and low dense site on fibrils (Lockhart, A., et al., J. Biol. Chem. 280, 7677-7684, 2005) thus raising further concerns regarding their diagnostic potential to map early stages of AD. Because the presence of senile plaques in non-demented older adults can represent an early manifestation of AD prior to its clinical expression (Price, J. L., et al., Neurobiology of Aging 30, 1026-1036, 2009; Morris, J. C., et al., Neurology 46, 707-719, 1996; Price, J. L. & Morris, J. C., Annals of Neurology 45, 358-368, 1999; Schmitt, F. A., et al., Neurology 55, 370-376, 2000) the orientation of Aβ binding sites can also be different at earlier stages. Thus, additional ligands for amyloid beta are needed.

SUMMARY

The present inventors have developed tracers for detecting amyloid beta (Aβ). In various embodiments, the tracers can include radionuclides for imaging using known imaging modalities such as PET scanning or SPECT scanning. In various embodiments, the tracers can have fluorescence properties, and can be used for optical imaging. In various embodiments, tracers of the present teachings can possess enhanced specificity (minimal white matter binding) and/or enhanced sensitivity compared to $^{11}$C-PIB or $^{18}$F-AV-45. In some embodiments, a disclosed tracer can be capable of targeting binding sites different from those targeted by $^{11}$C-PIB or $^{18}$F-AV-45. In some embodiments, a disclosed tracer can provide diagnostic PET agents for Aβ imaging at earlier stages of Alzheimer's disease compared to tracers such as $^{11}$C-PIB or $^{18}$F-AV-45. In some embodiments, a disclosed tracer can be used to monitor efficacy of therapeutics. In some embodiments, a disclosed tracer such as, without limitation, $^{18}$F-AI-187, can be used for imaging and/or diagnosis of a tumor such as, without limitation, a prolactinoma, a chroid plexus papilloma, a low grade lymphoma, or a pituitary tumor.

In various embodiments, the present teachings include, without limitation, a compound or a pharmaceutically acceptable salt thereof of structure

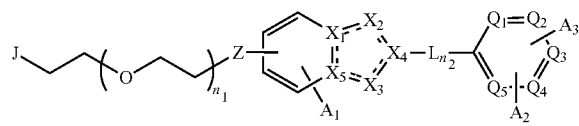

wherein:
J can be selected from the group consisting of a halogen, hydroxy, cyano, $COOR^1$, carboxy, amide, immino, nitro, $NR^2R^3$ and $OR^4$;
$n_1$ can be an integer from 0-4 or an integer from 1-4;
Z can be selected from the group consisting of $CH_2$, O, $NR^5$, S and Se;
each of $A_1$, $A_2$ and $A_3$ can be independently selected from the group consisting of H, F, Cl, Br, I, CN, OH, $NO_2$, $NHR^6$, $NR^7R^8$, $OR^9$, $SR^{10}$, $COOR^{11}$, $COR^{12}$, sulfonic acid,

wherein ⌇ is a bond, 2-ethylidenemalononitrile, (E)-2-(but-2-en-1-ylidene)malononitrile, 2-((2E,4E)-hexa-2,4-dien-1-ylidene)malononitrile, acetyl, —$(OCH_2—CH_2)_{n_4}$— and $R^{13}$; $n_3$ can be an integer from 0-4; $n_4$ can be an integer from 0-4; $X_1$ can be selected from the group consisting of C and N; $X_2$ can be selected from the group consisting of $CH_2$, CH, O, $NR^4$, S, Se and N;
$X_3$ can be selected from the group consisting of $CH_2$, CH, O, $NR^{15}$, S, Se and N;
$X_4$ is C or CH; $X_5$ is C, CH or N; wherein $X_4$ is CH, $X_2$ and $X_4$ are linked by a single bond and $X_3$ and $X_4$ are linked by a single bond, or $X_4$ is C, $X_2$ and $X_4$ are linked by a single bond and $X_3$ and $X_4$ are linked by a double bond, or $X_4$ is C, $X_2$ and $X_4$ are linked by a double bond and $X_3$ and $X_4$ are linked by a single bond; wherein when $X_1$ can be C then $X_5$ and $X_5$ are linked by a double bond; wherein when $X_1$ can be N, then $X_1$ and $X_5$ are linked by a single bond; wherein when $X_2$ can be $NR^{14}$, S, O or Se, then $X_2$ and $X_4$ are linked by a single bond; wherein when $X_2$ can be N, then $X_2$ and $X_4$ are linked by a double bond; wherein when $X_3$ can be $NR^{15}$, S, O or Se, then $X_3$ and $X_4$ are linked by a single bond; wherein when $X_3$ can be N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L can be selected from the group consisting of ($C_1$-$C_4$) alkyl, ($C_3$-$C_6$) cycloalkyl, ($C_2$-$C_8$) alkene (straight or branched), ($C_2$-$C_8$) alkyne,

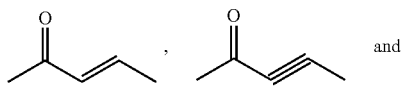

and

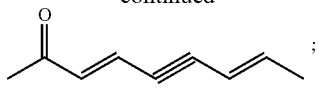

$n_2$ can be an integer from 0-4 or an integer from 1-4; each of $Q_1$, $Q_2$, $Q_3$, $Q_4$ and $Q_5$ can be independently selected from the group consisting of C and N, with provisos that at least two of $Q_1$, $Q_2$, $Q_3$, $Q_4$ and $Q_5$ are C and at least one of $Q_1$, $Q_2$, $Q_3$, $Q_4$ and $Q_5$ is N; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ can be independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl and a combination thereof.

In various aspects of these embodiments, the halogen can be selected from the group consisting of Cl, F, Br and I. In various aspects, the halogen can be selected from the group consisting of $^{18}F$, $^{75}Br$, $^{76}Br$, $^{77}Br$, $^{123}I$, $^{123}I$, $^{125}I$ and $^{131}I$. In various aspects, $R^4$ can be or comprise a radionuclide such as a $^{11}C$. In various aspects, $R^{13}$ can be or comprise a radionuclide such as a $^{11}C$.

In various embodiments, the present teachings include, without limitation, a compound or a pharmaceutically acceptable salt thereof, of structure

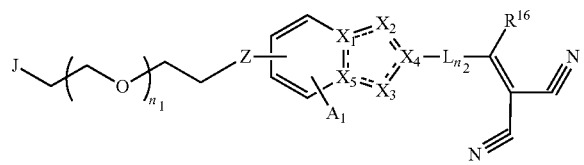

J can be selected from the group consisting of a halogen (Cl, F, Br, I), a radionuclide (such as $^{18}F$, $^{75}Br$, $^{76}Br$, $^{77}Br$, $^{123}I$, $^{124}I$, $^{125}I$, $^{131}I$), hydroxy, cyano, $COOR^1$, carboxy, amide, immino, nitro, $NR^2R^3$ and $OR^4$ (with a radionuclide, such as $^{11}C$ or an unlabeled counterpart); $n_1$ can be an integer from 0-4 or an integer from 1-4; Z can be selected from the group consisting of $CH_2$, O, $NR^5$, S and Se; $A_1$ can be selected from the group consisting of H, F, Cl, Br, I, CN, OH, $NO_2$, $NHR^6$, $NR^7R^8$, $OR^9$, $SR^{10}$, $COOR^{11}$, $COR^{12}$, sulfonic acid,

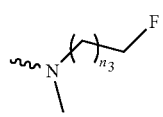

wherein ⌇ is a bond, 2-ethylidenemalononitrile, (E)-2-(but-2-en-1-ylidene)malononitrile, 2-((2E,4E)-hexa-2,4-dien-1-ylidene)malononitrile, acetyl, —$(OCH_2—CH_2)_{n_4}$—$(CH_2)_2$-J, and $R^{13}$ (including radionuclide); $n_3$ can be an integer from 0-4; $n_4$ can be an integer from 0-4;

$X_1$ can be selected from the group consisting of C and N; $X_2$ can be selected from the group consisting of $CH_2$, CH, O, $NR^{14}$, S, Se and N; $X_3$ can be selected from the group consisting of $CH_2$, CH, O, $NR^{15}$, S, Se and N; wherein when $X_2$ is $NR^{14}$, S, O or Se, then $X_2$ and $X_4$ are linked by a single bond; wherein when $X_2$ is N, then $X_2$ and $X_4$ are linked by a double bond;
wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L can be selected from the group consisting of aryl, $(C_1-C_4)$ alkyl, $(C_3-C_6)$ cycloalkyl, $(C_2-C_8)$ alkene (straight or branched), $(C_2-C_8)$ alkyne,

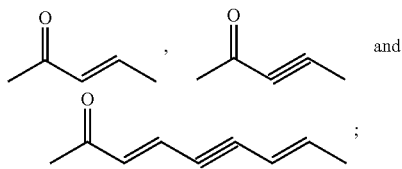

$n_2$ can be an integer from 0-4 or 1-4; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ can be independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne, $C_{3-7}$ cycloalkyl aryl and a combination thereof.

In various aspects, a compound or a pharmaceutically acceptable salt thereof of these embodiments, the halogen can be selected from the group consisting of Cl, F, Br and I, or selected from the group consisting of $^{18}F$, $^{75}Br$, $^{76}Br$, $^{77}Br$, $^{123}I$, $^{124}I$, $^{125}I$ and $^{131}I$. In some aspects, $R^4$ can be or can comprise a radionuclide such as, without limitation, a $^{11}C$. In some aspects, $R^{13}$ can be or can comprise a radionuclide such as, without limitation, a $^{11}C$.

In various embodiments, the present teachings include, without limitation, a compound or a pharmaceutically acceptable salt thereof, of structure

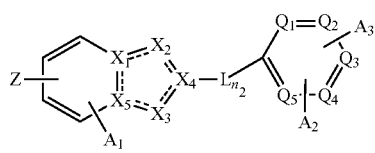

wherein: Z can be selected from the group consisting of $CH_2$, O, $NR^1$, S, Se and

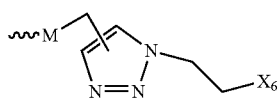

wherein ∿∿∿ is a bond; each of $A_1$, $A_2$ and $A_3$ can be independently selected from the group consisting of H, F, Cl, Br, I, CN, OH, $NO_2$, $NHR^2$, $NR^3R^4$, OR, $SR^6$, $COOR^7$, $COR^8$, sulfonic acid,

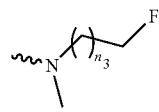

wherein ∿∿ is a bond, 2-ethylidenemalononitrile, (E)-2-(but-2-en-1-ylidene)malononitrile, 2-((2E,4E)-hexa-2,4-dien-1-ylidene)malononitrile, acetyl, $—(OCH_2—CH_2)_{n4}$ and $R^9$ (including radionuclide); $n_3$ can be an integer from 0-4; $n_4$ can be an integer from 0-4; $X_1$ can be selected from the group consisting of C and $N^+$; $X_2$ can be selected from the group consisting of $CH_2$, CH, O, $NR^{10}$, S, Se and N; $X_3$ can be selected from the group consisting of $CH_2$, CH, O, $NR^{11}$, S, Se and N; wherein when $X_2$ is $NR^{14}$, S, O or Se, then $X_2$ and $X_4$ are linked by a single bond; wherein when $X_2$ is N, then $X_2$ and $X_4$ are linked by a double bond; wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L can be selected from the group consisting of $(C_1-C_4)$ alkyl, $(C_3-C_6)$ cycloalkyl, $(C_2-C_8)$ alkene (straight or branched), $(C_2-C_8)$ alkyne,

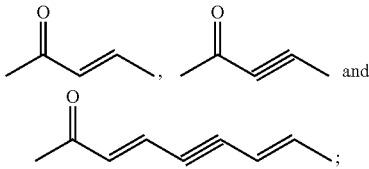

$n_2$ can be an integer from 0-4 or an integer from 1-4; each of $Q_1$, $Q_2$, $Q_3$, $Q_4$ and $Q_5$ can be independently selected from the group consisting of C and N, with provisos that at least two of $Q_1$, $Q_2$, $Q_3$, $Q_4$ and $Q_5$ are C and at least one of $Q_1$, $Q_2$, $Q_3$, $Q_4$ and $Q_5$ is N; M=O, S, Se, $NR^{12}$, amide, maleimide, urea, haloalkane, haloalkene, or haloalkyne; $X_6$=Halogen, $NH_2$; $NHR^{13}$ ($R^{13}$=methyl, ethyl, propyl, or any alkyl straight or branched chain); $OR^{14}$, $COOR^{15}$, $COR^{16}$, OH, NHQ (Q=Chelator Core (NOTA, DOTA, DTPA, or Triglycine) for chelation of metal radionuclide, such as an ion of gallium-67 ($^{67}Ga$), gallium-68 ($^{68}Ga$), an unlabeled gallium, or a paramagnetic metal which includes an ion of $^{67}Ga$, an ion of $^{68}Ga$, an ion of an unlabeled gallium, -indium-111 ($^{111}In$), -iron-52 ($^{52}Fe$), iron-59 ($^{59}Fe$), -copper-62 ($^{62}Cu$), -copper-64 ($^{64}Cu$), -thallium-201 ($^{201}Tl$), -technetium-99m ($^{99m}Tc$), -technetium-94m ($^{94m}Tc$), -rhenium-188 ($^{188}Re$), -rubidium-82 ($^{82}Rb$), -strontium-92 ($^{92}Sr$), -yttrium-86 ($^{86}Y$) or yttrium-90 ($^{90}Y$), -zirconium-86 ($^{86}Zr$) or zirconium-89 ($^{89}Zr$), and a paramagnetic metal ion such as, a transition metal (exemplified by iron, manganese, and a cobalt), or a lanthanide metal ion, such as gadolinium); each of $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$ and $R^{16}$ can be independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl. In some aspects of these embodiments, the halogen can be selected from the group consisting of Cl, F, Br and I.

In some aspects of these embodiments, the halogen can be selected from the group consisting of $^{18}F$, $^{75}Br$, $^{76}Br$, $^{77}Br$, $^{123}I$, $^{124}I$, $^{125}I$ and $^{131}I$. In some aspects, $R^4$ can be or can comprise a radionuclide, such as, without limitation, a $^{11}C$.

In some aspects, $R^{13}$ can be or can comprise a radionuclide, such as, without limitation, a $^{11}C$.

In some aspects of these embodiments, a compound or a pharmaceutically acceptable salt thereof can comprise a chelator core selected from the group consisting of NOTA

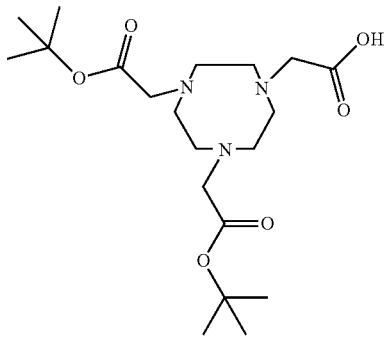

DOTA (1,4,7,10-tetraazacyclododecane-1,4,7,10-tetraacetic acid), DTPA (Diethylenetriaminepentaacetic acid) and triglycine. In some aspects, a chelator core can chelate a metal radionuclide. In some aspects, metal radionuclide can be an ion selected from the group consisting of an ion of gallium-67 and an ion of gallium-68. In some aspects the ion can be selected from the group consisting of an ion of gallium-67, an ion of gallium-68, an ion of an unlabeled gallium, an ion of indium-111, an ion of iron-52, an ion of iron-59, an ion of copper-62, an ion of copper-64, an ion of thallium-201, an ion of technetium-99m, an ion of technetium-94m, an ion of rhenium-188, an ion of rubidium-82, an ion of strontium-92, an ion of yttrium-86, an ion of yttrium-90, an ion of zirconium-86, an ion of zirconium-89. In some aspects, the ion can be a paramagnetic metal ion. In some aspects, the ion can be selected from the group consisting of an ion of iron, an ion of manganese and an ion of cobalt. In some aspects, the ion can be a lanthanide metal ion. In some aspects, the ion can be a gadolinium ion.

In various embodiments, the present teachings include, without limitation, a compound or a pharmaceutically acceptable salt thereof, of structure

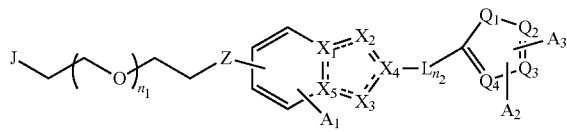

wherein:

J can be selected from the group consisting of a halogen, such as Cl, F, Br, or I, or a radionuclide (such as $^{18}F$, $^{75}Br$, $^{76}Br$, $^{77}Br$, $^{123}I$, $^{124}I$, $^{125}I$, $^{131}$), hydroxy, cyano, $COOR^1$, carboxy, amide, immino, nitro, $NR^2R^3$ and $OR^4$ (with a radionuclide, such as $^{11}C$ or an unlabeled counterpart);

$n_1$ can be an integer from 0-4 or an integer from 1-4; Z can be selected from the group consisting of $CH_2$, O, $NR^5$, S and Se; each of $A_1$, $A_2$ and $A_3$ can be independently selected from the group consisting of H, F, Cl, Br, I, CN, OH, $NO_2$, $NHR^6$, $NR^7R^8$, $OR^9$, $SR^{10}$, $COOR^{11}$, $COR^{12}$, sulfonic acid,

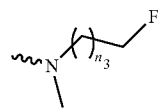

wherein ⌇ is a bond, 2-ethylidenemalononitrile, (E)-2-(but-2-en-1-ylidene)malononitrile, 2-((2E,4E)-hexa-2,4-dien-1-ylidene)malononitrile, acetyl, $-(OCH-CH_2)_{n_4}-(CH_2)_2$-J, and $R^{13}$ (including radionuclide); $n_3$ can be an integer from 0-4; $n_4$ can be an integer from 0-4; $X_1$ can be selected from the group consisting of C and N; $X_2$ can be selected from the group consisting of $CH_2$, CH, O, $NR^{14}$, S, Se and N; $X_3$ can be selected from the group consisting of $CH_2$, CH, O, $NR^{15}$, S, Se and N; wherein when $X_2$ is $NR^{14}$, S, O or Se, then $X_2$ and $X_4$ are linked by a single bond; wherein when $X_2$ is N, then $X_2$ and $X_4$ are linked by a double bond; wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L can be selected from the group consisting of $(C_1-C_4)$ alkyl, $(C_3-C_6)$ cycloalkyl, $(C_2-C_8)$ alkene (straight or branched), $(C_2-C_8)$ alkyne,

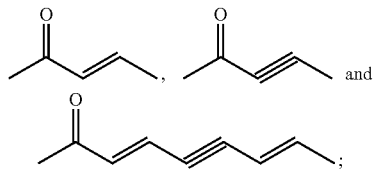

$n_2$ can be an integer from 0-4 or an integer from 1-4; each of $Q_1$, $Q_2$, $Q_3$ and $Q_4$ can be independently selected from the group consisting of C and N, with provisos that at least two of $Q_1$, $Q_2$, $Q_3$ and $Q_4$ are C and at least one of $Q_1$, $Q_2$, $Q_3$ and $Q_4$ is N; each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ can be independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl, or a combination thereof.

In various aspects, a compound or a pharmaceutically acceptable salt thereof of these embodiments can comprise a halogen that is selected from the group consisting of Cl, F, Br and I. In various aspects, the halogen can be selected from the group consisting of $^{18}F$, $^{75}Br$, $^{76}Br$, $^{77}Br$, $^{123}I$, $^{124}I$, $^{125}I$ and $^{131}I$. In various aspects, $R^4$ can be or can comprise a radionuclide, such as, without limitation, a $^{11}C$. In various aspects, $R^{13}$ can be or can comprise a radionuclide, such as, without limitation, a $^{11}C$.

In various embodiments, the present teachings include, without limitation, a pharmaceutically acceptable salt thereof, of structure

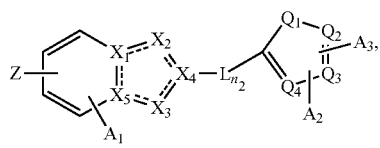

wherein: Z can be selected from the group consisting of CH$_2$, O, NR$^1$, S, Se and

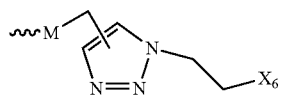

wherein ∿∿∿ is a bond; each of A$_1$, A$_2$ and A$_3$ can be independently selected from the group consisting of H, F, Cl, Br, I, CN, OH, NO$_2$, NHR$^2$, NR$^3$R$^4$, OR$^5$, SR$^6$, COOR$^7$, COR$^8$, sulfonic acid,

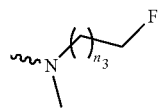

wherein ∿∿ is a bond, 2-ethylidenemalononitrile, (E)-2-(but-2-en-1-ylidene)malononitrile, 2-((2E,4E)-hexa-2,4-dien-1-ylidene)malononitrile, acetyl-(OCH$_2$—CH$_2$)$_{n_4}$—(CH$_2$)$_2$-J and R$^9$ (including radionuclide); n; can be an integer from 0-4; n$_4$ can be an integer from 0-4; X$_1$ can be selected from the group consisting of C and N; X$_2$ can be selected from the group consisting of CH$_2$, CH, O, NR$^{10}$, S, Se and N; X$_3$ can be selected from the group consisting of CH$_2$, CH, O, NR$^{11}$, S, Se and N; when X$_2$ is NR$^{14}$, S, O or Se, then X$_2$ and X$_4$ are linked by a single bond; when X$_2$ is N, then X$_2$ and X$_4$ are linked by a double bond; wherein when X$_3$ is NR$^{15}$, S, O or Se, then X$_3$ and X$_4$ are linked by a single bond; wherein when X$_3$ is N, then X$_1$ and X$_4$ are linked by a double bond; wherein when both the X$_2$ and X$_5$ are N, then X$_1$ and X$_2$ are linked by a double bond, X$_2$ and X$_4$ are linked by a single bond, X$_3$ and X$_4$ are linked by a double bond, and X$_3$ and X$_5$ are linked by a single bond; wherein when both the X$_1$ and X$_2$ are N, then X$_2$ and X$_4$ are linked by a double bond, X$_3$ and X$_4$ are linked by a single bond, X$_3$ and X$_5$ are linked by a double bond, and X$_1$ and X$_5$ are linked by a single bond; L can be selected from the group consisting of (C$_1$-C$_4$) alkyl, (C$_3$-C$_6$) cycloalkyl, (C$_2$-C$_8$) alkene (straight or branched), (C$_2$-C$_8$) alkyne,

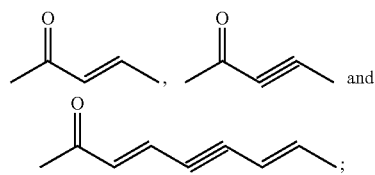

n$_2$ can be an integer from 0-4 or an integer from 1-4; each of Q$_1$, Q$_2$, Q$_3$, Q$_4$ and Q$_5$ can be independently selected from the group consisting of C and N, with provisos that at least two of Q$_1$, Q$_2$, Q$_3$ and Q$_4$ are C and at least one of Q$_1$, Q$_2$, Q$_3$ and Q$_4$ is N; M can be O, S, Se, NR$^{12}$, amide, maleimide, urea, haloalkane, haloalkene or haloalkyne;

X$_6$ can be a halogen, NH$_2$, NHR$^{13}$; R$^{13}$ can be methyl, ethyl, propyl, or any alkyl straight or branched chain; OR$^{14}$, COOR$^{15}$, COR$^{16}$, OH, NHQ, wherein Q is a chelator core such as NOTA, DOTA, DTPA, Triglycine for chelation of metal radionuclide, which can be, without limitation, an ion of gallium-67, gallium-68, an unlabeled gallium, or a paramagnetic metal which includes an ion of gallium-67, an ion of gallium-68, an ion of an unlabeled gallium, or an ion of indium-111, an ion of iron-52, an ion of iron-59, an ion of copper-62, an ion of copper-64, an ion of thallium-201, an ion of technetium-99m, an ion of technetium-94m, an ion of rhenium-188, an ion of rubidium-82, an ion of strontium-92, an ion of yttrium-86 or an ion of yttrium-90, an ion of zirconium-86, an ion of zirconium-89, and a paramagnetic metal ion such as, a transition metal (such as, without limitation, an ion of iron, an ion of manganese, or an ion of cobalt), or a lanthanide metal ion, such as an ion of gadolinium; each of R$^1$, R$^2$, R$^3$, R$^4$, R$^5$, R$^6$, R$^7$, R$^8$, R$^9$, R$^{10}$, R$^{11}$, R$^{12}$, R$^{14}$, R$^{15}$ and R$^{16}$ can be independently selected from the group consisting of H, C$_{1-12}$ linear alkyl, C$_{2-12}$ linear alkene, C$_{2-12}$ linear alkyne, C$_{3-12}$ branched chain alkyl, C$_{3-12}$ branched chain alkene, C$_{3-12}$ branched chain alkyne and C$_{3-7}$ cycloalkyl aryl.

In various aspects of these embodiments, a compound or a pharmaceutically acceptable salt thereof can comprise a halogen that can be selected from the group consisting of Cl, F, Br and I, or can be selected from the group consisting of $^{18}$F, $^{75}$Br, $^{76}$Br, $^{77}$Br, $^{123}$I, $^{124}$I, $^{125}$I and $^{131}$I. In some aspects, R$^4$ can comprise a radionuclide such as, without limitation, a $^{11}$C. In some aspects, R$^{13}$ can comprise a radionuclide such as, without limitation, a $^{11}$C. In various aspects, a compound or a pharmaceutically acceptable salt can comprise a chelator core that can be selected from the group consisting of NOTA, DOTA, DTPA and triglycine. In some aspects, a chelator core of these aspects can chelate a metal radionuclide, which can be, without limitation, an ion of $^{67}$Ga or an ion of $^{68}$Ga. In some aspects, a chelator core of these embodiments can chelate a metal radionuclide, which can be, without limitation, an ion selected from the group consisting of an ion of gallium-67, an ion of gallium-68, an ion of an unlabeled gallium, an ion of indium-111, an ion of iron-52, an ion of iron-59, an ion of copper-62, an ion of copper-64, an ion of thallium-201, an ion of technetium-99m, an ion of technetium-94m, an ion of rhenium-188, an ion of rubidium-82, an ion of strontium-92, an ion of yttrium-86, an ion of yttrium-90, an ion of zirconium-86, an ion of zirconium-89. In some aspects, the ion can be a paramagnetic metal ion. In some aspects, the ion can be selected from the group consisting of an ion of iron, an ion of manganese and an ion of cobalt. In some aspects, the ion can be a lanthanide metal ion. In some aspects, the ion can be a gadolinium ion.

In some embodiments, the present teachings include gold nanoparticles which comprise gold conjugated to a compound described herein.

In some embodiments, the present teachings include complexes, wherein a complex comprises a compound or a pharmaceutically acceptable salt thereof described herein, and a gold nanoparticle.

In some embodiments, the present teachings include a gold nanoparticle conjugated to a compound disclosed herein. In some configurations, a gold nanoparticle of the present teachings can further comprise a linker, such as, without limitation, an aminothiol (Abbas, A., et al., *Langmuir* 2013, 29, 56-64). In various configurations, the aminothiol can be an aminothiophenol. In some configurations, the aminothiophenol can be a p-aminothiophenol. In various aspects, the gold of a gold nanoparticle can be Au-199 and/or Au-198.

In various embodiments, the present teachings include methods of imaging distribution of amyloid beta in a sample or a subject. In various configurations, these methods can comprise: administering a compound, a pharmaceutically acceptable salt thereof or a gold nanoparticle disclosed herein to the sample or subject wherein the compound pharmaceutically acceptable salt thereof or gold nanoparticle comprises a radionuclide, and subjecting the sample or subject to PET scanning or SPECT scanning. In various configurations, these methods can comprise administering a compound, a pharmaceutically acceptable salt thereof, or a gold nanoparticle disclosed herein to the sample or subject, and applying to the sample or subject electromagnetic radiation visible and/or UV light of wavelength(s) that is/are excitatory for fluorescence of the compound, salt thereof or gold nanoparticle. The methods further include detecting light emitted by fluorescence of the compound, salt thereof or gold nanoparticle by known methods, such as, without limitation, fluorescence microscopy.

In some embodiments, the present teachings include methods of imaging cardiac systemic amyloidosis in a subject. In various configurations, these methods comprise administering an imaging effective amount of a compound, a pharmaceutically acceptable salt thereof or a gold nanoparticle of the present teachings to the subject, and subjecting the subject to PET or SPECT scanning, or fluorescence imaging.

In some embodiments, the present teachings include methods of inhibiting amyloid beta aggregation. In various aspects, these methods can comprise administering an effective amount of a compound, a pharmaceutically acceptable salt thereof or a gold nanoparticle of the present teachings, wherein the compound or salt thereof comprises at least one Se atom.

In some embodiments, the present teachings include methods of inhibiting diagnosing or monitoring progression of Alzheimer's disease. In various aspects, these methods comprise administering to a subject a compound, a pharmaceutically acceptable salt thereof or a gold nanoparticle of the present teachings, and subjecting the subject to PET or SPECT scanning, or to fluorescence imaging.

In some embodiments, the present teachings include methods of diagnosing or monitoring progression of a neurodegenerative disease. In various aspects, these methods comprise administering to a subject a compound, a pharmaceutically acceptable salt thereof or a gold nanoparticle of the present teachings, and subjecting the subject to PET or SPECT scanning, or to fluorescence imaging.

In some embodiments, the present teachings include methods of diagnosing or monitoring progression of cardiac systemic amyloidosis. In various configurations, these methods include administering to a subject a compound, a pharmaceutically acceptable salt thereof or a gold nanoparticle of the present teachings, and subjecting the subject to PET or SPECT scanning, or to fluorescence imaging.

In some embodiments, the present teachings include methods for detecting or ruling out a meningioma in a subject. In some configurations, these methods can include administering to a subject a compound, a pharmaceutically acceptable salt thereof or a gold nanoparticle of the present teachings. In various aspects, the compound can be targeted to any type of meningioma in the patient. An image can be acquired to detect the presence or absence of any meningioma inside the skull or elsewhere within the patient. In some aspects, the methods can include a step of acquiring the image, which can be performed using an imaging method selected from PET or SPECT scanning with concurrent computed tomography (CT) imaging or magnetic resonance imaging (MRI), SPECT scanning with concurrent computed tomographic imaging, fluorescence imaging, or any combination thereof.

In some embodiments, the present teachings include methods for differentiating the presence of meningiomas from other tumors types via retention of greater activity of a compound, a pharmaceutically acceptable salt thereof or a gold nanoparticle of the present teachings in meningiomas compared with other intracranial tumors, such as pituitary macroadenomas, schwannomas or ependymomas, and metastases.

In some embodiments, the present teachings include a compound of structure

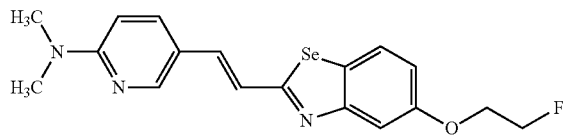 [SMILES: CN(C)c1ccc(/C=C/c2nc3cc(OCCF)ccc3[se]2)cn1]

(F-AI-183) or a pharmaceutically acceptable salt thereof.

In some embodiments, the present teachings include a compound of structure

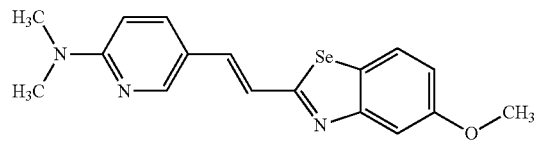

or a pharmaceutically acceptable salt thereof.

In some embodiments, the present teachings include a compound of structure

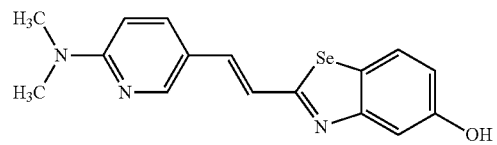 [SMILES: CN(C)c1ccc(/C=C/c2nc3cc(O)ccc3[se]2)cn1]

or a pharmaceutically acceptable salt thereof.

In some embodiments, the present teachings include a compound of structure

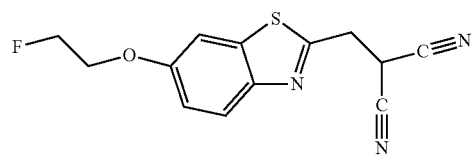 [SMILES: N#CC(C#N)Cc1nc2ccc(OCCF)cc2s1]

or a pharmaceutically acceptable salt thereof.

In some embodiments, the present teachings include a compound of structure

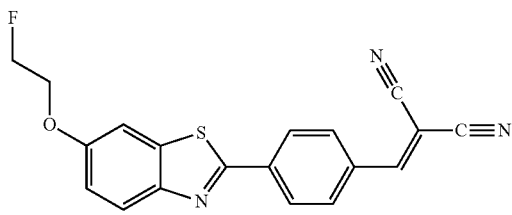 [SMILES: N#CC(C#N)=Cc1ccc(-c2nc3ccc(OCCF)cc3s2)cc1]

or a pharmaceutically acceptable salt thereof.

In some embodiments, the present teachings include a compound of structure

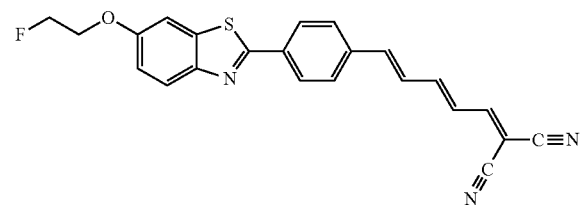 [SMILES: N#CC(C#N)=C/C=C/C=C/c1ccc(-c2nc3ccc(OCCF)cc3s2)cc1]

or a pharmaceutically acceptable salt thereof.

In some embodiments, the present teachings include a compound of structure

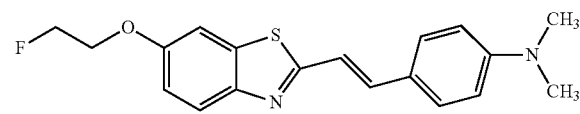

or a pharmaceutically acceptable salt thereof.

In some embodiments, the present teachings include a compound of structure

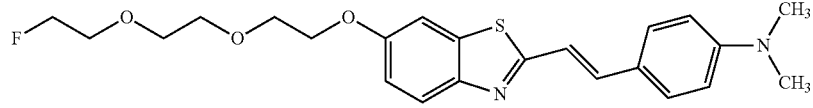 [SMILES: CN(C)c1ccc(/C=C/c2nc3ccc(OCCOCCOCCF)cc3s2)cc1]

or a pharmaceutically acceptable salt thereof.

In some embodiments, the present teachings include a compound of structure

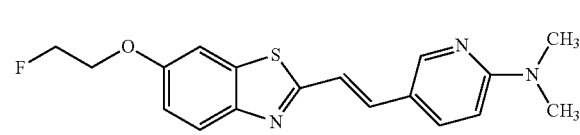

(AI-182) or a pharmaceutically acceptable salt thereof.

In some embodiments, the present teachings include a compound of structure

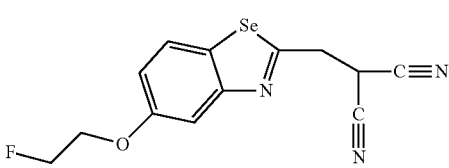 [SMILES: N#CC(C#N)Cc1nc2cc(OCCF)ccc2[se]1]

or a pharmaceutically acceptable salt thereof.

In some embodiments, the present teachings include a compound of structure

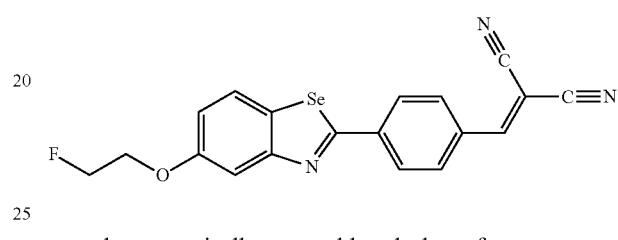

or a pharmaceutically acceptable salt thereof.

In some embodiments, the present teachings include a compound of structure

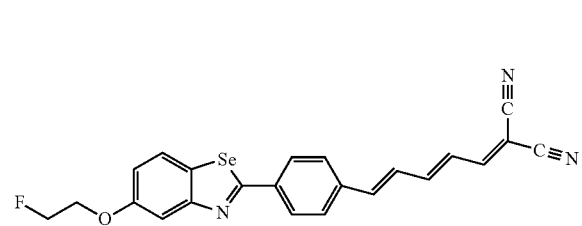 [SMILES: N#CC(C#N)=C/C=C/C=C/c1ccc(-c2nc3cc(OCCF)ccc3[se]2)cc1]

or a pharmaceutically acceptable salt thereof.

In some embodiments, the present teachings include a compound of structure

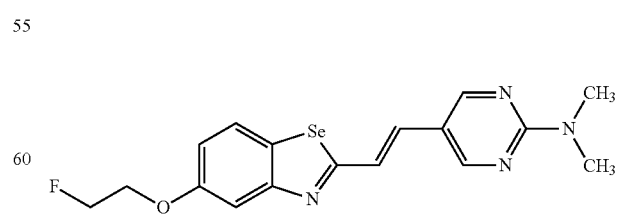

or a pharmaceutically acceptable salt thereof.

In some embodiments, the present teachings include a compound of structure

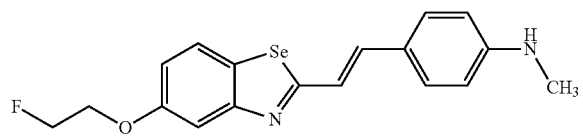 [SMILES: CNc1ccc(/C=C/c2nc3cc(OCCF)ccc3[se]2)cc1]

or a pharmaceutically acceptable salt thereof.

In some embodiments, the present teachings include a compound of structure

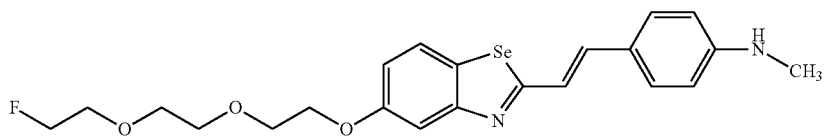 [SMILES: CNc1ccc(/C=C/c2nc3cc(OCCOCCOCCF)ccc3[se]2)cc1]

or a pharmaceutically acceptable salt thereof.

In some embodiments, the present teachings include a compound of structure

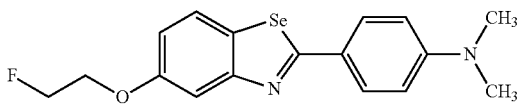 [SMILES: CN(C)c1ccc(-c2nc3cc(OCCF)ccc3[se]2)cc1]

or a pharmaceutically acceptable salt thereof.

In some embodiments, the present teachings include a compound of structure

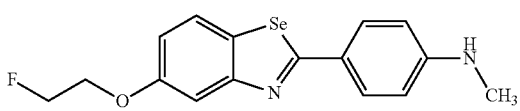 [SMILES: CNc1ccc(-c2nc3cc(OCCF)ccc3[se]2)cc1]

or a pharmaceutically acceptable salt thereof.

In some embodiments, the present teachings include a compound of structure

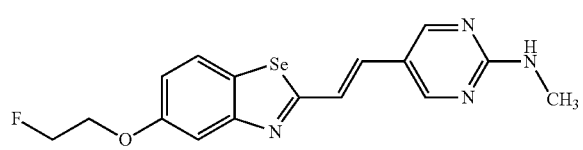 [SMILES: CNc1ncc(/C=C/c2nc3cc(OCCF)ccc3[se]2)cn1]

or a pharmaceutically acceptable salt thereof.

In some embodiments, the present teachings include a compound of structure

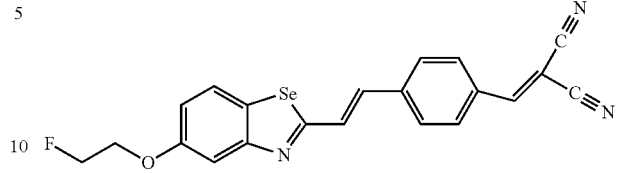

or a pharmaceutically acceptable salt thereof.

In some embodiments, the present teachings include a compound of structure

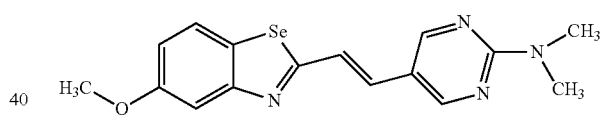

or a pharmaceutically acceptable salt thereof.

In some embodiments, the present teachings include a compound of structure

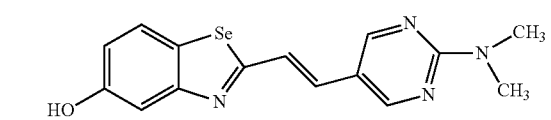 [SMILES: CN(C)c1ncc(/C=C/c2nc3cc(O)ccc3[se]2)cn1]

or a pharmaceutically acceptable salt thereof.

In some embodiments, the present teachings include a compound of structure

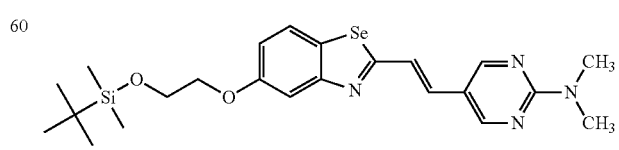

or a pharmaceutically acceptable salt thereof.

In some embodiments, the present teachings include a compound of structure

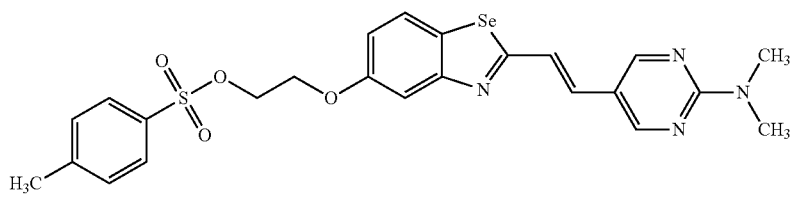

or a pharmaceutically acceptable salt thereof.

In some embodiments, the present teachings include a compound of structure

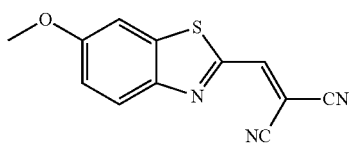 [SMILES: COc1ccc2nc(C=C(C#N)C#N)sc2c1]

or a pharmaceutically acceptable salt thereof.

In some embodiments, the present teachings include a compound of structure

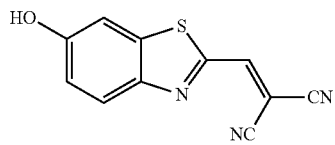 [SMILES: N#CC(C#N)=Cc1nc2ccc(O)cc2s1]

or a pharmaceutically acceptable salt thereof.

In some embodiments, the present teachings include a compound of structure

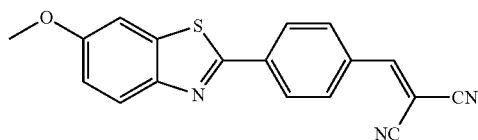 [SMILES: COc1ccc2nc(-c3ccc(C=C(C#N)C#N)cc3)sc2c1]

or a pharmaceutically acceptable salt thereof.

In some embodiments, the present teachings include a compound of structure

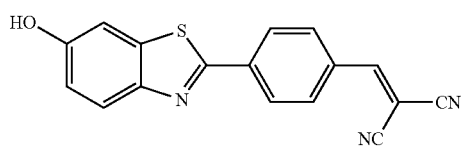 [SMILES: N#CC(C#N)=Cc1ccc(-c2nc3ccc(O)cc3s2)cc1]

or a pharmaceutically acceptable salt thereof.

In some embodiments, the present teachings include a compound of structure

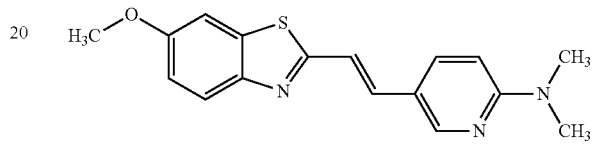

or a pharmaceutically acceptable salt thereof.

In some embodiments, the present teachings include a compound of structure

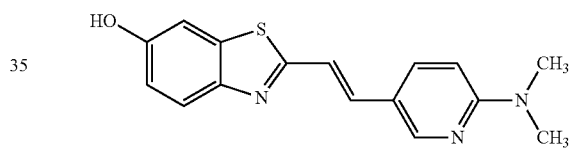

or a pharmaceutically acceptable salt thereof.

In some embodiments, the present teachings include a compound of structure

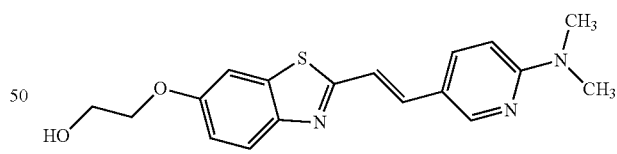

or a pharmaceutically acceptable salt thereof.

In some embodiments, the present teachings include a compound of structure

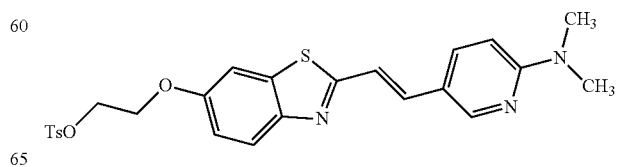

or a pharmaceutically acceptable salt thereof.

The present teachings include, without limitation, the following aspects.

Aspect 1. A compound or a pharmaceutically acceptable salt thereof of structure

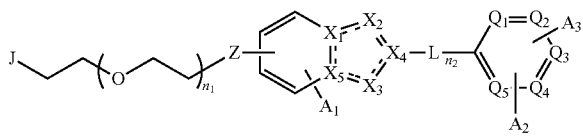

wherein:
J is selected from the group consisting of a halogen, hydroxy, cyano, COOR$^1$, carboxy, amide, immino, nitro, NR$^2$R$^3$ and OR$^4$; $n_1$ is an integer from 0-4; Z is selected from the group consisting of CH$_2$, O, NR$^5$, S and Se; each of A$_1$, A$_2$ and A$_3$ is independently selected from the group consisting of H, F, Cl, Br, I, CN, OH, NO$_2$, NHR$^6$, NR$^7$R$^8$, OR$^9$, SR$^{10}$, COOR$^{11}$, COR$^{12}$, sulfonic acid,

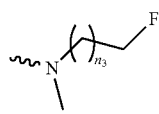

wherein ∿ is a bond, 2-ethylidenemalononitrile, (E)-2-(but-2-en-1-ylidene)malononitrile, 2-((2E,4E)-hexa-2,4-dien-1-ylidene)malononitrile, acetyl, —(OCH$_2$—CH$_2$)$_{n_4}$— and R$^{13}$; $n_3$ is an integer from 0-4; $n_4$ is an integer from 0-4; ⁓ is a single or double bond; X$_1$ is selected from the group consisting of C and N; X$_2$ is selected from the group consisting of CH$_2$, CH, O, NR$^{14}$, S, Se and N; X$_3$ is selected from the group consisting of CH$_2$, CH, O, NR$^{15}$, S, Se and N; X$_4$ is C or CH; X$_5$ is C, CH or N; wherein X$_4$ is CH, X$_2$ and X$_4$ are linked by a single bond and X$_3$ and X$_4$ are linked by a single bond, or X$_4$ is C, X$_2$ and X$_4$ are linked by a single bond and X$_3$ and X$_4$ are linked by a double bond, or X$_4$ is C, X$_2$ and X$_4$ are linked by a double bond and X$_3$ and X$_4$ are linked by a single bond; wherein when X$_1$ is C then X$_1$ and X$_5$ are linked by a double bond; wherein when X$_1$ is N, then X$_1$ and X$_5$ are linked by a single bond; wherein when X$_2$ is NR$^{14}$, S, O or Se, then X$_2$ and X$_4$ are linked by a single bond; wherein when X$_2$ is N, then X$_2$ and X$_4$ are linked by a double bond; wherein when X$_3$ is NR$^{15}$, S, O or Se, then X$_3$ and X$_4$ are linked by a single bond; wherein when X$_3$ is N, then X$_3$ and X$_4$ are linked by a double bond; wherein when both the X$_2$ and X$_5$ are N, then X$_1$ and X$_2$ are linked by a double bond, X$_2$ and X$_4$ are linked by a single bond, X$_3$ and X$_4$ are linked by a double bond, and X$_3$ and X$_5$ are linked by a single bond; wherein when both the X$_1$ and X$_2$ are N, then X$_2$ and X$_4$ are linked by a double bond, X$_1$ and X$_4$ are linked by a single bond, X$_3$ and X$_5$ are linked by a double bond, and X$_1$ and X$_5$ are linked by a single bond; L is selected from the group consisting of (C$_1$-C$_4$) alkyl, (C$_3$-C$_6$) cycloalkyl, (C$_2$-C$_8$) linear alkene, (C$_3$-C$_8$) branched alkene, (C$_2$-C$_8$) alkyne,

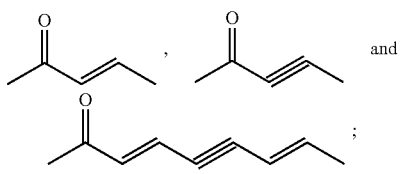

$n_2$ is an integer from 0-4; each of Q$_1$, Q$_2$, Q$_3$, Q$_4$ and Q$_5$ is independently selected from the group consisting of C and N, with provisos that at least two of Q$_1$, Q$_2$, Q$_3$, Q$_4$ and Q$_5$ are C and at least one of Q$_1$, Q$_2$, Q$_3$, Q$_4$ and Q$_5$ is N; and each of R$^1$-R$^{15}$ is independently selected from the group consisting of H, C$_{1-12}$ linear alkyl, C$_{2-12}$ linear alkene, C$_{2-12}$ linear alkyne, C$_{3-12}$ branched chain alkyl, C$_{3-12}$ branched chain alkene, C$_{3-12}$ branched chain alkyne and C$_{3-7}$ cycloalkyl aryl and a combination thereof.

Aspect 2. A compound or a pharmaceutically acceptable salt thereof in accordance with aspect 1, wherein the halogen is selected from the group consisting of Cl, F, Br and I.

Aspect 3. A compound or a pharmaceutically acceptable salt thereof in accordance with aspect 1, wherein the halogen is selected from the group consisting of $^{18}$F, $^{75}$Br, $^{76}$Br, $^{77}$Br, $^{123}$I, $^{124}$I, $^{125}$I and $^{131}$I.

Aspect 4. A compound or a pharmaceutically acceptable salt thereof in accordance with aspect 1, wherein R$^4$ comprises a radionuclide.

Aspect 5. A compound or a pharmaceutically acceptable salt thereof in accordance with aspect 1, wherein R$^4$ comprises a $^{11}$C.

Aspect 6. A compound or a pharmaceutically acceptable salt thereof in accordance with aspect 1, wherein R$^{13}$ comprises a radionuclide.

Aspect 7. A compound or a pharmaceutically acceptable salt thereof in accordance with aspect 1, wherein the compound is

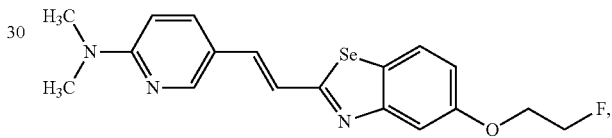

or a pharmaceutically acceptable salt thereof.

Aspect 8. A compound in accordance with aspect 7, wherein the F is $^{18}$F.

Aspect 9. A compound or a pharmaceutically acceptable salt thereof in accordance with aspect 1, wherein the compound is

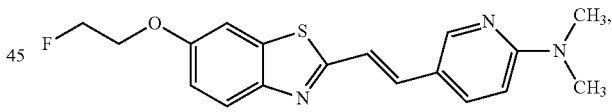

or a pharmaceutically acceptable salt thereof.

Aspect 10. A compound in accordance with aspect 9, wherein the F is $^{18}$F.

Aspect 11. A compound or a pharmaceutically acceptable salt thereof in accordance with aspect 1, wherein the compound is selected from the group consisting of

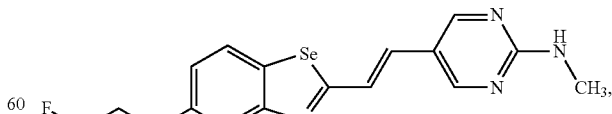

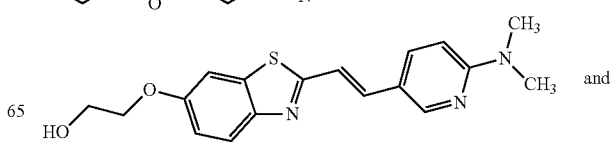

and or a pharmaceutically acceptable salt thereof.

Aspect 12. A compound or a pharmaceutically acceptable salt thereof in accordance with aspect 1, wherein the compound is selected from the group consisting of or a pharmaceutically acceptable salt thereof, wherein the F is $^{18}$F.

Aspect 13. A complex comprising:
a compound or a pharmaceutically acceptable salt thereof in accordance with aspect 1; and
a gold nanoparticle.

Aspect 14. A gold nanoparticle conjugated to a compound in accordance with aspect 1.

Aspect 15. A method of imaging distribution of amyloid beta in a sample or a subject, comprising:
administering a compound or a pharmaceutically acceptable salt thereof in accordance with aspect 1 to the sample or subject wherein the compound or pharmaceutically acceptable salt thereof comprises a radionuclide;
subjecting the sample or subject to PET or SPECT scanning.

Aspect 16. A method of imaging cardiac systemic amyloidosis in a subject, comprising administering an imaging effective amount of a compound or a pharmaceutically acceptable salt thereof in accordance with aspect 1 to the subject, and subjecting the subject to PET or SPECT scanning.

Aspect 17. A method of inhibiting amyloid beta aggregation, comprising administering a compound or a pharmaceutically acceptable salt thereof of aspect 1, wherein at least one of Z, $X_2$ and $X_3$ is Se.

Aspect 18. A method for detecting or ruling out a meningioma in a subject, comprising administering to a subject a compound or a pharmaceutically acceptable salt thereof in accordance with aspect 1.

Aspect 19. A method for detecting or ruling out a meningioma in a subject in accordance with aspect 18, wherein the detecting comprises PET or SPECT scanning with concurrent computed tomography (CT) imaging, magnetic resonance imaging (MRI), or a combination thereof.

Aspect 20. A method for differentiating the presence of a meningioma from other tumors types in a subject, comprising:
administering to a subject a diagnostically acceptable amount of a compound or a pharmaceutically acceptable salt thereof in accordance with aspect 1;
detecting retention of the compound,
wherein greater activity of the compound compared to a control is diagnostic for meningioma.

Aspect 21. A compound or a pharmaceutically acceptable salt thereof, of structure wherein: J is selected from the group consisting of a halogen, hydroxy, cyano, COOR$^1$, carboxy, amide, immino, nitro, NR$^2$R$^3$ and OR$^4$; $n_1$ is an integer from 0-4; Z is selected from the group consisting of CH$_2$, O, NR$^5$, S and Se; A$_1$ is selected from the group consisting of H, F, Cl, Br, I, CN, OH, NO$_2$, NHR$^6$, NR$^7$R$^8$, OR$^9$, SR$^{10}$, COOR$^{11}$, COR$^{12}$, sulfonic acid, wherein ⌇ is a bond, 2-ethylidenemalononitrile, (E)-2-(but-2-en-1-ylidene)malononitrile, 2-((2E,4E)-hexa-2,4-dien-1-ylidene)malononitrile, acetyl, (OCH$_2$—CH$_2$)$_{n_4}$—(CH$_2$)$_2$ and R$^{13}$; $n_3$ is an integer from 0-4; $n_4$ is an integer from 0-4; ⋯ is a single or double bond; $X_1$ is selected from the group consisting of C and N; $X_2$ is selected from the group consisting of CH$_2$, CH, O, NR$^{14}$, S, Se and N; $X_3$ is selected from the group consisting of CH$_2$, CH, O, NR$^1$, S, Se and N; $X_4$ is selected from the group consisting of C and CH; $X_5$ is selected from the group consisting of N, C and CH; wherein when $X_2$ is NR$^{14}$, S, O or Se, then $X_2$ and $X_4$ are linked by a single bond, wherein when $X_2$ is N, then $X_2$ and $X_4$ are linked by a double bond; wherein when $X_1$ is NR$^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L is selected from the group consisting of aryl, (C$_1$-C$_4$) alkyl, (C$_3$-C$_6$) cycloalkyl, (C$_2$-C$_8$) straight alkene, (C$_3$-C$_8$) branched alkene, (C$_2$-C$_8$) alkyne, $n_2$ is an integer from 0-4; and each of $R^1$-$R^{16}$ is independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl, or a combination thereof.

Aspect 22. A compound or a pharmaceutically acceptable salt thereof in accordance with aspect 21, wherein the halogen is selected from the group consisting of Cl, F, Br and I.

Aspect 23. A compound or a pharmaceutically acceptable salt thereof in accordance with aspect 21, wherein the halogen is selected from the group consisting of $^{18}$F, $^{75}$Br, $^{76}$Br, $^{77}$Br, $^{123}$I, $^{124}$I, $^{125}$I and $^{131}$I.

Aspect 24. A compound or a pharmaceutically acceptable salt thereof in accordance with aspect 21, wherein $R^4$ comprises a radionuclide.

Aspect 25. A compound or a pharmaceutically acceptable salt thereof in accordance with aspect 21, wherein $R^4$ comprises a $^{11}$C.

Aspect 26. A compound or a pharmaceutically acceptable salt thereof in accordance with aspect 21, wherein $R^{13}$ comprises a radionuclide.

Aspect 27. A compound or a pharmaceutically acceptable salt thereof, of structure

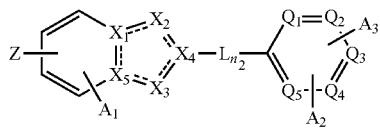

wherein: Z is selected from the group consisting of $CH_2$, O, $NR^1$, S, Se and

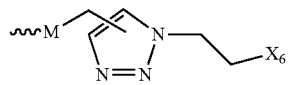

wherein $\sim\!\sim\!\sim$ is a bond; each of $A_1$, $A_2$ and $A_3$ is independently selected from the group consisting of H, F, Cl, Br, I, CN, OH, $NO_2$, $NHR^2$, $NR^3R^4$, $OR^5$, $SR^6$, $COOR^7$, $COR^8$, sulfonic acid,

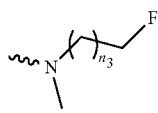

wherein $\sim\!\sim$ is a bond, 2-ethylidenemalononitrile, (E)-2-(but-2-en-1-ylidene)malononitrile, 2-((2E,4E)-hexa-2,4-dien-1-ylidene)malononitrile, acetyl, —$(OCH_2—CH_2)_{n_4}$ and $R^9$; $n_3$ is an integer from 0-4; $n_4$ is an integer from 0-4; $X_1$ is selected from the group consisting of C and $N^+$; $X_2$ is selected from the group consisting of $CH_2$, CH, O, $NR^{10}$, S, Se and N; $X_3$ is selected from the group consisting of $CH_2$, CH, O, $NR^{11}$, S, Se and N; $X_4$ is selected from the group consisting of C and CH; $X_5$ is selected from the group consisting of N, C and CH; wherein when $X_2$ is $NR^{14}$, S, O or Se, then $X_2$ and $X_4$ are linked by a single bond; wherein when $X_2$ is N, then $X_2$ and $X_4$ are linked by a double bond; wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_5$ and $X_5$ are linked by a double bond, and $X_1$ and $X_5$ are linked by a single bond; L is selected from the group consisting of $(C_1$-$C_4)$ alkyl, $(C_3$-$C_6)$ cycloalkyl, $(C_2$-$C_8)$ straight alkene, $(C_3$-$C_8)$ branched alkene, $(C_2$-$C_8)$ alkyne,

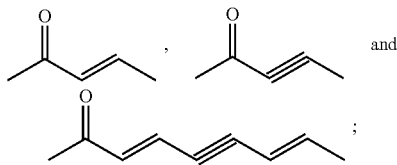

$n_2$ is an integer from 1-4; each of $Q_1$, $Q_2$, $Q_3$, $Q_4$ and $Q_5$ is independently selected from the group consisting of C and N, with provisos that at least two of $Q_1$, $Q_2$, $Q_3$, $Q_4$ and $Q_5$ are C and at least one of $Q_1$, $Q_2$, $Q_3$, $Q_4$ and $Q_5$ is N; M is selected from the group consisting of O, S, Se, $NR^{12}$, amide, maleimide, urea, haloalkane, haloalkene and haloalkyne; $X_6$ is a halogen, $NH_2$, $NHR^{13}$ $OR^{14}$, $COOR^{15}$, $COR^{16}$, OH, NHQ wherein Q is a chelator core; each of $R^1$-$R^{12}$ and $R^{14}$-$R^{16}$ is independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl.

Aspect 28. A compound or a pharmaceutically acceptable salt thereof in accordance with aspect 41, wherein the halogen is selected from the group consisting of Cl, F, Br and I.

Aspect 29. A compound or a pharmaceutically acceptable salt thereof in accordance with aspect 41, wherein the halogen is selected from the group consisting of $^{18}$F, $^{75}$Br, $^{76}$Br, $^{77}$Br, $^{123}$I, $^{124}$I, $^{125}$I and $^{131}$I.

Aspect 30. A compound or a pharmaceutically acceptable salt thereof in accordance with aspect 41, wherein $R^4$ comprises a radionuclide.

Aspect 31. A compound or a pharmaceutically acceptable salt thereof in accordance with aspect 41, wherein $R^4$ comprises a $^{11}$C.

Aspect 32. A compound or a pharmaceutically acceptable salt thereof in accordance with aspect 41, wherein $R^{13}$ comprises a radionuclide.

Aspect 33. A compound or a pharmaceutically acceptable salt thereof in accordance with aspect 41, wherein the chelator core is selected from the group consisting of NOTA, DOTA, DTPA and triglycine.

Aspect 34. A compound or a pharmaceutically acceptable salt thereof in accordance with aspect 47, wherein the chelator core chelates a metal radionuclide.

Aspect 35. A compound or a pharmaceutically acceptable salt thereof in accordance with aspect 34, wherein the metal radionuclide is an ion selected from the group consisting of an ion of gallium-67 and an ion of gallium-68.

Aspect 36. A compound or a pharmaceutically acceptable salt thereof in accordance with aspect 34, wherein the compound or pharmaceutically acceptable salt comprises an ion selected from the group consisting of an ion of gallium-67, an ion of gallium-68, an ion of an unlabeled gallium, an ion of indium-111, an ion of iron-52, an ion of iron-59, an ion of copper-62, an ion of copper-64, an ion of thallium-201, an ion of technetium-99m, an ion of technetium-94m, an ion of rhenium-188, an ion of rubidium-82, an ion of strontium-92, an ion of yttrium-86, an ion of yttrium-90, an ion of zirconium-86 and an ion of zirconium-89.

Aspect 37. A compound or a pharmaceutically acceptable salt thereof in accordance with aspect 34, wherein the ion is a paramagnetic metal ion.

Aspect 38. A compound or a pharmaceutically acceptable salt thereof in accordance with aspect 34, wherein the compound or pharmaceutically acceptable salt comprises an ion selected from the group consisting of an ion of iron, an ion of manganese and an ion of cobalt.

Aspect 39. A compound or a pharmaceutically acceptable salt thereof in accordance with aspect 34, wherein the compound or pharmaceutically acceptable salt comprises an ion is a lanthanide metal ion.

Aspect 40. A compound or a pharmaceutically acceptable salt thereof in accordance with aspect 34, wherein the compound or pharmaceutically acceptable salt comprises a gadolinium ion.

Aspect 41. A compound or a pharmaceutically acceptable salt thereof, of structure

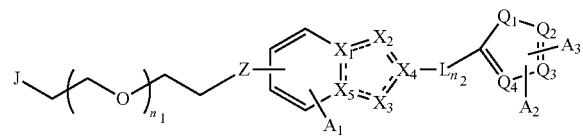

wherein: J is selected from the group consisting of a halogen, hydroxy, cyano, $COOR^1$, carboxy, amide, immino, nitro, $NR^2R^3$ and $OR^4$; $n_1$ is an integer from 0-4; Z is selected from the group consisting of $CH_2$, O, $NR^5$, S and Se; each of $A_1$, $A_2$ and $A_3$ is independently selected from the group consisting of H, F, Cl, Br, I, CN, OH, $NO_2$, $NHR^6$, $NR^7R^8$, $OR^9$, $SR^{10}$, $COOR^{11}$, $COR^{12}$, sulfonic acid,

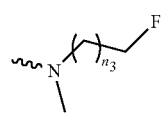

wherein ⌇ is a bond, 2-ethylidenemalononitrile, (E)-2-(but-2-en-1-ylidene)malononitrile, 2-((2E,4E)-hexa-2,4-dien-1-ylidene)malononitrile, acetyl, $-(OCH_2-CH_2)_{n_4}-$ and $R^{13}$; $n_3$ is an integer from 0-4; $n_4$ is an integer from 0-4; ⁝⁝⁝ is a single or double bond; $X_1$ is selected from the group consisting of C and N; $X_2$ is selected from the group consisting of $CH_2$, CH, O, $NR^{14}$, S, Se and N; X is selected from the group consisting of $CH_2$, CH, O, $NR^{15}$, S, Se and N; $X_4$ is selected from the group consisting of C and CH; $X_5$ is selected from the group consisting of N, C and CH; wherein when $X_1$ is C then $X_1$ and $X_5$ are linked by a double bond; wherein when $X_1$ is N, then $X_1$ and $X_5$ are linked by a single bond; wherein when $X_2$ is $NR^{14}$, S, O or Se, then $X_2$ and $X_4$ are linked by a single bond; wherein when $X_2$ is N, then $X_2$ and $X_4$ are linked by a double bond; wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L is selected from the group consisting of $(C_1-C_4)$ alkyl, $(C_3-C_6)$ cycloalkyl, $(C_2-C_8)$ linear alkene, $(C_2-C_8)$ linear alkene, $(C_3-C_8)$ branched alkyne,

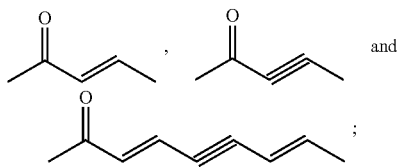

$n_2$ is an integer from 0-4; each of $Q_1$, $Q_2$, $Q_3$ and $Q_4$ is independently selected from the group consisting of C and N, with provisos that at least two of $Q_1$, $Q_2$, $Q_3$ and $Q_4$ are C and at least one of $Q_1$, $Q_2$, $Q_3$, and $Q_4$ is N; each of $R^1$-$R^{15}$ is independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne, $C_{3-7}$ cycloalkyl aryl, and a combination thereof.

Aspect 42. A compound or a pharmaceutically acceptable salt thereof in accordance with aspect 41, wherein the halogen is selected from the group consisting of Cl, F, Br and I.

Aspect 43. A compound or a pharmaceutically acceptable salt thereof in accordance with aspect 41, wherein the halogen is selected from the group consisting of $^{18}F$, $^{75}Br$, $^{76}Br$, $^{77}Br$, $^{123}I$, $^{124}I$, $^{125}I$ and $^{131}I$.

Aspect 44. A compound or a pharmaceutically acceptable salt thereof in accordance with aspect 41, wherein $R^4$ comprises a radionuclide.

Aspect 45. A compound or a pharmaceutically acceptable salt thereof in accordance with aspect 41, wherein $R^4$ comprises a $^{11}C$.

Aspect 46. A compound or a pharmaceutically acceptable salt thereof in accordance with aspect 41, wherein $R^{13}$ comprises a radionuclide.

Aspect 47. A compound or a pharmaceutically acceptable salt thereof, of structure

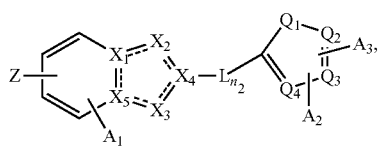

wherein: Z is selected from the group consisting of $CH_2$, O, $NR^1$, S, Se and

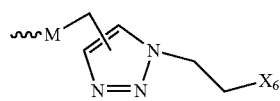

wherein ⌇ is a bond; each of $A_1$, $A_2$ and $A_3$ is independently selected from the group consisting of H, a halogen, CN, OH, $NO_2$, $NHR^2$, $NR^3R^4$, $OR^5$, $SR^6$, $COOR^7$, $COR^8$, sulfonic acid,

wherein ⁓ is a bond, 2-ethylidenemalononitrile, (E)-2-(but-2-en-1-ylidene)malononitrile, 2-((2E,4E)-hexa-2,4-dien-1-ylidene)malononitrile, acetyl-$(OCH_2-CH_2)_{n_4}-(CH_2)_2-$ and $R^9$; $n_3$ is an integer from 0-4; $n_4$ is an integer from 0-4; $X_1$ is selected from the group consisting of C and N; $X_2$ is selected from the group consisting of $CH_2$, CH, O, $NR^{10}$, S, Se and N; $X_3$ is selected from the group consisting of $CH_2$, CH, O, $NR^{11}$, S, Se and N; $X_4$ is selected from the group consisting of C and CH; $X_5$ is selected from the group consisting of N, C and CH; wherein when $X_2$ is $NR^{14}$, S, O or Se, then $X_2$ and $X_4$ are linked by a single bond; wherein when $X_2$ is N, then $X_2$ and $X_4$ are linked by a double bond; wherein when $X_3$ is $NR^{15}$, S, O or Se, then $X_3$ and $X_4$ are linked by a single bond; wherein when $X_3$ is N, then $X_3$ and $X_4$ are linked by a double bond; wherein when both the $X_2$ and $X_5$ are N, then $X_1$ and $X_2$ are linked by a double bond, $X_2$ and $X_4$ are linked by a single bond, $X_3$ and $X_4$ are linked by a double bond, and $X_3$ and $X_5$ are linked by a single bond; wherein when both the $X_1$ and $X_2$ are N, then $X_2$ and $X_4$ are linked by a double bond, $X_3$ and $X_4$ are linked by a single bond, $X_3$ and $X_5$ are linked by a double bond, and $X_1$ and $X_5$ are linked by a single bond; L is selected from the group consisting of $(C_1-C_4)$ alkyl, $(C_3-C_6)$ cycloalkyl, $(C_2-C_8)$ linear alkene, $(C_3-C_8)$ branched alkene, $(C_2-C_5)$ alkyne,

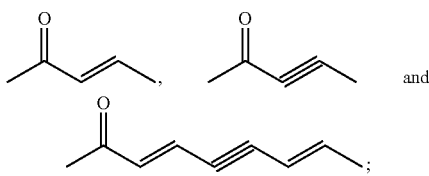

$n_2$ is an integer from 1-4; each of $Q_1$, $Q_2$, $Q_3$, $Q_4$ and $Q_5$ is independently selected from the group consisting of C and N, with provisos that at least two of $Q_1$, $Q_2$, $Q_3$ and $Q_4$ are C and at least one of $Q_1$, $Q_2$, $Q_3$ and $Q_4$ is N; M is selected from the group consisting of O, S, Se, $NR^{12}$, amide, maleimide, urea, haloalkane, haloalkene and haloalkyne; $X_6$ is selected from the group consisting of a halogen, $NH_2$; $NHR^{13}$; $OR^{14}$, $COOR^{15}$, $COR^{16}$, OH, NHQ wherein Q is a chelator core; each of $R^1$-$R^{16}$ is independently selected from the group consisting of H, $C_{1-12}$ linear alkyl, $C_{2-12}$ linear alkene, $C_{2-12}$ linear alkyne, $C_{3-12}$ branched chain alkyl, $C_{3-12}$ branched chain alkene, $C_{3-12}$ branched chain alkyne and $C_{3-7}$ cycloalkyl aryl; and $R^{13}$ optionally comprises a radionuclide.

Aspect 48. A compound or a pharmaceutically acceptable salt thereof in accordance with aspect 47, wherein the halogen is selected from the group consisting of Cl, F, Br and I.

Aspect 49. A compound or a pharmaceutically acceptable salt thereof in accordance with aspect 47, wherein the halogen is selected from the group consisting of $^{18}F$, $^{75}Br$, $^{76}Br$, $^{77}Br$, $^{123}I$, $^{124}I$, $^{125}I$ and $^{131}I$.

Aspect 50. A compound or a pharmaceutically acceptable salt thereof in accordance with aspect 47, wherein $R^4$ comprises a radionuclide.

Aspect 51. A compound or a pharmaceutically acceptable salt thereof in accordance with aspect 47, wherein $R^4$ comprises a $^{11}C$.

Aspect 52. A compound or a pharmaceutically acceptable salt thereof in accordance with aspect 47, wherein $R^{13}$ comprises a radionuclide.

Aspect 53. A compound or a pharmaceutically acceptable salt thereof in accordance with aspect 47, wherein the chelator core is selected from the group consisting of NOTA, DOTA, DTPA and triglycine.

Aspect 54. A compound or a pharmaceutically acceptable salt thereof in accordance with aspect 53, wherein the chelator core chelates a metal radionuclide.

Aspect 55. A compound or a pharmaceutically acceptable salt thereof in accordance with aspect 54, wherein the metal radionuclide is an ion selected from the group consisting of an ion of gallium-67 and an ion of gallium-68.

Aspect 56. A compound or a pharmaceutically acceptable salt thereof in accordance with aspect 54, wherein the compound or pharmaceutically acceptable salt comprises an ion selected from the group consisting of an ion of gallium-67, an ion of gallium-68, an ion of an unlabeled gallium, an ion of indium-111, an ion of iron-52, an ion of iron-59, an ion of copper-62, an ion of copper-64, an ion of thallium-201, an ion of technetium-99m, an ion of technetium-94m, an ion of rhenium-188, an ion of rubidium-82, an ion of strontium-92, an ion of yttrium-86, an ion of yttrium-90, an ion of zirconium-86, an ion of zirconium-89.

Aspect 57. A compound or a pharmaceutically acceptable salt thereof in accordance with aspect 54, wherein the compound or pharmaceutically acceptable salt comprises a paramagnetic metal ion.

Aspect 58. A compound or a pharmaceutically acceptable salt thereof in accordance with aspect 54, wherein the compound or pharmaceutically acceptable salt comprises an ion is selected from the group consisting of an ion of iron, an ion of manganese and an ion of cobalt.

Aspect 59. A compound or a pharmaceutically acceptable salt thereof in accordance with aspect 54, wherein the compound or pharmaceutically acceptable salt comprises a lanthanide metal ion.

Aspect 60. A compound or a pharmaceutically acceptable salt thereof in accordance with aspect 54, wherein the compound or pharmaceutically acceptable salt comprises a gadolinium ion.

Aspect 61. A gold nanoparticle comprising gold conjugated to a compound of any one of aspects 1-12 and 21-60.

Aspect 62. A complex comprising: a compound or a pharmaceutically acceptable salt thereof of any one of aspects 1-12 and 21-60; and a gold nanoparticle.

Aspect 63. A gold nanoparticle conjugated to a compound of any one of aspects 1-12 and 21-60.

Aspect 64. A gold nanoparticle of any one of aspects 61, 62 or 63, further comprising a linker.

Aspect 65. A gold nanoparticle of aspect 64, wherein the linker is an aminothiol.

Aspect 66. A gold nanoparticle of aspect 65, wherein the aminothiol is an aminothiophenol.

Aspect 67. A gold nanoparticle of aspect 66, wherein the aminothiophenol is a p-aminothiophenol.

Aspect 68. A gold nanoparticle of any one of aspects 61-67, wherein the gold is Au-199.

Aspect 69. A gold nanoparticle of any one of aspects 61-67, wherein the gold is Au-198.

Aspect 70. A method of imaging distribution of amyloid beta in a sample or a subject, comprising: administering a compound or a pharmaceutically acceptable salt thereof of any one of aspects 1-12 and 21-69 to the sample or subject wherein the compound or pharmaceutically acceptable salt thereof comprises a radionuclide; subjecting the subject to PET or SPECT scanning.

Aspect 71. A method of imaging distribution of amyloid beta in a sample or a subject, comprising: administering a compound, a pharmaceutically acceptable salt thereof or a gold nanoparticle of any one of aspects 1-12 and 21-69 to the sample or subject; and applying electromagnetic radiation to the subject or sample of a wavelength excitatory for fluorescence of the compound or salt thereof.

Aspect 72. A method of imaging cardiac systemic amyloidosis in a subject, comprising administering an imaging effective amount of a compound, a pharmaceutically acceptable salt thereof or a gold nanoparticle of any one of aspects 1-12 and 21-69 to the subject, and subjecting the subject to PET or SPECT scanning.

Aspect 73. A method of inhibiting amyloid beta aggregation, comprising administering a compound, a pharmaceutically acceptable salt thereof or a gold nanoparticle of any one of aspects 1-12 and 21-69, wherein at least one of Z, $X_2$ and $X_3$ is Se.

Aspect 74. A method of diagnosing or monitoring progression of Alzheimers disease, comprising administering to a subject a compound, a pharmaceutically acceptable salt thereof or a gold nanoparticle of any one of aspects 1-12 and 21-69, and subjecting the subject to PET or SPECT scanning.

Aspect 75. A method of diagnosing or monitoring progression of a neurodegenerative disease, comprising administering to a subject a compound, a pharmaceutically acceptable salt thereof or a gold nanoparticle of any one of aspects 1-12 and 21-69, and subjecting the subject to PET or SPECT scanning.

Aspect 76. A method of diagnosing or monitoring progression of cardiac systemic amyloidosis, comprising administering to a subject a compound, a pharmaceutically acceptable salt thereof or a gold nanoparticle of any one of aspects 1-12 and 21-69, and subjecting the subject to PET or SPECT scanning.

Aspect 77. A method for detecting or ruling out a meningioma in a subject comprising administering to a subject a compound, a pharmaceutically acceptable salt thereof or a gold nanoparticle of any one of aspects 1-12 and 21-69.

Aspect 78. A method for detecting or ruling out a meningioma in a subject in accordance with aspect 77, wherein the detecting comprises PET or SPECT scanning with concurrent computed tomography (CT) imaging, magnetic resonance imaging (MRI), or a combination thereof.

Aspect 79. A method for differentiating the presence of a meningioma from other tumors types in a subject, comprising: administering to a subject a diagnostically acceptable amount of a compound, a pharmaceutically acceptable salt thereof or a gold nanoparticle of any one of aspects 1-12 and 21-69; and detecting retention of the compound, wherein greater activity of the compound compared to a control is diagnostic for meningioma.

Aspect 80. A compound of any one of aspects 1-12 and 21-69 for use in the differential diagnosis of meningioma compared to other tumors.

Aspect 81. A compound of structure

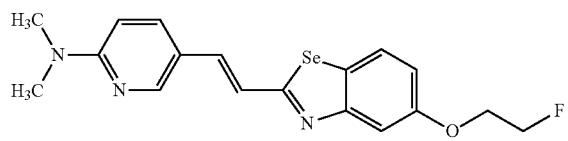 [SMILES: CN(C)c1ccc(/C=C/c2nc3cc(OCCF)ccc3[se]2)cn1]

or a pharmaceutically acceptable salt thereof.

Aspect 82. A compound of structure

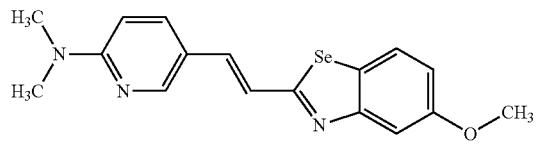

or a pharmaceutically acceptable salt thereof.

Aspect 83. A compound of structure

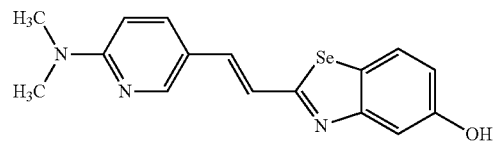 [SMILES: CN(C)c1ccc(/C=C/c2nc3cc(O)ccc3[se]2)cn1]

or a pharmaceutically acceptable salt thereof.

Aspect 84. A compound of structure

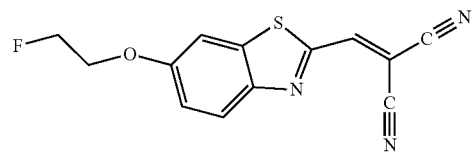 [SMILES: N#CC(C#N)=Cc1nc2ccc(OCCF)cc2s1]

or a pharmaceutically acceptable salt thereof.

Aspect 85. A compound of structure

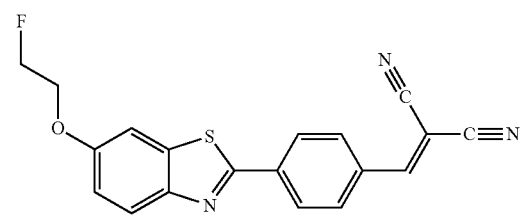 [SMILES: N#CC(C#N)=Cc1ccc(-c2nc3ccc(OCCF)cc3s2)cc1]

or a pharmaceutically acceptable salt thereof.

Aspect 86. A compound of structure

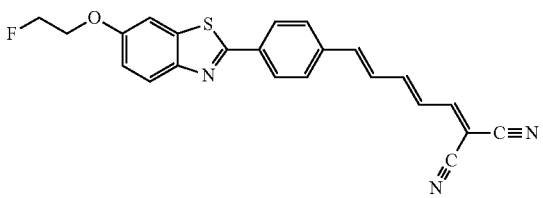 [SMILES: N#CC(C#N)=C/C=C/C=C/c1ccc(-c2nc3ccc(OCCF)cc3s2)cc1]

or a pharmaceutically acceptable salt thereof.

Aspect 87. A compound of structure

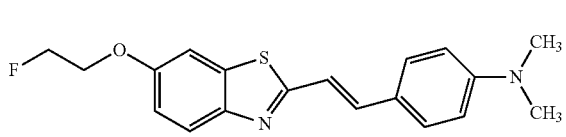 [SMILES: CN(C)c1ccc(/C=C/c2nc3ccc(OCCF)cc3s2)cc1]

or a pharmaceutically acceptable salt thereof.

Aspect 88. A compound of structure

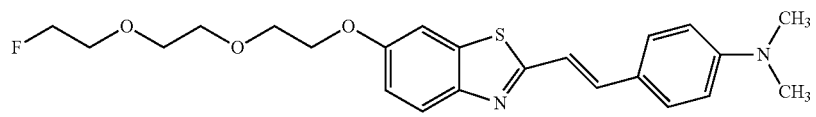 [SMILES: CN(C)c1ccc(/C=C/c2nc3ccc(OCCOCCOCCF)cc3s2)cc1]

or a pharmaceutically acceptable salt thereof.

Aspect 89. A compound of structure

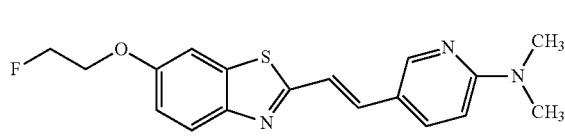 [SMILES: CN(C)c1ccc(/C=C/c2nc3ccc(OCCF)cc3s2)cn1]

or a pharmaceutically acceptable salt thereof.

Aspect 90. A compound of structure

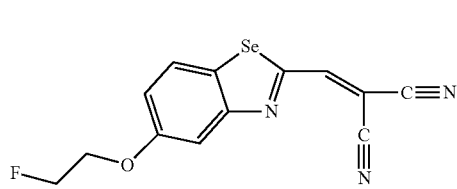 [SMILES: N#CC(C#N)=Cc1nc2cc(OCCF)ccc2[se]1]

or a pharmaceutically acceptable salt thereof.

Aspect 91. A compound of structure

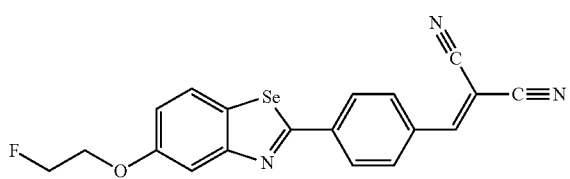 [SMILES: N#CC(C#N)=Cc1ccc(-c2nc3cc(OCCF)ccc3[se]2)cc1]

or a pharmaceutically acceptable salt thereof.

Aspect 92. A compound of structure

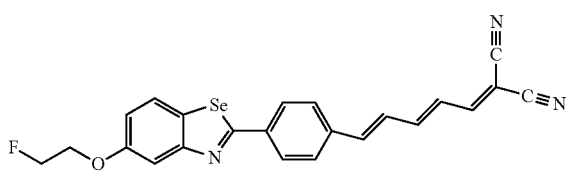 [SMILES: N#CC(C#N)=C/C=C/C=C/c1ccc(-c2nc3cc(OCCF)ccc3[se]2)cc1]

or a pharmaceutically acceptable salt thereof.

Aspect 93. A compound of structure

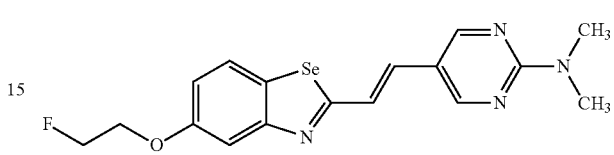

or a pharmaceutically acceptable salt thereof.

Aspect 94. A compound of structure

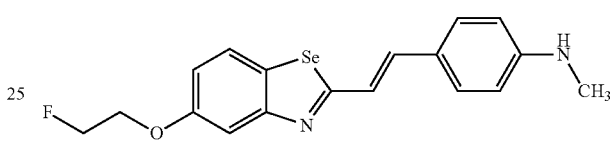

or a pharmaceutically acceptable salt thereof.

Aspect 95. A compound of structure

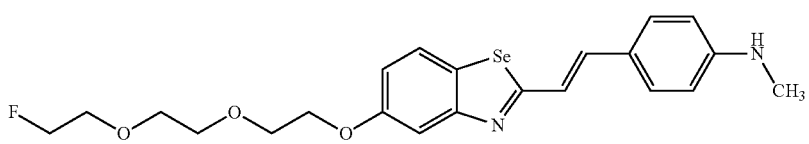 [SMILES: CNc1ccc(/C=C/c2nc3cc(OCCOCCOCCF)ccc3[se]2)cc1]

or a pharmaceutically acceptable salt thereof.

Aspect 96. A compound of structure

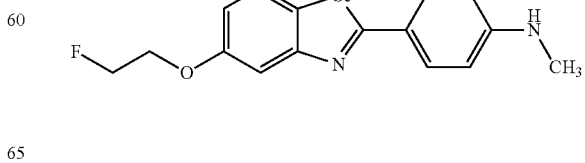

or a pharmaceutically acceptable salt thereof.

Aspect 97. A compound of structure

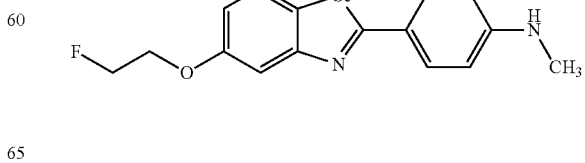

or a pharmaceutically acceptable salt thereof.

Aspect 98. A compound of structure

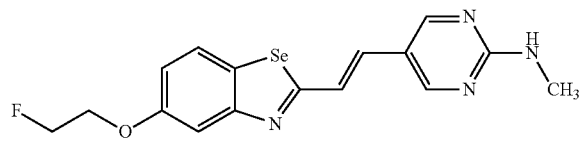 [SMILES: CNc1ncc(/C=C/c2nc3cc(OCCF)ccc3[se]2)cn1]

or a pharmaceutically acceptable salt thereof.

Aspect 99. A compound of structure

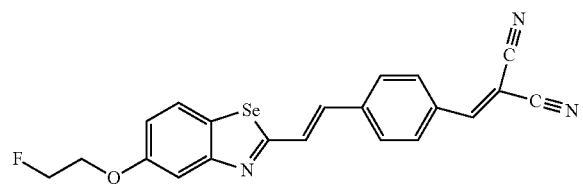 [SMILES: N#CC(C#N)=Cc1ccc(/C=C/c2nc3cc(OCCF)ccc3[se]2)cc1]

or a pharmaceutically acceptable salt thereof.

Aspect 100. A compound of structure

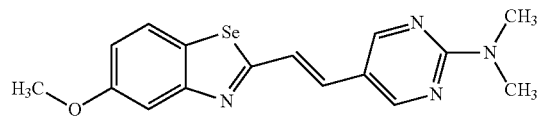

or a pharmaceutically acceptable salt thereof.

Aspect 101. A compound of structure

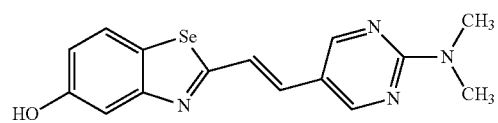 [SMILES: CN(C)c1ncc(/C=C/c2nc3cc(O)ccc3[se]2)cn1]

or a pharmaceutically acceptable salt thereof.

Aspect 102. A compound of structure

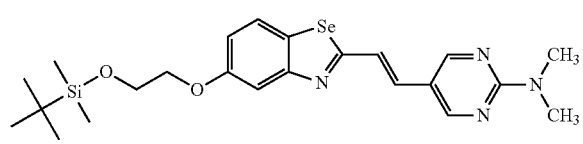 [SMILES: CN(C)c1ncc(/C=C/c2nc3cc(OCCO[Si](C)(C)C(C)(C)C)ccc3[se]2)cn1]

or a pharmaceutically acceptable salt thereof.

Aspect 103. A compound of structure

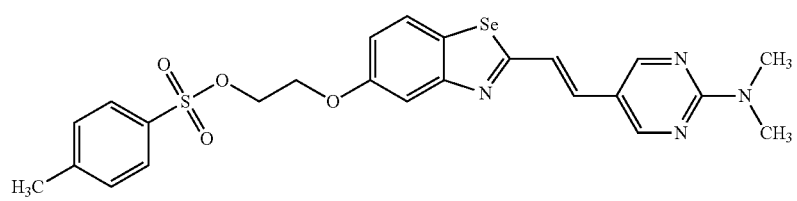

or a pharmaceutically acceptable salt thereof.

Aspect 104. A compound of structure

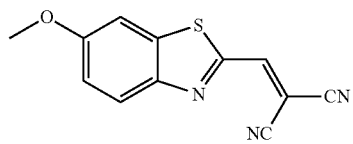 [SMILES: COc1ccc2nc(C=C(C#N)C#N)sc2c1]

or a pharmaceutically acceptable salt thereof.

Aspect 105. A compound of structure

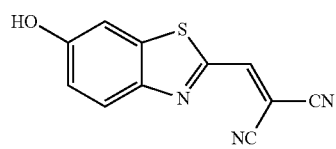 [SMILES: N#CC(C#N)=Cc1nc2ccc(O)cc2s1]

or a pharmaceutically acceptable salt thereof.

Aspect 106. A compound of structure

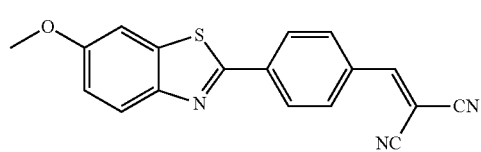 [SMILES: COc1ccc2nc(-c3ccc(C=C(C#N)C#N)cc3)sc2c1]

or a pharmaceutically acceptable salt thereof.

Aspect 107. A compound of structure

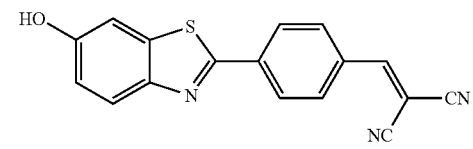 [SMILES: N#CC(C#N)=Cc1ccc(-c2nc3ccc(O)cc3s2)cc1]

or a pharmaceutically acceptable salt thereof.

Aspect 108. A compound of structure

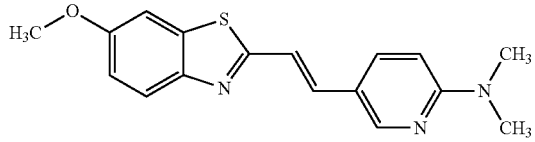

or a pharmaceutically acceptable salt thereof.

Aspect 109. A compound of structure

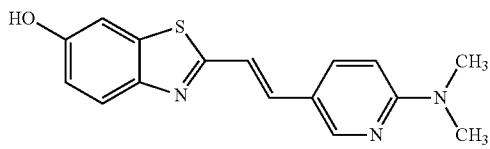 [SMILES: CN(C)c1ccc(/C=C/c2nc3ccc(O)cc3s2)cn1]

or a pharmaceutically acceptable salt thereof.

Aspect 10. A compound of structure

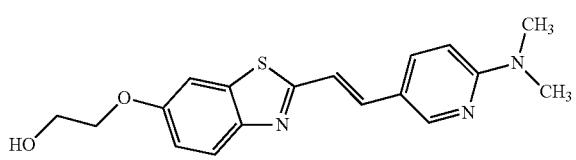 [SMILES: CN(C)c1ccc(/C=C/c2nc3ccc(OCCO)cc3s2)cn1]

or a pharmaceutically acceptable salt thereof.

Aspect 11. A compound of structure

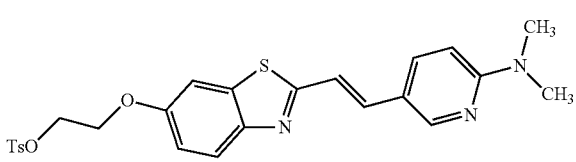 [SMILES: Cc1ccc(S(=O)(=O)OCCOc2ccc3nc(/C=C/c4ccc(N(C)C)nc4)sc3c2)cc1]

or a pharmaceutically acceptable salt thereof.

Aspect 112. Compound

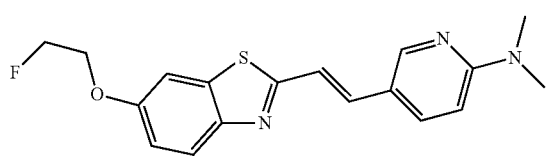 [SMILES: CN(C)c1ccc(/C=C/c2nc3ccc(OCCF)cc3s2)cn1]

or a pharmaceutically acceptable salt thereof, for use in the detection or diagnosis of amyloid in a subject.

Aspect 113. The compound of pharmaceutically acceptable salt thereof of aspect 112, where in F is an $^{18}$F.

Aspect 114. Compound

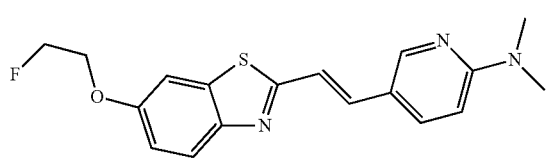 [SMILES: CN(C)c1ccc(/C=C/c2nc3ccc(OCCF)cc3s2)cn1]

or a pharmaceutically acceptable salt thereof, for use in the diagnosis of Alzheimers Disease in a subject.

Aspect 115. Compound

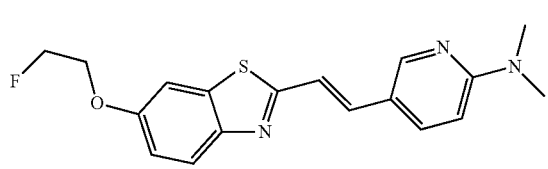 [SMILES: CN(C)c1ccc(/C=C/c2nc3ccc(OCCF)cc3s2)cn1]

or a pharmaceutically acceptable salt thereof, for use in the diagnosis of cardiac systemic amyloidosis in a subject.

Aspect 116. Compound

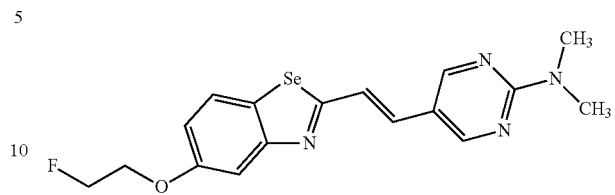

or a pharmaceutically acceptable salt thereof, for use in the diagnosis of Alzheimers Disease in a subject.

Aspect 117. Compound

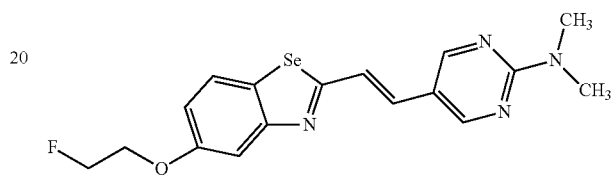

or a pharmaceutically acceptable salt thereof, wherein the F is an $^{18}$F.

Aspect 118. Compound

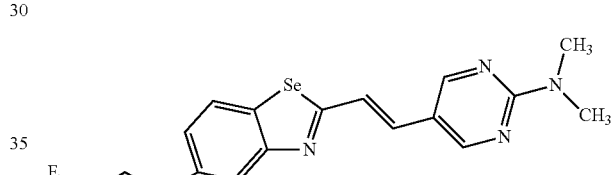

or a pharmaceutically acceptable salt thereof, for use in the detection of amyloid-β.

Aspect 119. Compound

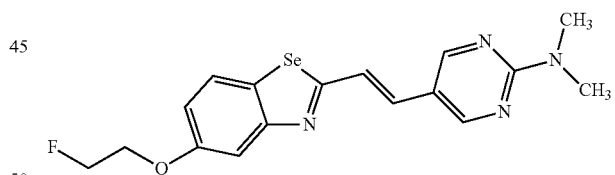

or a pharmaceutically acceptable salt thereof, for use in the detection or diagnosis of amyloid-β plaque in the retina.

Aspect 120. The compound or pharmaceutically acceptable salt of aspect 119, wherein the detection comprises fluorescence detection.

Aspect 121. Compound

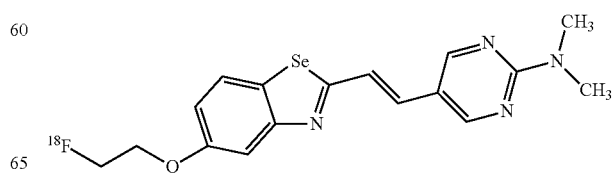

or a pharmaceutically acceptable salt thereof, for use in the detection or diagnosis of amyloid-β plaque in the retina, wherein the detection comprises PET imaging.

Aspect 122. Compound

[Chemical structure shown]

or a pharmaceutically acceptable salt thereof, for use in the detection or diagnosis of amyloid-β by SPECT.

Aspect 123. A compound or a pharmaceutically acceptable salt thereof of any one of aspects 1-12 and 21-60 for use in the detection or diagnosis of amyloid in a subject.

Aspect 124. A compound or a pharmaceutically acceptable salt thereof of any one of aspects 1-12 and 21-60 for use in the detection or diagnosis of a cancer selected from the group consisting of a prolactinoma, a choroid plexus papilloma, a low grade lymphoma, and a pituitary tumor.

Aspect 125. A compound or a pharmaceutically acceptable salt thereof of any one of aspects 1-12 and 21-60 for use in the detection or diagnosis of a cancer selected from the group consisting of glioblastoma, brain cancer, breast cancer and pancreatic cancer.

Aspect 126. A compound or a pharmaceutically acceptable salt thereof of any one of aspects 1-12 and 21-60 for use in the detection of amyloid precursor protein.

BRIEF DESCRIPTION OF THE DRAWINGS

In drawings based on multi-color originals, gray-scale versions of each color channel (red, green and/or blue) are shown, as well as a composite gray scale that combines all 3 (RGB) color channels.

[Chemical structure shown]

Figure 2:
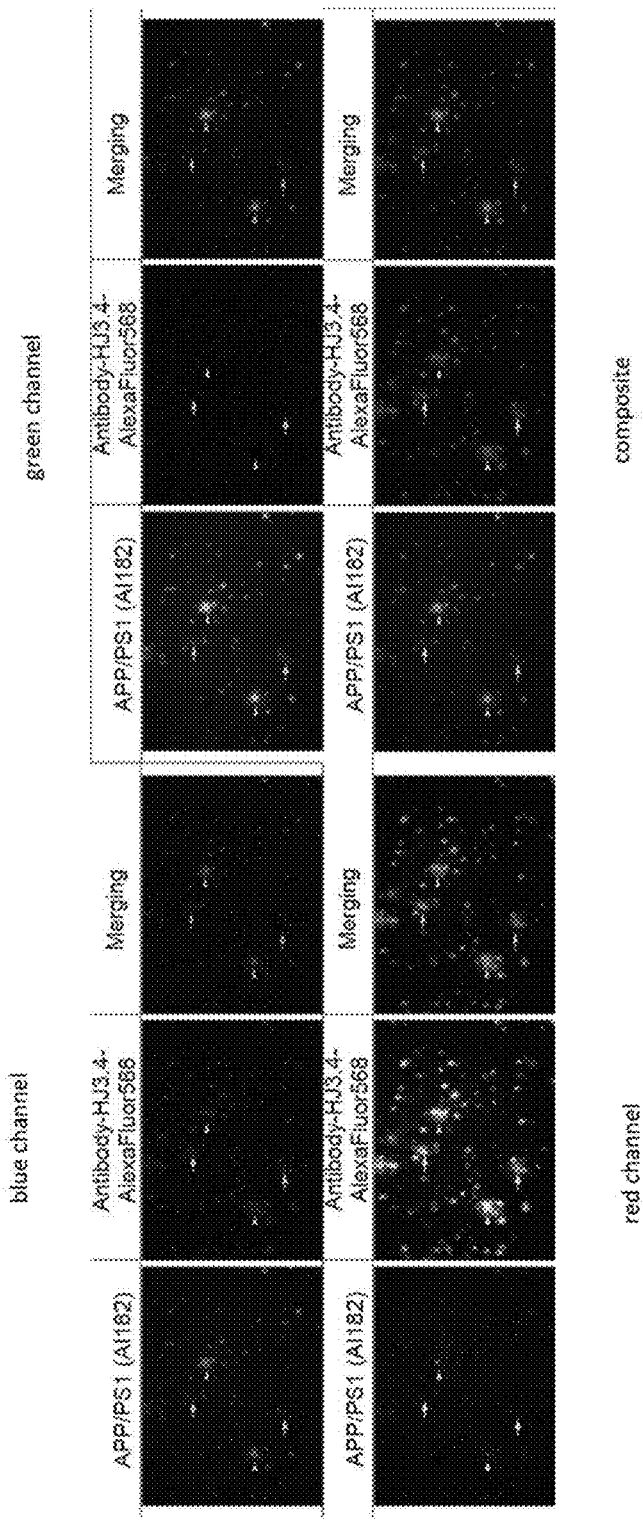

FIG. 2 illustrates staining of both fibrillar and diffuse plaques ex vivo in the hippocampus and cortical region of brain sections in APPsw+/−/PS1 mice using agent F-AI-182.

Figure 3:
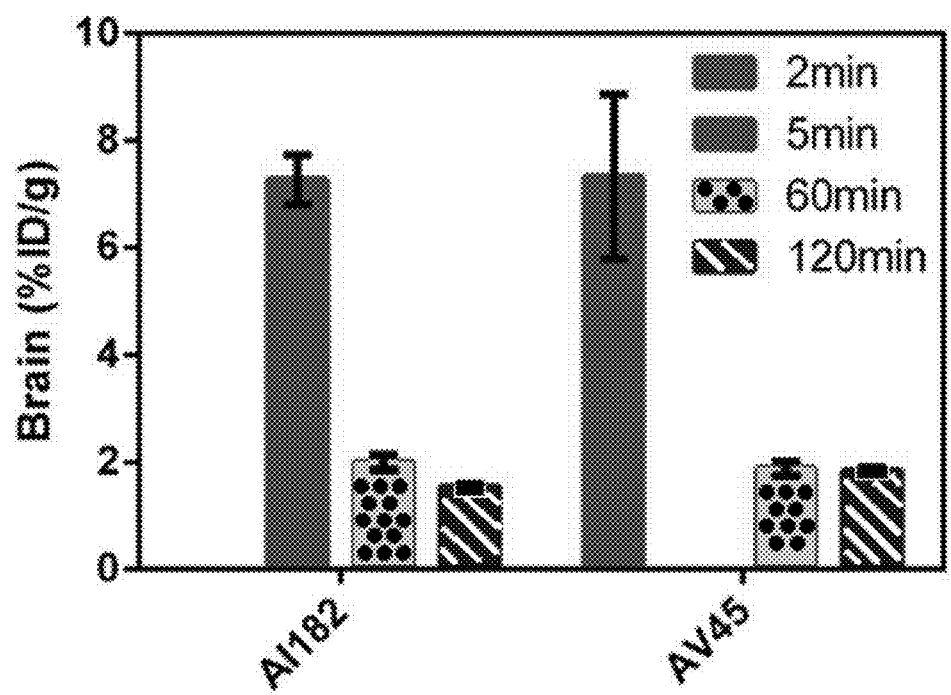

FIG. 3 illustrates a comparative analysis of pharmacokinetics in normal mice for $^{18}$F-AI-182 of structure

[Chemical structure shown]

and $^{18}$F-AV-45 of structure

[Chemical structure shown]

Figure 4:
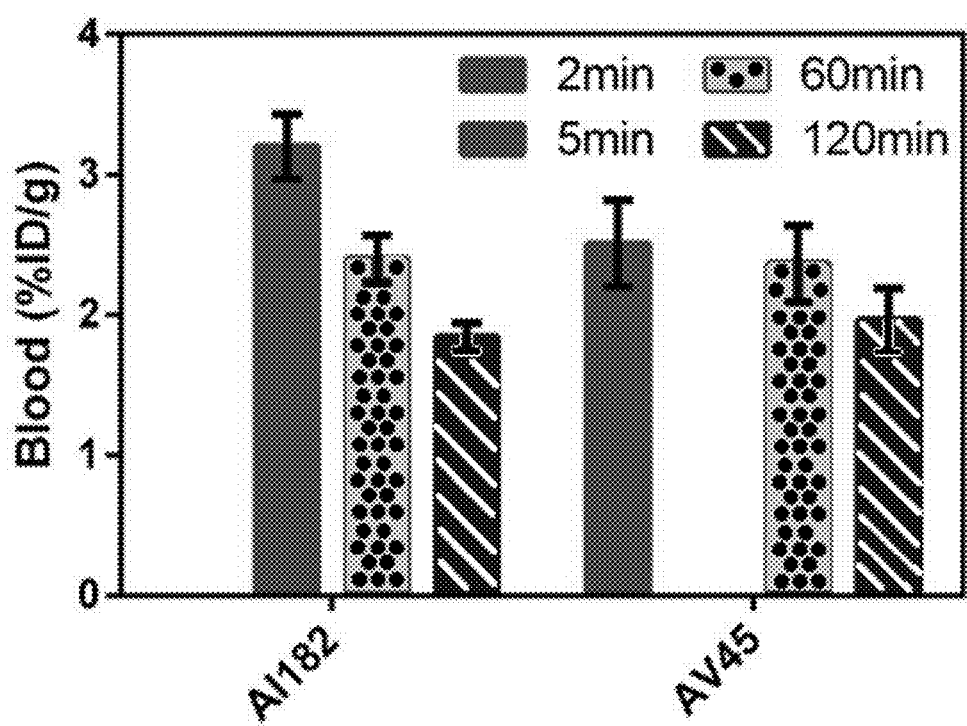

FIG. 4 illustrates that $^{18}$F-AI-182 is washed out from blood (25% faster than AV-45) in absence of targeted plaques and remains non-metabolized in human serum. $^{18}$F-AI-182 shows facile penetration of the brain and clearance in normal mice.

Figure 5:
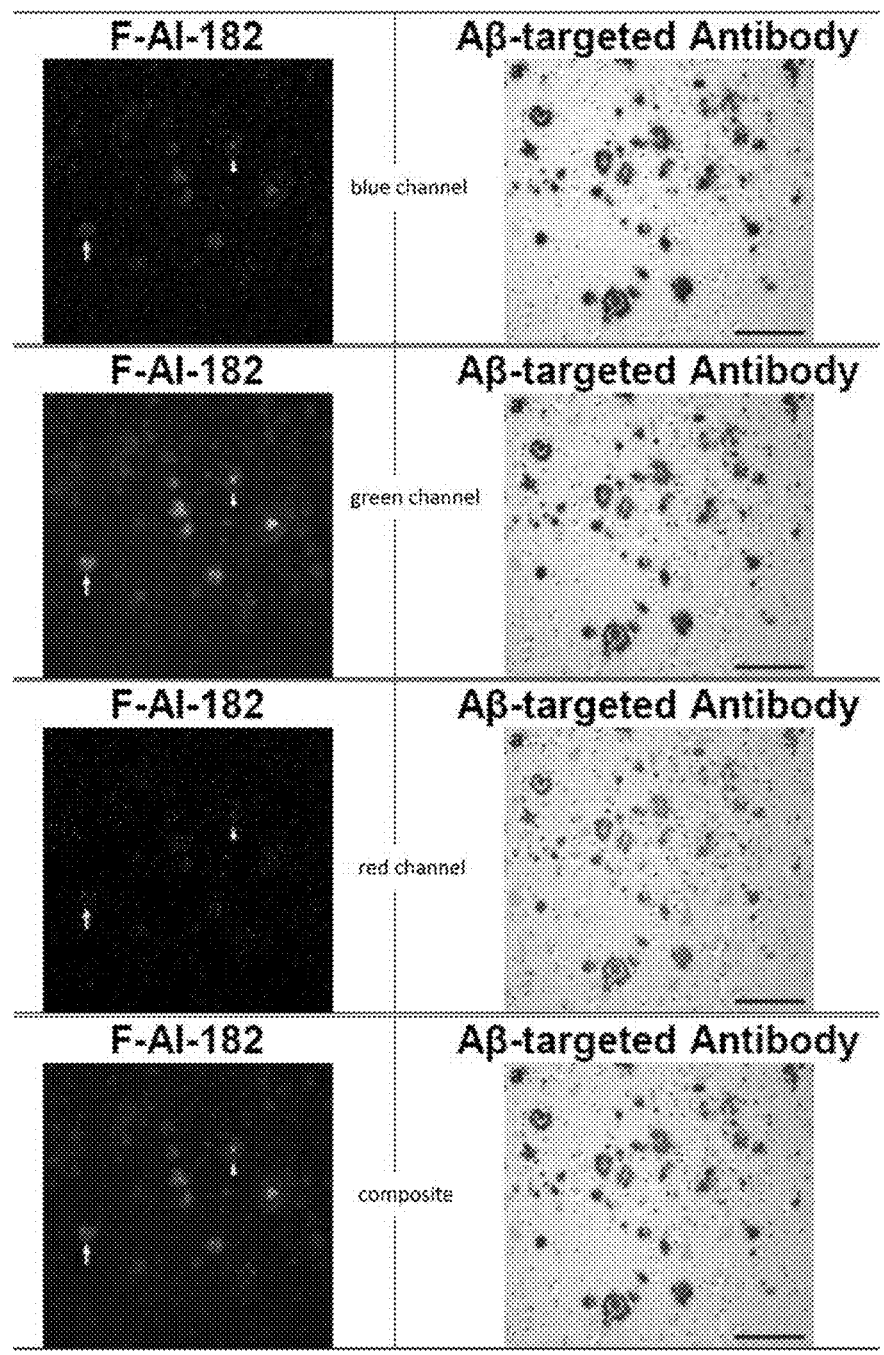

FIG. 5 illustrates that F-AI-182 can be used to detect both diffuse and compact Aβ plaques in the brain cross-sections of frontal lobe of a 90-year-old female with neuropathologically confirmed Alzheimer's disease.

Figure 6:
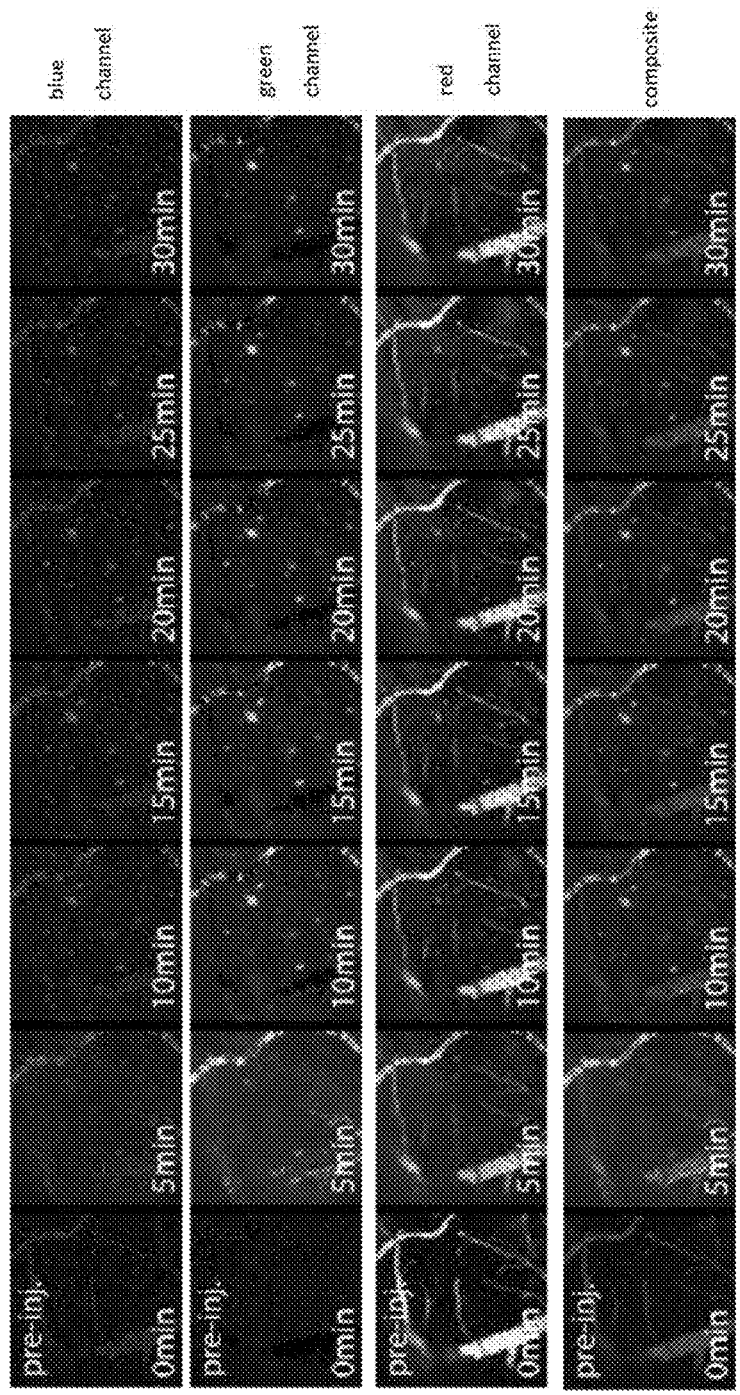

FIG. 6 illustrates real time imaging using F-AI-182.

Figure 7:
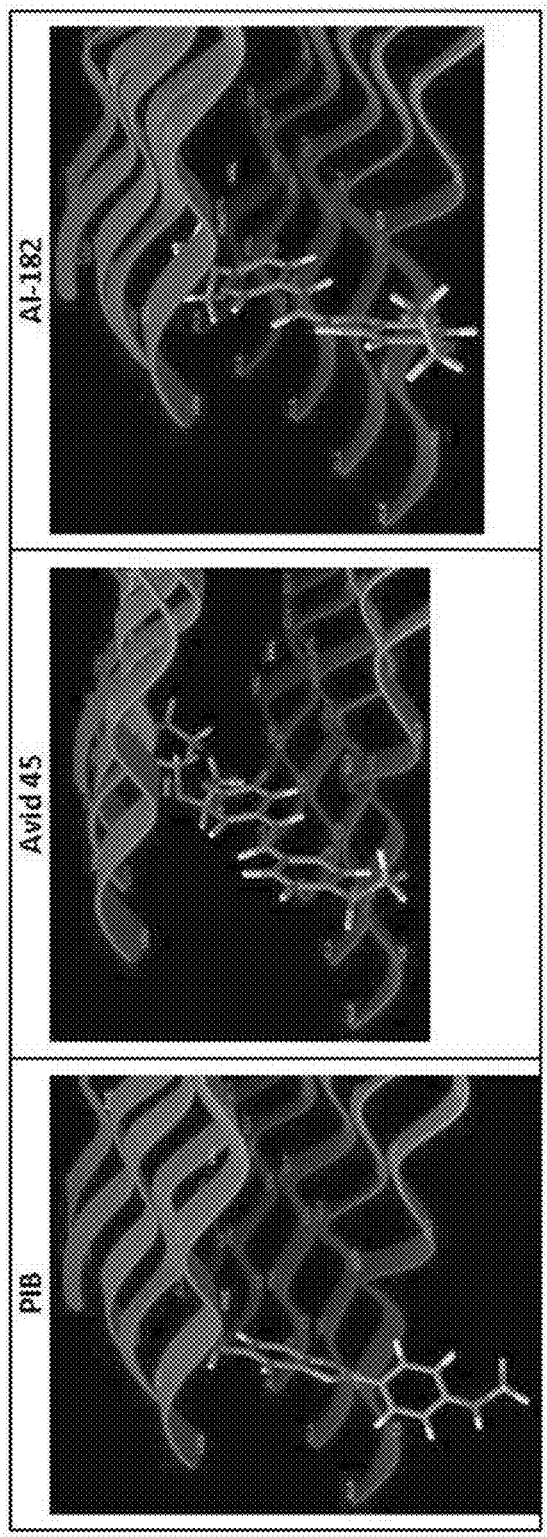

FIG. 7 illustrates assessment of binding sites of PIB, AV-45, and AI-182.

Figure 8:
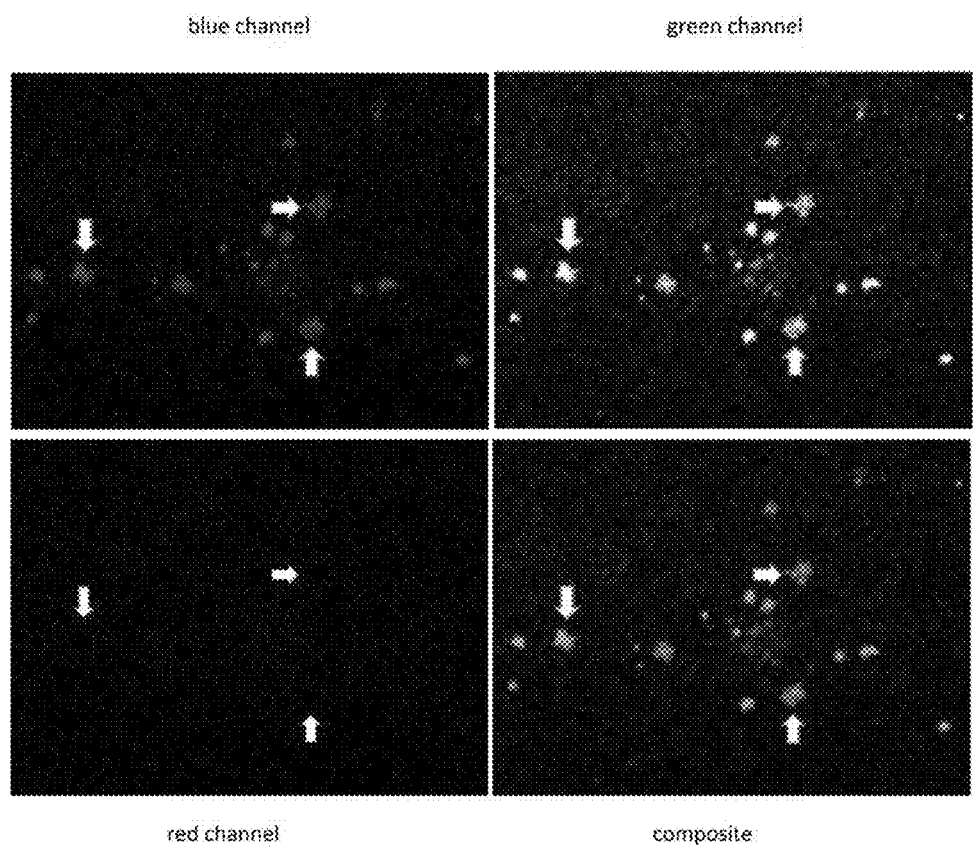

FIG. 8 illustrates staining of brain tissue sections from APPsw+/− (24 months old) mice using F-AI-183 of structure

[Chemical structure shown]

Figure 9:
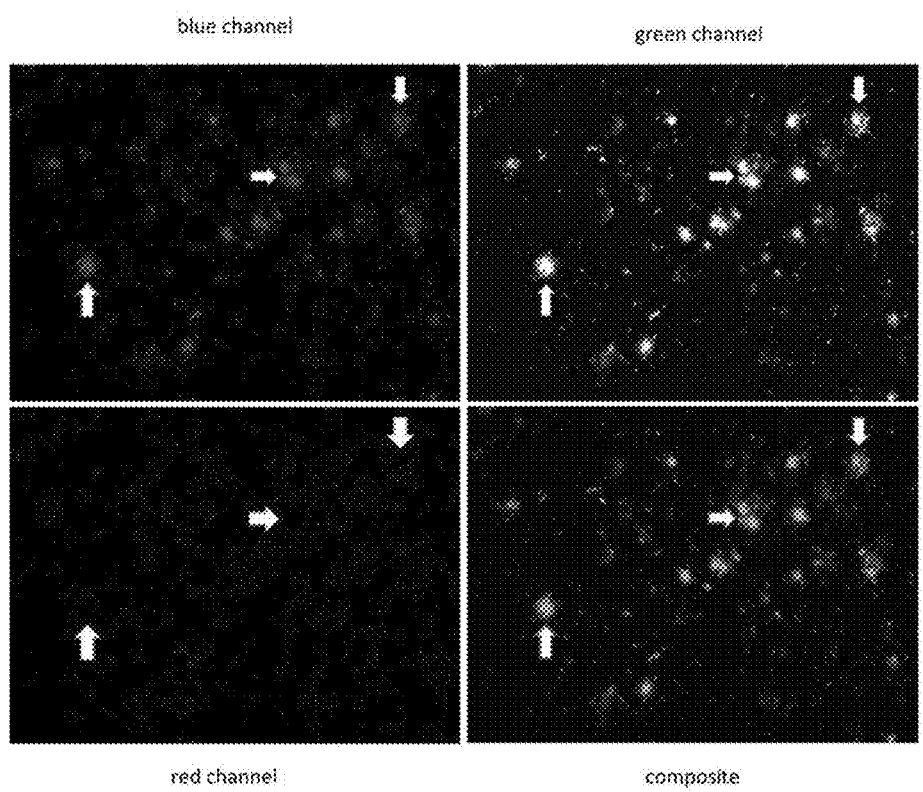

FIG. 9 illustrates detection of compact Aβ plaques in the brain cross-sections of frontal lobe of an 88-year-old female with neuropathologically confirmed Alzheimer's disease using F-AI-183.

Figure 10:
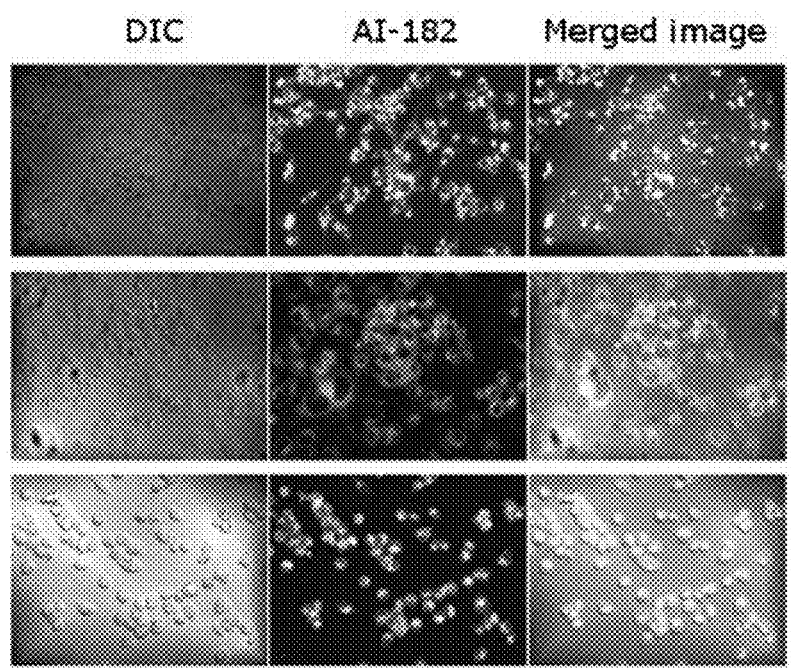

FIG. 10 illustrates fluorescence imaging of tumor cells in vitro, labeled by uptake of fluorescent AI-182.

DETAILED DESCRIPTION

Abbreviations
Aβ Amyloid beta
AD Alzheimer's Disease
ADME absorption, distribution, metabolism, and excretion
APP amyloid precursor protein
BBB blood-brain barrier
BS1 binding site 1
BS2 binding site 2
BS3 binding site 3
$^{13}$C NMR carbon nuclear magnetic resonance
CAA cerebrovascular amyloid angiopathy
CERAD Consortium to Establish a Registry for Alzheimer's Disease
DS Down Syndrome
$^{19}$F NMR fluorine nuclear magnetic resonance
$^{1}$H NMR proton nuclear magnetic resonance
HPLC high-performance liquid chromatography
HRMS high-resolution mass spectroscopy
MIRD Medical Internal Radionuclide Dose Committee
NIA-RI National Institute of Aging-Reagan Institute
NFT neurofibrillary tangle
NMR nuclear magnetic resonance
PBS phosphate buffered saline
PET positron emission tomography
SAR Structure-Activity Relationships
SP senile plaque
SPECT single photon emission computed tomography WT wild type The present teachings disclose agents that can be used for imaging cancers and neurodegenerative diseases. Reagents described herein also have therapeutic use in neurodegenerative diseases and cardiovascular diseases.

In various embodiments, a fluorine-18-based PET probe can be capable of targeting high prevalence sites of Aβ and displaying faster kinetics compared to non-targeted regions, such as white matter. In various embodiments, a fluorine-18-based PET probe can be used for quantitative amyloid imaging for monitoring progress of Aβ-modifying treatments in the presymptomatic and symptomatic stages of Alzheimer's disease (AD), and/or premortem diagnosis of AD.

In various embodiments, the present teachings include heterocyclic molecules (exemplified as F-AI-182) that can bind to Aβ aggregates in vitro with concentration dependent and saturable binding. For example and without limitation, binding constants to preformed $A\beta_{1-42}$ fibrils can be F-AI-182, 59±7 nM; F-AI-183, 17 nM; F-AI-187, 1.58 nM±0.05 nM. In various configurations, these probes can stain both fibrillar and diffuse plaques ex vivo in the hippocampus and cortical region of brain sections in APPsw$^{+/-}$/PS1 mice and human tissues. In some aspects, F-AI-182 can incorporate $^{18}$F ($t_{1/2}$=110 min), a radionuclide for medical PET imaging (Mahmood, A. & Jones, A. Technetium Radiopharmaceuticals. Handbook of Radiopharmaceuticals. 323-362 (2003); Eckelman, W. The Development of 99mTc Radiopharmaceuticals for Perfusion and Biochemistry: In Technetium and Rhenium in Chemistry and Nuclear Medicine 3. M. Nicolini, G. Bandoli and U. Mazzi (Eds.). Cortina Int., Verona, Italy. pp. 571-580. (1990); Narra, R., et al. A Neutral Tc-99m Complex for Myocardial Imaging. J. Nucl. Med. 30, 1830-1837 (1989); Stadalnik, R., Kudo, M., Eckelman, W. & Vera, D. In vivo functional imaging using receptor-binding radiopharmaceuticals: 99mTc-galactosyl-neoglycoalbumin (TcNGA). Investigative Radiology 28, 64-70 (1993)). In some aspects, F-AI-182 can be used for diagnostic assessment of Aβ burden in earlier stages of AD prior to expression of clinical symptoms. In some aspects, a radiolabeled counterpart $^{18}$F-AI-182 can demonstrate a high initial brain penetration (7.28±0.46% % ID/g) of FVB mice, followed by 25% faster clearance from the blood pool (compared with AV-45) in normal mice in the absence of targeted plaques. In some aspects, $^{18}$F-AI-182 can remain non-metabolized until about 30 min (investigated highest time-point) in human serum. In some aspects, F-AI-182 can demonstrate characteristics that enhance overall signal to background ratios and assist image analysis including lack of metabolites and high first-pass extraction into brain of coupled with fast clearance from the blood pool.

In some embodiments, a tracer of the present teachings can provide high target/background ratios. In some aspects, multiphoton microscopy can demonstrate that an unlabeled counterpart F-AI-182 of the radiolabeled PET agent can label brain parenchymal Aβ plaques as well as tracked cerebrovascular amyloid angiopathy (CAA), indicating its ability to serve as a noninvasive probe for assessment of plaque burden in brain. In some aspects, these data can illustrate a platform technology for image analysis in biomedical PET imaging, using an F-18 labeled PET agent.

In various embodiments, a functional probe of the present teachings can have hydrophobic characteristics to cross the blood-brain barrier (BBB) and not be retained in non-targeted regions of the brain. In various aspects, a fluorescent molecule of the present teachings can show enhanced fluorescence upon binding to fibrils, can stain both fibrillar and diffuse plaques in brain cross sections of APP/PS1 transgenic mice and human AD tissues, and can show high initial penetration in the normal brain followed by clearance in the absence of targeted plaques. In various aspects, the agent can clear rapidly from other organs, such as liver and kidney, remain non-metabolized in human serum, and display modest hydrophobicity (log P 1.2) for formulation in 2% ethanol and 98% saline for intravenous injections. The scaffold of F-AI-182 can be used for interrogating AD in a prodromal phase.

In some embodiments, heterocyclic small organic molecules of the present teachings can also be used for multimodality imaging of Aβ using PET/Optical imaging in preclinical applications.

In some embodiments, an agent can exhibit enhanced brain penetration, Aβ interaction, and the ability to interact with highly prevalent or more-dense binding sites on Aβ. In some embodiments, an agent can be identified by either the lack of binding or reduced binding to the white matter for enhancing sensitivity of tracers for Aβ detection in human tissues. In some embodiments, an agent of the present teachings can label Aβ plaques in brain parenchyma <5 min post-intravenous administration.

In some embodiments, the specificity of agents can be determined for Aβ compared to other biomarkers prevalent in neurodegenerative disorders (with overlapping symptoms) such as, tan protein, neurofibrillary tangles (NFT) and Lewy body, including further optimization of targeting properties through SAR study. In some embodiments, an agent can exceed or mimic the pharmacokinetic profiles (brain uptake and blood clearance) of $^{18}$F-AV-45, an FDA approved agent for imaging Aβ in brain. In an embodiment, $^{18}$F-AI-182 showed facile penetration of the blood-brain barrier (BBB) in in vitro targeting of Aβ in a mouse model.

In some embodiments, a compound of the present teachings can be used for noninvasive assessment of Aβ in early stages of AD prior to clinical expression, and can allow therapeutic interventions for disease management. In some embodiments, a compound of the present teachings can be used for stratification of patients in early phases of AD to allow for therapeutic interventions.

Embodiments of Aβ-targeted agent can include functional components including but not limited to the following examples.

An embodiment of an Aβ-targeted agent can include a benzothiazole moiety without the methyl group on the heterocyclic nitrogen of thioflavin T. This can allow the removal of the positive charge to increase the affinity of the probe to Aβ fibrils and enhance hydrophobicity to facilitate BBB penetration.

An embodiment of an Aβ-targeted agent can include modifications on the $6^{th}$ position of the benzothiazole ring has been shown to impact affinity of probes for plaques.

An embodiment of an Aβ-targeted agent can include the introduction of an olefin bond between the benzothiazole moiety and the aromatic ring to increase electron density as well as flexibility of the molecule to promote interactions with other binding sites on Aβ plaques.

An embodiment of an Aβ-targeted agent can include substituting a basic dimethylamino group into an aromatic ring at p-position to the olefinic carbon. In some configurations, this can allow an increase electron density on nitrogen.

An embodiment of an Aβ-targeted agent can include incorporation of a heteroatom, such as nitrogen in the aromatic ring ortho to the highly basic dimethyl-amino group. In some configurations, this can allow better resonance stabilization of the molecule for influencing Pi-Pi interactions and can allow targeting of highly dense and moderate affinity sites on Aβ fibrils.

Methods

Methods and compositions described herein utilize laboratory techniques well-known to skilled artisans. Such technique guidance can be found in laboratory manuals and textbooks such as Spector, D. L. et al., Cells: A Laboratory Manual, Cold Spring Harbor Laboratory Press, Cold Spring Harbor, N.Y., 1998; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L, Imaging in Oncology, Cambridge University Press, Cambridge, U.K., 1998; Welch, M. J., and Redvanly, C. S., eds. Handbook of Radiopharmnaceuticals: Radiochemistry and Applications, J. Wiley, New York, 2003.

In some embodiments of the present teachings, biochemical characterization of F-AI-182 and other molecules can by performed agents via multiple binding and competitive displacement assays using PIB, AV-45, AZD4694, and BAYER 94-9172 for evaluation of targeted sites on Aβ, phosphorimaging studies in vitro. In vivo, ex vivo binding studies of AD brain homogenates and human AD brain sections can be performed, including specificity for Aβ evaluated compared with other biomarker proteins (tau, prion, TDP43, and α-synclein) prevalent in other neurodegenerative diseases to determine target selectivity, and perform metabolite studies.

In some embodiments of the present teachings, the inventors have biochemically characterized and validated agents via multiple in vitro bioassays to evaluate target sensitivity and specificity. The inventors can evaluate an Aβ-targeted agent of the present teachings to detect Aβ plaques via MicroPET imaging with pharmacokinetic analysis in APP transgenic mice and their WT counterparts. Investigations of the present teachings include a focused Structure-Activity Relationships (SAR) study to discover Aβ-targeted agents. The agents obtained from SAR can be biochemically characterized and evaluated through biodistribution and pharmacokinetic studies. The findings can be used to further characterize Aβ-targeted probes such as $^{18}$F-AI-182.

In some embodiments of the present teachings, heterocyclic small organic molecules can be characterized and validated through various analytical steps. In various embodiments, molecules can also be radiolabeled, HPLC purified, and undergo a chemical characterization for developing as either radiopharmaceuticals or optical probes. In some aspects, he HPLC purified organic molecules and their radiolabeled counterparts can be tested for binding affinity. The compounds can be evaluated in animal models using either microPET imaging or multiphoton imaging. The agents that can detect Aβ plaques in mice can also undergo metabolite analysis in vivo for interrogating their translational potential. The agents that remain non-metabolized in the targeted tissue (brain) can also be investigated via pharmacokinetic studies in age-matched APP transgenic and control mice for assessing preliminary signal-to-noise ratios.

In some embodiments of the present teachings, binding assays to preformed Aβ fibrils or AD brain homogenates are disclosed.

In some configurations, the present teachings include preparation of Aβ fibrils or AD brain homogenates. In vitro binding assays can be performed to evaluate interactions of radiolabeled peptides with fibrils of Aβ$_{1-40/42}$ or extracts of AD brain homogenates (Choi, S. R., et al. Preclinical properties of $^{18}$F-AV-45: a PET agent for Aβ plaques in the brain. J Nucl Med 50, 1887-1894 (2009)) in histopathological core of the Alzheimer's Disease Research Center (ADRC), using standard procedures described in the literature (Zhuang, Z., et al. Structure-activity relationships of imidazo[1,2-a]pyridines as ligands for detecting amyloid plaques in the brain. J Med Chem 46, 237-243 (2003)).

In some embodiments of the present teachings, binding assays to preformed fibrils or AD brain homogenate extracts can be performed using literature procedures (Klunk, W., et al. Uncharged thioflavin-T derivatives bind to amyloid-beta protein with high affinity and readily enter the brain. Life Sci 69, 1471-1484 (2001); Zhen, W., et al. Synthesis and amyloid binding properties of rhenium complexes: preliminary progress towards a reagent for SPECT imaging of Alzheimer's disease brain. J Med Chem 42, 2805-2815 (1999)). Prior to binding assays, the stock solution (2 μM) can be thawed. To aliquots of this stock solution, $^{18}$F-AI-182 (also exemplified for either $^{18}$F-AI-183 or $^{18}$F-AI-187) can be added at various concentrations to a final concentration of 200 nM Aβ fibrils or 200 μL of AD brain extracts (20-25 μg). The aggregate-bound $^{18}$F-AI-182 (or other analogues) can be collected on Whatman GF filters using Brandon M-24R cell harvester, washed, and counted in a γ-counter (Perkin Elmer). Inhibition constants ($K_i$) can be calculated as described previously (Han, H., Cho, C. & Lansbury, P. J. Technetium complexes for quantification of brain amyloid. J Am Chem Soc 118, 4506-4508 (1996)). Binding assay results can assist in evaluation of target specificity.

Some embodiments of the present teachings include evaluation of binding sites. In some configurations, binding assays can be done as described above in at least Example 8 below. Fixed concentrations of Aβ$_{1-42}$ fibrils and $^{18}$F-AI-182 can be incubated in the presence of increasing concentration of cold competitors [thioflavin T (BS1), PIB (BS3 & BS1), FDDNP (BS3 & BS1) and BSB (BS2)]. Cold PIB, BSB, and FDDNP can be synthesized using published procedures. Experiments can also be performed with AV-45, BAYER 94-9172, and AZD4694. Measurements can be performed in triplicate and processed as described in the Examples. Agents competing for sites targeted by $^{18}$F-AI-182 can be expected to displace $^{18}$F-AI-182. Agents competing for different sites can be expected to have minimal effects. This analysis can identify binding site specificity on Aβ.

Some embodiments of the present teachings include immunohistochemistry and phosphorimaging of labeled probes ex vivo and in vivo.

In various configurations, staining experiments on mice (WT and APP transgenic) brain sections can be performed with either fluorescent Aβ-targeted F-AI-182 (exemplified for other analogues) or highly specific Aβ-targeted HJ3.4 mouse monoclonal antibody conjugated to Alexa 568 (DeMattos, R. B., et al., Clusterin promotes amyloid plaque formation and is critical for neuritic toxicity in a mouse model of Alzheimer's disease. Proc Natl Acad Sci USA 99, 10843-10848 (2002)), and phosphorimaging can also be performed using $^{18}$F-AI-182. For in vivo experiments, $^{18}$F-AI-182 (exemplified for other analogues) can be intravenously injected. After 2 min and up to 2 h, mice (transgenic APP or APP/PS1 or WT) can be sacrificed, brains removed, dissected into two halves, processed and analyzed as described in this disclosure. Stained brain tissue sections of APPsw$^{+/-}$ can serve as positive controls and the non-stained tissue sections from brains of WT mice can provide negative controls. Radioactive brain tissues can be analyzed directly on a phosphorimager. $^{18}$F-AI-182 (exemplified for other analogues) showing activity patterns consistent with the staining of unlabeled F-AI-182 or Aβ-targeted HJ3.4 mouse monoclonal antibody-Alexa 568 can be further examined.

In some embodiments, an Aβ-targeted heterocyclic molecule can stain or label Aβ plaques in cortical and hippocampal brain sections of APPsw$^{+/-}$ transgenic mice compared to none or minimal interaction in WT controls. Other embodiments can include labeled heterocyclic molecules that show a correlation between immunohistochemistry, phosphorimaging, and staining using Aβ-targeted HJ3.4 mouse monoclonal antibody-Alexa 568.

Some embodiments of the present teachings include evaluation of target specificity in human brain tissues using F-AI-182 or other Aβ-targeted agents.

In various configurations, specificity of F-AI-182 or other agents can be interrogated. Staining using F-AI-182 or immunohistochemistry can be performed using antibodies such as antibodies against Aβ (10D5, Eli Lilly), phosphorylated tau (PHF-1, Albert Einstein Medical School, Bronx, N.Y.), ubiquitin (Dako, Glostrup, Denmark), α-synuclein (LB-509, Zymed, CA), and TDP-43 (Proteintech, Inc., Chicago, Ill.) using established methods (e.g., Burack, M. A., et al. In vivo amyloid imaging in autopsy-confirmed Parkinson disease with dementia. Neurology 74, 77-84 (2010)). Sections can be processed and analyzed on a Zeiss LSM 5 PASCAL confocal system coupled to a Zeiss Axiovert 200 microscope. Aβ targeted agents that demonstrate specificity for Aβ in brain sections of diseased subjects consistent with the expected regional distribution of plaques compared to their healthy controls and lack of cross reactivity with histopathological markers (tau, TDP43; and α-synuclein) can thus be investigated.

In some embodiments of the present teachings, metabolic stability of $^{18}$F-AI-182 and/or other agents can be evaluated.

In various configurations, identified heterocyclic molecules can be assessed for metabolic stability for use in biomedical imaging applications both in vitro and in vivo using established procedures (e.g., Mathis, C., et al. Synthesis and evaluation of $^{11}$C-labeled 6-substituted 2-arylbenzothiazoles as amyloid imaging agents. J. Med. Chem. 46, 2740-2754 (2003); Sharma, V. Radiopharmaceuticals for assessment of multidrug resistance P-glycoprotein-mediated transport activity. Bioconjug. Chem. 15, 1464-1474 (2004)). In some embodiments, $^{18}$F-AI-182, another agent, or a combination thereof can be incubated in either serum or human serum albumin at time points corresponding to uptake in vivo (5 min to 2 h) and filtered through filters (30 kDa). Free and bound radiotracer can be calculated using previously describe methods (Bartholoma, M. D., et al. Effect of the prosthetic group on the pharmacologic properties of $^{18}$F-labeled rhodamine B, a potential myocardial perfusion agent for positron emission tomography (PET). J Med Chem 55, 11004-11012 (2012)), and can be analyzed by radio-TLC scanner and radio-HPLC. For in vivo pharmacokinetics experiments, $^{18}$F-AI-182 agent or other agents can be injected into mice via tail-vein, and mice can be sacrificed at the time points corresponding with data of our biodistribution studies (5 min to 2 h). Brain tissues, liver, and kidney can be removed (liver and kidney can be used to evaluate their metabolic stability in more stringent in vivo environments), sonicated, extracted and analyzed through radio-TLC and -HPLC. The $^{18}$F-AI-182, other agents, or combinations thereof that demonstrate stability (>95%) at the targeted site through this analysis can be investigated further in nonhuman primates models.

Various embodiments of the present teachings include biodistribution and pharmacokinetic studies of $^{18}$F-AI-182 or other agents in normal and transgenic APPsw$^{+/-}$/PS1 mice.

In various configurations, pharmacokinetic analysis of unlabeled fluorescent small organic molecules, $^{18}$F-heterocyclic molecules, and/or their $^{18}$F-counterparts via biodistribution studies in age-matched APPsw$^{+/-}$ transgenic mice and WT mice can be performed to determine target-specificity, and measure the detection of in vivo Aβ plaques, in APPsw$^{+/-}$/PS1 transgenic mice versus control mice, using either multiphoton imaging or microPET/CT imaging system by $^{18}$F-heterocyclic small organic molecules.

In various configurations, agents can be evaluated in part by exploring the tissue distribution and kinetics of $^{18}$F-AI-182 or other agents in normal mice and transgenic mice. Because these heterocyclic molecules can be labeled with $^{18}$F using the methods described herein, biodistribution in normal mice can be determined. In such investigations, BL/6 (control mice; Taconic) or APPsw$^{+/-}$/PS1 (transgenic, Taconic) mice can be anesthetized by isoflurane inhalation and injected with $^{18}$F-AI-182 or other agents (20 μCi in 50-100 μl saline) via bolus injection through a tail vein. Animals can be sacrificed by cervical dislocation at 2, 30, 60, and 120 min post-injection (n=2-4) and data can be quantified into % ID/g as described (Sivapackiam, J., et al. Synthesis, molecular structure, and validation of metalloprobes for assessment of MDR1 P-glycoprotein-mediated functional transport. Dalton Trans 39, 5842-5850 (2010)). The brains can be removed and dissected into cerebellums and remaining whole brain fractions prior to weighing and counting to evaluate regional differences in the location of radiotracer in comparison with transgenic mice.

In some configurations, biodistribution and pharmacokinetic studies can assist in pharmacokinetic analysis, in general, and in evaluation of $^{18}$F-AI-182 and/or other agents to permeate the BBB. In the absence of target, radiolabeled heterocyclic molecules can demonstrate uptake in brains of control mice, followed by washout of activity, resulting in low background signals. However, in the presence of plaques in transgenic APPsw$^{+/-}$/PS1 mice, enhanced accumulation and retention in brains can allow noninvasive imaging of mice.

Various embodiments of the present teachings include validation and correlation of MicroPET imaging with $^{18}$F-AI-182 and/or other agents.

In various configurations, validation and correlation of MicroPET imaging with $^{18}$F-AI-182 and/or other agents can be performed in age-matched BL/6 (control) and APPsw$^{+/-}$/PS1 mouse models on MicroPET/CT Focus 220 scanner. Twenty-six frames can be acquired over a 3 hour scan period with the following frame sequences: 5×1 min, 5×2 min, 5×5 min, 8×10 min, and 3×20 min. Frames of the original reconstructed PET data can be summed, and this summed image can be co-registered with CT. Regions of interest can be drawn and tissue-time activity curves (TAC) can be constructed by plotting the percent injected dose per c.c. tissue (% ID/cc).

From control mice, peak activity in the brain can be detected within the first 5 minutes post bolus injection and rapid clearance can be detected over the subsequent 2 to 3 hours. For APPsw$^{+/-}$/PS1 mice, the early peak can be comparable in magnitude and time, but tracer clearance can be significantly slower, reflecting binding of $^{18}$F-AI-182 and/or other agents to Aβ plaques. The differences between normal and APPsw$^{+/-}$/PS1 mice can increase with time. This difference can be correlated with plaque load in a cohort of mice.

Various embodiments of the present teachings include SAR studies to develop agents including but not limited to heterocyclic molecules capable of detecting Aβ plaques in early stages of AD prior to clinical expression.

In various configurations, candidate Aβ-targeted imaging agents can include but are not limited to the following characteristics: a) specific binding to Aβ plaques; b) specific binding to a prevalent binding site on Aβ; c) high first-pass extraction into the brain and region specific binding consistent with pathological localization of Aβ; d) minimal binding to the white matter for sensitivity to detect plaques at earlier stages of the disease to segregate pools of patients likely to benefit from therapeutics, and e) excretion from organs of the body over a time period for MIRD analysis. $^{18}$F-AI-182 as an agent demonstrates the above listed characteristics. $^{18}$F-AI-182 can offer a scaffold template for further SAR exploration to develop second generation Aβ-targeted agents.

Various embodiments of the present teachings include characterization of molecules via standard analytical tools.

In various configurations, these embodiments can include docking studies that can utilize Glide and ADME calculations using QProp. Molecules can be chemically characterized via standard analytical tools. Binding affinities with other agents, such as PIB, AV-45, and AZD4694 can be compared. Molecules demonstrating different binding sites on Aβ compared to these agents can be identified. Molecules demonstrating high first-pass extraction into brains of transgenic mice and low white matter binding to nonhuman primate or human tissues can be characterized in vivo through biochemical characterization via multiple binding and competitive displacement assays as well as through biodistribution and pharmacokinetic studies.

EXAMPLES

The present teachings including descriptions provided in the Examples, are not intended to limit the scope of any claim or aspect. Unless specifically presented in the past tense, an example can be a prophetic or an actual example. The following non-limiting examples are provided to further illustrate the present teachings. Those skilled in the art, in light of the present disclosure, will appreciate that many changes can be made in the specific embodiments that are disclosed and still obtain a like or similar result without departing from the spirit and scope of the present teachings.

Example 1

This example illustrates an Aβ targeted probe of the present teachings.

Utilizing the agent F-AI-182, a heterocyclic molecule was synthesized via multiple steps, purified via chromatography, crystallized in methylene chloride and pentane mixture, and the single crystal structure was determined. F-AI-182 was further characterized via standard analytical tools, including $^1$H NMR, proton-decoupled $^{13}$C-NMR, $^{19}$F NMR, high resolution mass spectroscopy (HRMS), and analyzed for uniformity using HPLC (Waters) equipped with a dual λ detector (2487) set to 280 and 364 nm on a semi-preparative C-18 column (Vydac).

Example 2

This example illustrates $^{18}$F-AI-182 synthesis and testing.

For bioassays described in following sections, $^{18}$F-AI-182 was synthesized via standard nucleophilic substitution, employing 2,2,2-kryptofix/$^{18}$F and AI-182-tosylate analog, purified on a C-18 (Vydac) column employing a gradient eluent mixture of ethanol and water, using radio-HPLC system equipped with a radiodetector (Bioscans). The fraction at R$_t$=15 min was collected, concentrated, and resuspended in PBS to 5% ethanol for all radiotracer bioassays. Furthermore, $^{18}$F-AI-182 was also characterized by spiking with an analytically characterized sample of an unlabeled F-AI-182 counterpart, prior to injection on the radio-HPLC.

Figure 1:
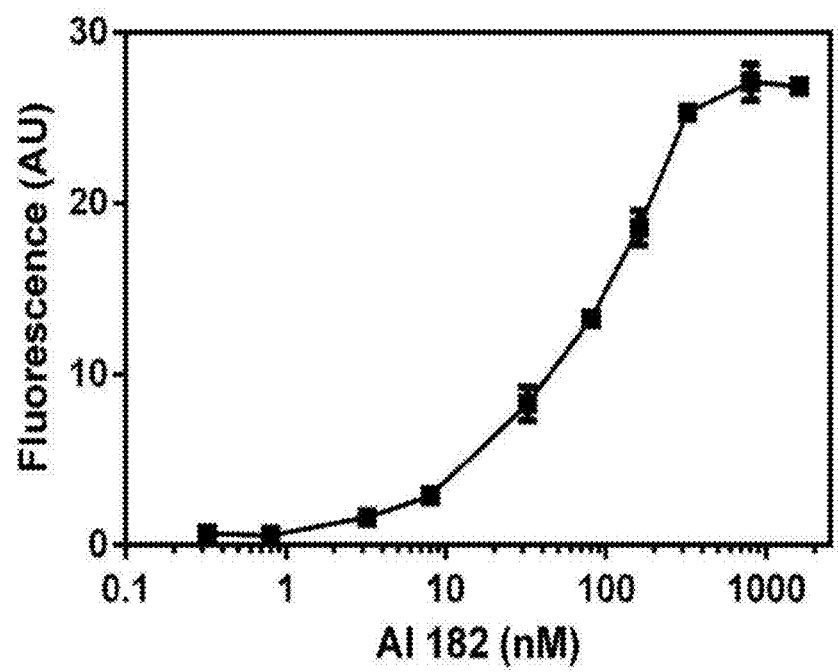
FIG. 1 illustrates concentration dependent and saturable binding (binding constant, 59±7 nM) to preformed Aβ1-42 fibrils of agent F-AI-182, of structure

The agent F-AI-182 shows concentration dependent and saturable binding (binding constant, 59±7 nM; FIG. 1) to preformed Aβ1-42 fibrils, stains both fibrillar and diffuse plaques ex vivo in the hippocampus and cortical region of brain sections in APPsw$^{+/-}$/PS1 mice (FIG. 2) and human tissues (FIG. 5), and incorporates F-18 ($^{18}$F; $t_{1/2}$=110 min), a radionuclide for medical PET imaging (Mahmood, A. & Jones, A. Technetium Radiopharmaceuticals. Handbook of Radiopharmaceuticals. 323-362 (2003); Eckelman, W. The Development of $^{99m}$Tc Radiopharmaceuticals for Perfusion and Biochemistry: In Technetium and Rhenium in Chemistry and Nuclear Medicine 3. M. Nicolini, G. Bandoli and U. Mazzi (Eds.). Cortina Int., Verona, Italy. pp. 571-580. (1990); Narra, R., et al. A Neutral Tc-99m Complex for Myocardial Imaging. J. Nucl. Med. 30, 1830-1837 (1989); Stadalnik, R., Kudo, M., Eckelman, W. & Vera, D. In vivo functional imaging using receptor-binding radiopharmaceuticals: 99mTc-galactosyl-neoglycoalbumin (TcNGA). Investigative Radiology 28, 64-70 (1993)). The radiolabeled counterpart $^{18}$F-AI-182 showed a transient high uptake in brains (7.28±0.46% % ID/g) of FVB mice (FIG. 3), and followed by washout from blood (25% faster than AV-45; FIG. 4) in absence of targeted plaques and remains nonmetabolized in human serum. The high first-pass extraction into brain coupled with faster clearance from the blood pool and lack of metabolites offer characteristics that could potentially enhance overall signal to background ratios and assist image analysis. Multi-photon microscopy in live APPsw$^{+/-}$/PS1 (15 months old) mice demonstrated that F-AI-182 labels plaques in brain parenchyma and blood vessels (CAA), by 5-min post intravenous administration (FIG. 6). The F-AI-182 showed facile clearance from non-targeted regions and the plaques remain labeled for investigated time points.

Binding assays of F-AI-182 with preformed Aβ$_{1-42}$ aggregates were performed in PBS. Following excitation at 410 nm, fluorescence spectrum of F-AI-182 recorded in PBS containing 1% ethanol showed a broad emission peak 540-610 nm with E$_{max}$ at 570 nm. Upon incubation with preformed of Aβ(1-42) aggregates, the peak 570 nm showed remarkable enhancement in the fluorescence indicating binding to Aβ aggregates, similar to enhancement in fluorescence of thioflavin T in PBS (a positive control; data not shown). Fluorescence was not observed using Aβ aggregates alone in PBS upon excitation at 410 nm (a negative control). Binding assays of the F-AI-182 with preformed Aβ$_{1-42}$ aggregates indicated a nearly saturable binding with a K$_d$=59±7 nM (FIG. 1). Comparative analyses can be performed with other compounds such as AV-45, BAYER 94-9172, and AZD4694. An agent can be interacting with either of the two modestly high affinity binding sites (BS1& BS2) or recognizing an entirely new site on Aβ$_{1-42}$. F-AI- 182 can register different complementary binding sites in relation to Aβ-pathophysiology compared to current agents.

Example 3

This example illustrates ex vive staining studies.

FIG. 2 illustrates ex vivo staining studies were performed on brain sections (50 μm) of an APPsw$^{+/-}$/PS1 mouse (24 months old) and a control WT mouse (BL/6; 24 months old) using well-established procedures. Briefly, tissue sections were immunostained with mouse monoclonal antibody and visualized by donkey-anti-mouse HJ3.4 Aβ monoclonal antibody-Alexa 568 as a positive control. Brain sections of APPsw$^{+/-}$PS1$^{+/-}$mice showed abundant staining of Aβ compared with minimal levels in WT mouse (FIG. 2). Using F-AI-182 (100 nM, 60 min), abundant staining of fibrillar and diffuse plaques in the hippocampus and cortical regions of brain sections in APPsw$^{+/-}$PS1$^{+/-}$mice was observed— arrows indicate labeling of Aβ plaques (arrows, diffuse; arrow head, fibrillar). By comparison, no staining in WT mice was seen either with F-AI-182 or the antibody indicating the targeting specificity of F-AI-182. The slides were analyzed on a Zeiss LSM 5 PASCAL confocal system coupled to a Zeiss Axiovert 200 microscope.

Example 4

This example illustrates biodistribution studies of $^{18}$F-AI-182.

For in vivo imaging of Aβ plaques, the basic pharmacokinetic model in an unaffected normal brain involves high initial penetration of the agent, followed by rapid clearance due to lack of a binding target. However, in AD brains, high initial penetration can be followed by regional retention as the agent binds to Aβ thus leading to differential kinetics. To accomplish this objective, biodistribution studies of $^{18}$F-AI-182 were performed in normal FVB mice for assessment of signal to noise ratios and clearance profiles. Brain uptake of $^{18}$F-AI-182 was analyzed in terms of percent injected dose per gram of the brain tissue (% ID/g). Biodistribution studies with HPLC purified $^{18}$F-AI-182 in normal mice revealed a transient brain uptake value of 7.28±0.46% ID/g and 1.54±0.06% ID/g, 5 min and 120 min post tail-vein injection, respectively, giving a 5 min/120 min clearance a ratio of 4.73, providing evidence for the ability of $^{18}$F-AI-182 to cross the BBB and permeate into brain in vivo (FIG. 3). This initial brain uptake value (5 min) in normal mice is approximately 15-fold high compared with our Aβ-targeted $^{99m}$Tc-Peptides (Harpstrite, S. E., Prior, J., Binz, K., Piwnica-Worms, D. & Sharma, V. $^{99m}$Tc-Peptide conjugates for imaging β-amyloid in the brain. ACS Med Chem Lett (2013) under review). Additionally, compared to $^{18}$F-AV-45 (Liver: 17.0 t 0.69 (2 min), 4.96±0.90 (120 min); Kidney: 14.19±2.34 (2 min), 2.19±0.36 (120 min), $^{18}$F-AI-182 clears rapidly from non-targeted tissues, such as liver and kidney (Liver: 16.32±1.41 (5 min), 2.71±0.21 (120 min); Kidney: 6.76±1.57 (5 min), 1.57±0.08 (120 min) and these clearance profiles could translate into better MIRD analysis. For comparison, $^{18}$F-AV-45 demonstrates brain uptake values of 7.33±1.54% ID/g and 1.80±0.07% ID/g at 2 min and 120 min post-injection (Choi, S. R., et al. Preclinical properties of 18F-AV-45: a PET agent for Abeta plaques in the brain. J Nucl Med 50, 1887-1894 (2009)) respectively, thus providing a 2 min/120 min clearance ratio of 4.07 in normal mice that lack target sites (FIG. 3). Net brain uptake of $^{18}$F-AI-182 is 1.2-fold higher than that of $^{18}$F-AV-45. The initial data point for $^{18}$F-AI-182 is at 5 min compared with 2 min for $^{18}$F-AV-45. Our data indicates a 5 min uptake compared with a 2 min data point reported for $^{18}$F-AV-45 thus we do expect these 2 min/120 min ratios to be much superior, upon comparative analysis at the same time points. $^{18}$F-AI-182 undergoes 25% faster blood clearance from 5 min to 120 min compared with the 18F-AV-45 (FIG. 4). Compared with $^{11}$C-PIB (Mathis, C., et al. Synthesis and evaluation of $^{11}$C-labeled 6-substituted 2-arylbenzothiazoles as amyloid imaging agents. J Med Chem 46, 2740-2754 (2003)) and $^{18}$F-AV-45 (Choi, S. R., et al. Preclinical properties of $^{18}$F-AV-45: a PET agent for Abeta plaques in the brain. J Nucl Med 50, 1887-1894 (2009)) that undergo facile metabolism in vivo, $^{18}$F-AI-182 remains non-metabolized in human serum.

Example 5

This example illustrates staining experiments with an F-AI-182 agent.

Staining experiments were performed with human brain tissues. Tissue samples were obtained from the frontal lobe of clinically and neuropathologically well-characterized cases. The neuropathological diagnosis of AD was based on the criteria of the Consortium to Establish a Registry for Alzheimer's Disease (CERAD) (Mirra, S., et al. The Consortium to Establish a Registry for Alzheimer's Disease (CERAD). Part II. Standardization of the neuropathologic assessment of Alzheimer's disease. Neurology 41, 479-486 (1991)) or the National Institute of Aging-Reagan Institute (NIA-RI) (Hyman, B. & Trojanowski, J. Consensus recommendations for the postmortem diagnosis of Alzheimer disease from the National Institute on Aging and the Reagan Institute Working Group on diagnostic criteria for the neuropathological assessment of Alzheimer disease. J Neuropathol Exp Neurol 56, 1095-1097. (1997)). For experiments, highly specific Aβ-targeted antibody (10D5, Eli Lilly, a positive control, used in histopathological core of the ADRC post-mortem cases) confirmed the presence of Aβ plaques. As shown in FIG. 5, Aβ-targeted F-AI-182 showed abundant staining of Aβ plaques in the hippocampus of a 90 year-old female with AD. In FIG. 5 on the left, the fluorescent probe (F-AI-182, 50 nM) labels both the compact fibrillar amyloid (arrow) and more diffuse beta-amyloid deposits (arrowhead); on the right of FIG. 5, Aβ (10D5, Eli Lilly) immunohistochemistry reveals similar beta-amyloid plaques in a section from the same tissue block as in (b); bar=100 μm. Additionally, F-AI-182 demonstrated labeling of both the fibrillar and the diffuse plaques. The ability of the F-AI-182 agent to detect diffuse plaques represents an advancement to enable PET imaging of mildly demented individuals (an earlier manifestation of AD) prior to clinical expression (Price, J. L., et al. Neuropathology of nondemented aging: presumptive evidence for preclinical Alzheimer disease. Neurobiology of aging 30, 1026-1036 (2009); Morris, J. C., et al. Cerebral amyloid deposition and diffuse plaques in "normal" aging: Evidence for presymptomatic and very mild Alzheimer's disease. Neurology 46, 707-719 (1996); Price, J. L. & Morris, J. C. Tangles and plaques in nondemented aging and "preclinical" Alzheimer's disease. Annals of neurology 45, 358-368 (1999); Schmitt, F. A., et al. "Preclinical" AD revisited: neuropathology of cognitively normal older adults. Neurology 55, 370-376 (2000)), thereby offering a window of opportunity for therapeutic interventions for better management of disease.

To demonstrate ability of the agent to label plaques in vivo, multiphoton imaging was conducted in live APP/PS1 12 month old mice, post intravenous injection of F-AI-182.

Prior to imaging, dextran-Texas Red was injected for mapping the blood vessels. Following labeling of blood vessels, F-AI-182 (2 mg/kg, dissolved in DMSO/PEG; 20:80) was intravenously injected. A z-stack image series was acquired from cortex surface to a depth of approx. 100 μm using microscope LSM 510META NLO (Carl-Zeiss Inc). Multi-photon microscopy in live APPsw+/−/PS1 (15 months old) mice demonstrated that F-AI-182 can label plaques in brain parenchyma and blood vessels (CAA), less than 5-min post intravenous administration. The labeling of brain parenchymal plaques was visible within 10 min, indicating facile clearance from non-targeted regions and remained labeled for 30 min (FIG. 6). Multi-photon imaging can be done using $^{18}$F-AI-182, other agents, or second generation agents (Bacskai, B., et al. Four-dimensional multiphoton imaging of brain entry, amyloid binding and clearance of an amyloid-3 ligand in transgenic mice. Proc Natl Acad Sci USA 100, 12462-12467 (2003)).

Example 6

This example illustrates methods of assessment of binding sites.

There is an NMR-deduced structure in the protein data bank for $A\beta_{1-42}$ (PDB ID: 2BEG). To assess binding sites of PIB, AV-45, and AI-182, using procedures described earlier in our laboratories (Sundaram, G. S. M, Harpstrite, S. E., Kao, J. L., Collins, S. D. & Sharma, V. A New Nucleoside Analogue with Potent Activity against Mutant sr39 Herpes Simplex Virus-1 (HSV-1) Thymidine Kinase (TK). Organic letters (2012)), we used sitemap to determine binding sites on $A\beta_{1-42}$, generated a grid, then docked PIB, AV-45, and AI-182 to determine rank order (AV-45>F-AI-182>PIB) based upon the Glide score. FIG. 7 depicts the post docking view of PIB (left), AV-45 (Middle), and F-AI-182 (Right). Ligand interaction diagram indicated that PIB 6-hydroxy substituent of the benzothiazole ring forms a hydrogen bond with Leu 17 and smallest surface of hydrophobic interactions with amino acid residues of Aβ-42. While pyridine ring of AV-45 participated in π-π interactions with Phe 19 as well as highest surface of hydrophobic interactions, F-AI-182 retained π-π interactions but also shows intermediate hydrophobic interaction surface thus supporting the rank order of the glide score. Building on the principles that: a) π electrons play a role in biochemical interactions (Kumpf, R. A. & Dougherty, D. A. A mechanism for ion selectivity in potassium channels: computational studies of cation-pi interactions. Science 261, 1708-1710 (1993)); b) Aβ recognizes planner molecules; and c) extended conjugation systems are more likely to offer more flexibility for interaction with other sites, we can explore a focused SAR around two scaffolds: a) slight variations in position of the heteroatoms in the six membered pyridine ring or 5-membered ring of benzothiazole in addition to variation in number of ethylene glycol moieties on the 6-position of benzothiazole ring and b) modification of dialkyl amino group with other functional groups.

Example 7

This example illustrates labeling of Aβ plaques in APPsw+/− (24 months old) mice using F-AI-183.

Examples of brain tissue section staining of APPsw+/− (24 months old) mice using F-AI-183 are shown in FIG. 8. Arrows indicate labeling of Aβ plaques (arrows, fibrillar plaques). The slides were analyzed using a Nikon Ti-E PFS inverted microscope equipped with a Nikon 10x 0.3 NA Plan APO objective, Prior H117 ProScan flat top linear encoded stage, and Prior Lumen 200PRO illumination system with standard DAPI and FITC filter sets. The images were acquired using a Photometrics CoolSNAP HQ2 digital camera and MetaMorph microscopy automaton, and imaging software. Images were processed and analyzed using the Image J software package (NIH).

Example 8

This example illustrates detection of compact Aβ plaques in brain cross-sections of frontal lobe by F-AI-183.

F-AI-183 detected compact Aβ plaques in the brain cross-sections of frontal lobe of an 88-year-old female with neuropathologically confirmed Alzheimer's disease as shown in FIG. 9. The fluorescent probe (F-AI-183) labels fibrillar amyloid (arrow). The slides were analyzed on a using a Nikon Ti-E PFS inverted microscope equipped with a Nikon 10x0.3 NA Plan APO objective, Prior H117 ProScan flat top linear encoded stage, and Prior Lumen 200PRO illumination system with standard DAPI and FITC filter sets. The images were acquired using a Photometrics CoolSNAP HQ2 digital camera, and MetaMorph microscopy automaton, and imaging software. Images were processed and analyzed using the Image J software package (NIH).

Example 9

This example illustrates NMR data for some compounds of the present teachings.

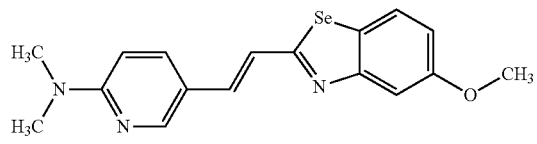

25

$^1$H NMR (400 MHz, CDCl$_3$): 3.17 (s, 6H), 3.83 (s, 3H), 6.59 (d, J=8.4 Hz, 1H), 7.02 (d, J=9.2 Hz, 1H), 7.16 (d, J=16.0 Hz, 1H), 7.25 (t, J=14.0 Hz, 2H), 7.74 (d, J=8.4 Hz, 1H), 7.83 (d, J=8.4 Hz, 1H), 8.45 (s, 1H); $^{13}$C NMR (100 MHz, CDCl$_3$): 37.14, 55.77, 104.13, 106.05, 115.31, 118.33, 119.21, 123.02, 134.05, 134.22, 148.93, 159.15, 171.33

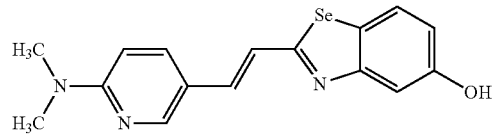

26

$^1$H NMR (400 MHz, CDCl$_3$): 3.10 (s, 6H), 6.75 (d, J=8.8 Hz, 1H), 6.81 (d, J=8.4 Hz, 1H), 7.32 (d, J=16.4 Hz, 1H), 7.43 (d, J=16.4 Hz, 1H), 7.81 (d, J=8.0 Hz, 1H), 8.18 (d, J=8.4 Hz, 1H), 8.37 (s, 1H), 9.62 (s, 1H); $^{13}$C NMR (100 MHz, CDCl$_3$): 38.21, 107.08, 108.21, 109.62, 115.05, 116.25, 119.69, 121.37, 125.88, 126.44, 135.49, 136.17, 136.54, 157.05, 172.69.

(F-AI-183)

¹H NMR (400 MHz, CDCl₃): 3.15 (s, 6H), 4.28 (d, J=27.8 Hz, 2H), 4.77 (d, J=47.2 Hz, 2H), 6.56 (dd, J=8.8, 3.2 Hz, 1H), 6.96 (d, J=8.4 Hz, 1H), 7.14 (d, J=16.4 Hz, 1H), 7.27 (d, J=6.0 Hz, 1H), 7.52 (d, J=16.8 Hz, 1H), 7.72 (dd, J=8.6, 3.0 Hz, 2H), 8.31 (s, 1H); ¹³C NMR (100 MHz, CDCl₃): 38.12, 67.29, 67.50, 81.00, 82.70, 106.08, 107.81, 115.05, 119.31, 120.78, 124.98, 134.41, 134.80, 136.36, 149.22, 157.85; ¹⁹F NMR (282 MHz, CFCl₃): −224 ppm; HRMS (FAB) m/z calc. for $C_{18}H_{18}FN_3OSe$: [M]⁺ 391.0599. found: 391.0602.

¹H NMR (400 MHz, CDCl₃): 3.24 (s, 6H), 3.87 (s, 3H), 6.93 (d, J=7.2 Hz, 1H), 7.16 (s, 2H), 7.50 (s, 1H), 7.70 (d, J=7.4 Hz, 1H), 8.50 (s, 2H); ¹³C NMR (100 MHz, CDCl₃): 37.27, 55.52, 107.18, 114.85, 117.07, 121.54, 124.81, 128.10, 132.81, 156.54, 159.16, 161.64, 172.49

¹H NMR (400 MHz, CDCl₃): 3.17 (s, 6H), 6.83 (dd, J=8.0, 1.6 Hz, 1H), 7.30 (s, 1H) 7.40 (d, J=8.8 Hz, 2H), 7.82 (d, J=8.8 Hz, 2H), 8.75 (s, 2H), 9.63 (s, 1H); ¹³C NMR (100 MHz, CDCl₃): 39.28, 109.72, 115.23, 117.66, 121.91, 125.92, 126.55, 133.49, 156.95, 157.07, 157.49, 161.59, 172.49

(F-AI-187)

¹H NMR (400 MHz, CDCl₃): 3.24 (s, 6H), 4.28 (d, J=27.6 Hz, 2H), 4.80 (d, J=47.2 Hz, 2H), 6.97 (d, J=7.2 Hz, 1H), 7.17 (bs, 1H), 7.50 (s, 1H), 7.72 (d, J=7.2 Hz, 1H), 8.52 (s, 2H); ¹³C NMR (100 MHz, CDCl₃): 37.28, 67.31, 67.51, 80.97, 82.67, 107.95, 110.00, 115.36, 117.04, 121.46, 125.01, 128.78, 133.01, 156.47, 156.57, 157.93, 158.57, 161.66, 172.72; ¹⁹F NMR (282 MHz, CFCl₃): −224 ppm; HRMS (FAB) m/z calc. for $C_{17}H_{18}FN_4OSe$: [M]⁺ 392.0594. found: 392.0603.

¹H NMR (400 MHz, CDCl₃): 0.12 (s, 6H), 0.92 (s, 9H), 3.24 (s, 6H), 4.01-4.03 (m, 2H), 4.09-4.12 (m, 2H), 6.94 (dd, J=8.8, 2.4 Hz, 1H), 7.17 (d, J=1.2 Hz, 1H), 7.50 (d, J=2.4 Hz, 1H), 7.70 (d, J=8.4 Hz, 1H), 8.53 (s, 2H); ¹³C NMR (100 MHz, CDCl₃): 31.04, 42.24, 68.44, 76.22, 110.76, 112.22, 121.21, 124.34, 129.86, 140.02, 142.74, 149.96, 152.44, 162.68, 172.86.

¹H NMR (400 MHz, CDCl₃): 2.43 (s, 3H), 3.24 (s, 6H), 4.20 (bs, 2H), 4.41 (bs, 2H), 6.71 (d, J=9.0 Hz, 1H), 6.81 (d, J=9.0 Hz, 1H), 7.17-7.41 (m, 4H), 7.65-7.69 (m, 1H), 7.82 (d, J=7.6 Hz, 2H), 8.52 (s, 1H), 8.66 (s, 1H); ¹³C NMR (100 MHz, CDCl₃): 21.64, 37.23, 65.72, 68.06, 108.04, 108.25, 115.08, 115.50, 116.88, 121.41, 124.78, 124.96, 125.25, 128.00, 129.85, 131.04, 133.12, 144.95, 156.60, 157.35, 158.59, 162.68, 171.84

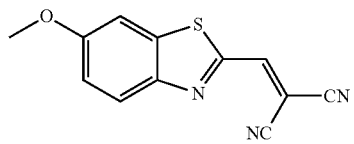 [SMILES: COc1ccc2nc(C=C(C#N)C#N)sc2c1]

¹H NMR (300 MHz, CD₃CN): 8.25 (s, 1H), 8.08 (d, 1H), 7.63 (d, 1H), 7.27 (dd, 1H), 3.92 (s, 3H)

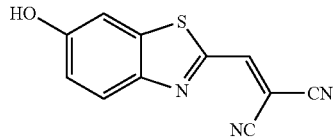 [SMILES: N#CC(C#N)=Cc1nc2ccc(O)cc2s1]

¹H NMR (300 MHz, acetone-d₆): 10.00-9.00 (br, s, 1H), 8.51 (s, 1H), 8.09 (d, 1H), 7.63 (d, 1H), 7.28 (dd, 1H)

¹H NMR (300 MHz, acetone-d₆): 8.55 (s, 1H), 8.16 (d, 1H), 7.85 (d, 1H), 7.39 (d, 1H), 4.93-4.29 (m, 4H).

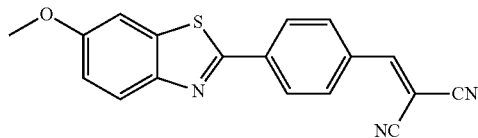 [SMILES: COc1ccc2nc(-c3ccc(C=C(C#N)C#N)cc3)sc2c1]

¹H NMR (300 MHz, dmso-d₆): 8.59 (s, 1H), 8.25 (d, 2H), 8.08 (d, 2H), 8.00 (d, 1H), 7.77 (d, 1H), 7.18 (dd, 1H), 3.87 (s, 3H)

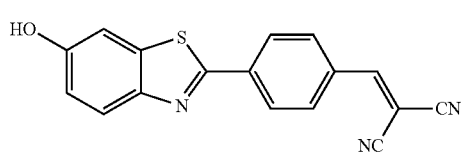 [SMILES: N#CC(C#N)=Cc1ccc(-c2nc3ccc(O)cc3s2)cc1]

¹H NMR (300 MHz, acetone-d₆): 9.00 (br, s, 1H), 8.39 (s, 1H), 8.30 (d, 2H), 8.18 (d, 2H), 7.94 (d, 1H), 7.52 (d, 1H), 7.14 (dd, 1H). MS(LRESI) m/z=304.0547 (M+H⁺).

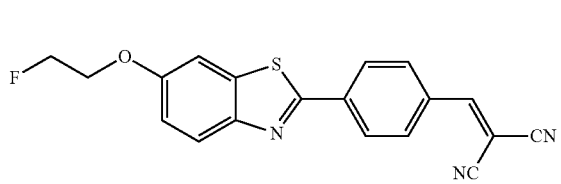 [SMILES: N#CC(C#N)=Cc1ccc(-c2nc3ccc(OCCF)cc3s2)cc1]

¹H NMR (300 MHz, acetone-d₆): 8.39 (s, 1H), 8.31 (d, 2H), 8.18 (d, 2H), 8.02 (d, 1H), 7.73 (d, 1H), 7.25 (dd, 1H), 4.94-4.36 (m, 4H). MS(LRESI) m/z=350.2 (M+H⁺).

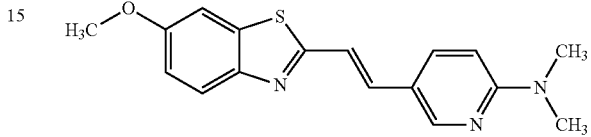

¹H NMR (400 MHz, CDCl₃): 3.15 (s, 6H), 3.88 (s, 3H), 6.55 (d, J=8.4 Hz, 1H), 7.04 (d, J=9.2 Hz, 1H), 7.14 (d, J=16.0 Hz, 1H), 7.29 (t, J=14.0 Hz, 2H), 7.71 (d, J=8.4 Hz, 1H), 7.83 (d, J=8.4 Hz, 1H), 8.29 (s, 1H); ¹³C NMR (100 MHz, CDCl₃): 38.14, 55.79, 104.13, 106.05, 115.31, 118.0, 119.41, 123.02, 134.08, 134.22, 148.93, 159.15, 165.33

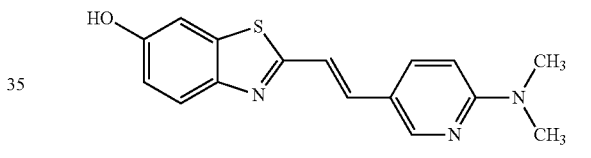

¹H NMR (400 MHz, CDCl₃): 3.03 (s, 6H), 6.65 (d, J=8.4 Hz, 1H), 6.88 (d, J=7.6 Hz, 1H), 7.24-7.32 (m, 2H), 7.66 (d, J=8.4 Hz, 2H), 7.90 (d, J=7.6 Hz, 1H), 8.29 (s, 1H), 9.82 (s, 1H); ¹³C NMR (100 MHz, CDCl₃): 38.04, 106.51, 107.08, 116.11, 118.03, 119.58, 123.17, 134.13, 134.96, 135.60, 147.47, 149.36, 155.90, 159.25, 163.97.

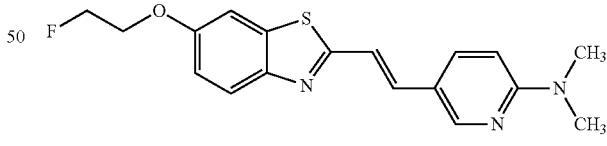

AI-182

¹H NMR (400 MHz, CDCl₃): 3.14 (s, 6H), 4.28 (d, J=26.0 Hz, 2H), 6.65 (d, J=8.4 Hz, 1H), 4.77 (d, J=49.6 Hz, 2H), 6.55 (d, J=8.8 Hz, 1H), 7.08 (d, J=9.2 Hz, 1H), 7.13 (d, J=16.4 Hz, 1H), 7.26-7.33 (m, 2H), 7.70 (d, J=8.4 Hz, 1H), 7.84 (d, J=9.2 Hz, 1H), 8.29 (s, 1H), 9.82 (s, 1H); ¹¹C NMR (100 MHz, CDCl₃): 38.10, 38.13, 67.63, 67.84, 81.01, 82.70, 105.32, 106.05, 115.67, 117.86, 119.34, 123.12, 134.23, 134.33, 148.98, 156.36, 159.17, 165.74; ¹⁹F NMR (282 MHz, CFCl₃): −224 ppm; HRMS (FAB) m/z calc. for C₁₈H₁₈FN₃OS: [M]⁺ 343.155. found: 343.1152.

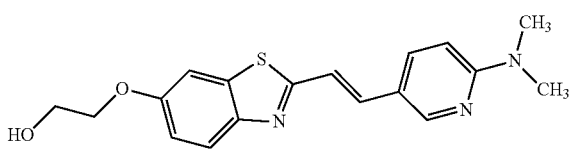 [SMILES: CN(C)c1ccc(/C=C/c2nc3ccc(OCCO)cc3s2)cn1]

¹H NMR (400 MHz, CDCl₃): 3.17 (s, 6H), 3.96 (s, 2H), 4.20 (s, 2H), 6.56 (d, J=8.8 Hz, 1H), 7.06 (d, J=8.4 Hz, 1H), 7.14 (d, J=16.4 Hz, 1H), 7.24-7.32 (m, 2H), 7.72 (d, J=8.8 Hz, 2H), 7.82 (d, J=8.8 Hz, 1H), 8.29 (s, 1H).

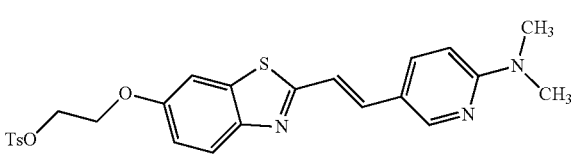 [SMILES: Cc1ccc(S(=O)(=O)OCCOc2ccc3nc(/C=C/c4ccc(N(C)C)nc4)sc3c2)cc1]

¹H NMR (400 MHz, CDCl₃): 2.42 (s, 3H), 3.16 (s, 6H), 4.22 (s, 2H), 4.41 (s, 2H), 6.56 (d, J=8.8 Hz, 1H), 7.06 (d, J=8.4 Hz, 1H), 7.14 (d, J=16.4 Hz, 1H), 7.24-7.32 (m, 2H), 7.72 (d, J=8.8 Hz, 2H), 7.82 (d, J=8.8 Hz, 1H), 8.22-8.43 (m, 3H), 8.51-8.92 (m, 2H).

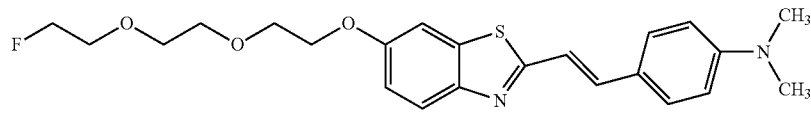 [SMILES: CN(C)c1ccc(/C=C/c2nc3ccc(OCCOCCOCCF)cc3s2)cc1]

¹H NMR (400 MHz, CDCl₃): 3.14 (s, 6H), 3.61-3.80 (m, 6H), 3.82 (s, 2H), 4.22 (s, 2H), 4.44 (d, J=49.4 Hz, 2H), 6.55 (d, J=8.8 Hz, 1H), 7.08 (d, J=9.2 Hz, 1H), 7.13 (d, J=16.4 Hz, 1H), 7.26-7.33 (m, 2H), 7.70 (d, J=8.4 Hz, 1H), 7.84 (d, J=9.2 Hz, 1H), 8.29 (d, J=9.2 Hz, 2H); ¹⁹F NMR (282 MHz, CFCl₃): −224 ppm; HRMS (FAB) m/z calc. for C₂₃H₁₈FN₂O₃S: [M]⁺ 430.1726. found: 430.1780.

Example 10

This example illustrates imaging of cancer cells using AI-182 as a fluorescent probe.

In these experiments, human carcinoma cells were incubated with AI-182

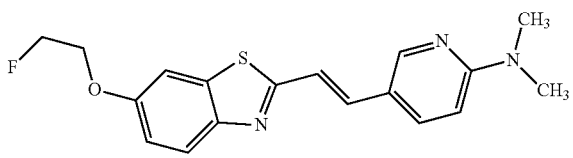 [SMILES: CN(C)c1ccc(/C=C/c2nc3ccc(OCCF)cc3s2)cn1]

(5 μM) at 37° C. in the presence of 5% CO₂ for 30 min, and examined using a Nikon Ti-E PFS inverted high resolution microscope equipped with a Nikon (Magnification: 20×) Plan APO objective, Prior H117 ProScan flat top linear encoded stage, and Prior Lumen 200PRO illumination system with standard DAPI and FITC filter sets. Results are shown in FIG. 10. Top row: Live Cell Imaging of Human Glioblastoma (U87) Cells Using AI-182. Middle row: Live Cell Imaging of Human Pancreatic Cancer Cells (PANC1) Using AI-182. Bottom row: Live Cell Imaging of Human Pancreatic Cancer Cells (Mia PaCa-2) Using AI-182. Note accumulation of the probe within cells.

All references cited herein are incorporated by reference, each in its entirety. Applicant reserves the right to challenge any conclusions presented by any of the authors of any reference.

What is claimed is:

1. A compound or a pharmaceutically acceptable salt thereof selected from the group consisting of

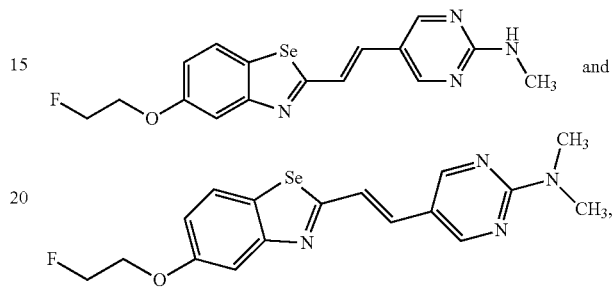

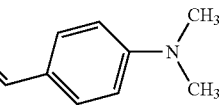

or a pharmaceutically acceptable salt thereof.

2. A gold nanoparticle conjugated to the compound according to claim 1.

3. A method of imaging distribution of amyloid beta in a sample or a subject, comprising:
   administering the compound or a pharmaceutically acceptable salt thereof according to claim 1 to the sample or subject wherein the compound or pharmaceutically acceptable salt thereof comprises a radionuclide; and
   subjecting the sample or subject to PET or SPECT scanning.

4. A method of imaging cardiac systemic amyloidosis in a subject, comprising administering an imaging effective amount of the compound or a pharmaceutically acceptable salt thereof according to claim 1 to the subject, and imaging systemic amyloidosis in the subject by PET or SPECT scanning.

5. A complex comprising:
   the compound or a pharmaceutically acceptable salt thereof according to claim 1; and
   a gold nanoparticle.

6. The compound or a pharmaceutically acceptable salt thereof according to claim 1, Wherein the compound is

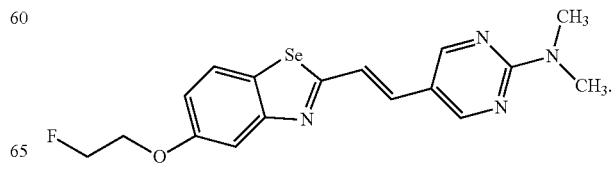

7. The compound or a pharmaceutically acceptable salt thereof according to claim 6, wherein the F is $^{18}$F.

8. The compound or a pharmaceutically acceptable salt thereof according to claim 1, wherein the F is $^{18}$F.

* * * * *

UNITED STATES PATENT AND TRADEMARK OFFICE
CERTIFICATE OF CORRECTION

PATENT NO. : 10,335,504 B2
APPLICATION NO. : 15/089516
DATED : July 2, 2019
INVENTOR(S) : G. S. M. Sundaram, Jothilingam Sivapackiam and Vijay Sharma It is certified that error appears in the above-identified patent and that said Letters Patent is hereby corrected as shown below:

In the Specification

Column 1 Lines 20-22 should read:
This invention was made with government support under AG033328 and AG030498 awarded by the National Institutes of Health. The government has certain rights in the invention.

Signed and Sealed this
Thirteenth Day of August, 2019

Andrei Iancu
*Director of the United States Patent and Trademark Office*

UNITED STATES PATENT AND TRADEMARK OFFICE
CERTIFICATE OF CORRECTION

PATENT NO.        : 10,335,504 B2
APPLICATION NO.   : 15/089516
DATED             : July 2, 2019
INVENTOR(S)       : G. S. M. Sundaram et al.

It is certified that error appears in the above-identified patent and that said Letters Patent is hereby corrected as shown below:

In the Specification

Government Support Paragraph at Column 1, Lines 20-22 should read:
This invention was made with government support under AG030498, AG033328, and AG050263 awarded by the National Institutes of Health. The government has certain rights in the invention.

This certificate supersedes the Certificate of Correction issued August 13, 2019.

Signed and Sealed this
Fifth Day of October, 2021

Drew Hirshfeld
*Performing the Functions and Duties of the
Under Secretary of Commerce for Intellectual Property and
Director of the United States Patent and Trademark Office*